United States Patent
Bonfanti et al.

(10) Patent No.: US 10,266,543 B2
(45) Date of Patent: *Apr. 23, 2019

(54) MACROCYCLIC DEAZA-PURINONES FOR THE TREATMENT OF VIRAL INFECTIONS

(71) Applicant: Janssen Sciences Ireland UC, Little Island, Co Cork (IE)

(72) Inventors: Jean-François Bonfanti, Andé (FR); Jérôme Michel Claude Fortin, Igoville (FR); Philippe Muller, Andé (FR); Frédéric Marc Maurice Doublet, Isneauville (FR); Pierre Jean-Marie Bernard Raboisson, Wavre (IE); Eric Pierre Alexandre Arnoult, Le Vaudreuil (FR)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/781,291

(22) PCT Filed: Mar. 28, 2014

(86) PCT No.: PCT/EP2014/056270
§ 371 (c)(1),
(2) Date: Sep. 29, 2015

(87) PCT Pub. No.: WO2014/154859
PCT Pub. Date: Oct. 2, 2014

(65) Prior Publication Data
US 2016/0304531 A1 Oct. 20, 2016

(30) Foreign Application Priority Data
Mar. 29, 2013 (EP) .................................. 13161865

(51) Int. Cl.
*C07D 491/18* (2006.01)
*C07D 491/22* (2006.01)
*C07D 498/18* (2006.01)
*C07D 498/22* (2006.01)
*C07D 471/18* (2006.01)

(52) U.S. Cl.
CPC ......... *C07D 491/18* (2013.01); *C07D 471/18* (2013.01); *C07D 491/22* (2013.01); *C07D 498/18* (2013.01); *C07D 498/22* (2013.01)

(58) Field of Classification Search
None
See application file for complete search history.

(56) References Cited

U.S. PATENT DOCUMENTS

| | | | |
|---|---|---|---|
| 6,028,076 A | 2/2000 | Hirota et al. | |
| 6,329,381 B1 | 12/2001 | Kurimoto et al. | |
| 6,376,501 B1 | 4/2002 | Isobe et al. | |
| 6,458,798 B1 | 10/2002 | Fujita et al. | |
| 6,503,908 B1 | 1/2003 | Maw | |
| 6,583,148 B1 | 6/2003 | Kelley et al. | |
| 6,951,866 B2 | 10/2005 | Fujita et al. | |
| 7,030,118 B2 | 4/2006 | Lombardo et al. | |
| 7,091,232 B2 | 8/2006 | Chow et al. | |
| 7,498,409 B2 | 3/2009 | Vlach et al. | |
| 7,524,852 B2 | 4/2009 | Arai et al. | |
| 7,531,547 B2 | 5/2009 | Dillon et al. | |
| 7,754,728 B2 | 7/2010 | Isobe et al. | |
| 7,923,554 B2 | 4/2011 | Hoornaert et al. | |
| 8,012,964 B2 | 9/2011 | Kurimoto et al. | |
| 8,022,077 B2 | 9/2011 | Simmen et al. | |
| 8,455,458 B2 | 6/2013 | Marcum et al. | |
| 8,486,952 B2 | 7/2013 | Boy et al. | |
| 8,637,525 B2 | 1/2014 | Boy et al. | |
| 8,916,575 B2 | 12/2014 | McGowan et al. | |
| 9,133,192 B2 | 9/2015 | McGowan et al. | |
| 9,284,304 B2 | 3/2016 | McGowan et al. | |
| 9,365,571 B2 | 6/2016 | McGowan et al. | |
| 9,376,448 B2 | 6/2016 | Charifson et al. | |
| 9,416,114 B2 | 8/2016 | Gembus et al. | |
| 9,422,250 B2 | 8/2016 | McGowan | |
| 9,499,549 B2 | 11/2016 | McGowan et al. | |
| 9,556,176 B2 | 1/2017 | Bonfanti et al. | |
| 9,556,199 B2 | 1/2017 | McGowan et al. | |
| 9,598,378 B2 | 3/2017 | McGowan et al. | |
| 9,663,474 B2 | 5/2017 | Last et al. | |
| 9,878,996 B2 | 1/2018 | Silverman et al. | |
| 2005/0054590 A1 | 3/2005 | Averett | |
| 2006/0258682 A1 | 11/2006 | Liao et al. | |
| 2007/0225303 A1 | 9/2007 | Ogita et al. | |
| 2009/0285782 A1 | 11/2009 | Gao et al. | |
| 2010/0143299 A1 | 6/2010 | Gao et al. | |

(Continued)

FOREIGN PATENT DOCUMENTS

| CN | 101784548 A | 7/2010 |
|---|---|---|
| EP | 0882727 | 12/1998 |

(Continued)

OTHER PUBLICATIONS

International Search Report and Written Opinion dated Jul. 21, 2014, for Corresponding International Application PCT/EP2014/056270.
Abdillahi, et al., "Synthesis of a Novel Series of Thieno[3,2-d]pyrimidin-4-(3H)-ones", Synthesis, vol. 9: pp. 1428-1430 (2010).
Banker (Editor), "Prodrugs", Modern Pharmaceutics, Third Edition: pp. 596 (1976).
Baraldi, et al., "New Strategies for the Synthesis of A3 Adenosine Receptor Antagonists", Bioorganic & Medicinal Chemistry, vol. 11: pp. 4161-4169 (2003).
Barker, et al., "A Rapid Conversion of 3-Oxothiolanes into 3-Aminothiophenes", Synthetic Communications, vol. 32(16): pp. 2565-2568 (2002).

(Continued)

*Primary Examiner* — Noble E Jarrell

(57) ABSTRACT

This invention relates to macrocyclic deaza-purinones derivatives, processes for their preparation, pharmaceutical compositions, and their use in treating viral infections.

20 Claims, No Drawings
Specification includes a Sequence Listing.

(56) References Cited

U.S. PATENT DOCUMENTS

| | | |
|---|---|---|
| 2014/0148433 A1 | 5/2014 | Follmann et al. |
| 2015/0274676 A1 | 10/2015 | McGowan et al. |
| 2015/0299221 A1* | 10/2015 | Bonfanti ............ C07D 487/16 514/257 |
| 2015/0336907 A1 | 11/2015 | Gembus et al. |
| 2016/0304531 A1 | 10/2016 | Bonfanti et al. |

FOREIGN PATENT DOCUMENTS

| | | |
|---|---|---|
| EP | 0899263 A3 | 3/1999 |
| EP | 1552842 A1 | 6/2003 |
| EP | 1110951 A1 | 6/2006 |
| EP | 1939198 A1 | 7/2008 |
| EP | 1970373 A1 | 9/2008 |
| EP | 2133353 A1 | 12/2009 |
| EP | 2138497 A1 | 12/2009 |
| JP | 64063582 | 3/1989 |
| JP | 2000053653 | 2/2000 |
| JP | 2000053654 | 2/2000 |
| JP | 2008222557 A | 9/2008 |
| JP | 2009528989 A | 8/2009 |
| JP | 2010522151 A | 7/2010 |
| JP | 2010532353 A | 10/2010 |
| WO | 199801448 A1 | 1/1998 |
| WO | 199808847 A1 | 3/1998 |
| WO | 199814448 A1 | 4/1998 |
| WO | 199850370 A1 | 11/1998 |
| WO | 199928321 A1 | 6/1999 |
| WO | 199932122 A1 | 7/1999 |
| WO | 199940091 A1 | 8/1999 |
| WO | 199941253 A1 | 8/1999 |
| WO | 200006577 A1 | 2/2000 |
| WO | 200061562 A1 | 10/2000 |
| WO | 2002087513 A2 | 11/2002 |
| WO | 2002088080 A2 | 11/2002 |
| WO | 2003055890 A1 | 7/2003 |
| WO | 2005007672 A2 | 1/2005 |
| WO | 2005092892 A1 | 10/2005 |
| WO | 2006015985 A1 | 2/2006 |
| WO | 2006050843 A1 | 5/2006 |
| WO | WO 2006/117670 A1 | 11/2006 |
| WO | 2007034881 A1 | 3/2007 |
| WO | 2007056208 A1 | 5/2007 |
| WO | 2007063934 A1 | 6/2007 |
| WO | 2007084413 A2 | 7/2007 |
| WO | 2007093901 A1 | 8/2007 |
| WO | 2008009078 A2 | 1/2008 |
| WO | 2008073785 A2 | 6/2008 |
| WO | 2008075103 A1 | 6/2008 |
| WO | 2008114008 A1 | 9/2008 |
| WO | 2008114817 A1 | 9/2008 |
| WO | 2008114819 A1 | 9/2008 |
| WO | 2008115319 A2 | 9/2008 |
| WO | 2008147697 A1 | 12/2008 |
| WO | 2009005687 A1 | 1/2009 |
| WO | 2009023179 A2 | 2/2009 |
| WO | 2009030998 A1 | 3/2009 |
| WO | 2009067081 A1 | 5/2009 |
| WO | 2009080836 A2 | 7/2009 |
| WO | 2009099650 A2 | 8/2009 |
| WO | 2009032668 A3 | 9/2009 |
| WO | 2009134624 A1 | 11/2009 |
| WO | 2010006025 A1 | 1/2010 |
| WO | 2010007116 A3 | 1/2010 |
| WO | 2010133885 A1 | 11/2010 |
| WO | 2011049825 A1 | 4/2011 |
| WO | 2011049987 | 4/2011 |
| WO | 2011062253 A1 | 5/2011 |
| WO | 2011062372 A3 | 5/2011 |
| WO | 2012066335 A1 | 5/2012 |
| WO | 2012067269 A1 | 5/2012 |
| WO | 2012136834 | 10/2012 |
| WO | 2012156498 A1 | 11/2012 |
| WO | 2013068438 A1 | 5/2013 |
| WO | 2013117615 A1 | 8/2013 |
| WO | 2014053595 A1 | 4/2014 |

OTHER PUBLICATIONS

Bell, et al., "Chemistry of 5-Pyrimidinecarboxaldehydes", Journal of Heterocyclic Chemistry, vol. 29: pp. 41-44 (Jan.-Feb. 1983).

Bennet, et al. (Editor), "Part XIV Oncology", Cecil Textbook of Medicine, vol. 1, 20th Edition: pp. 1004-1010 (1996).

Bizanek, et al., Isolation and Structure of an Intrastrand Cross-Link Adduct of Mitomycin C nd DNA', Biochemistry, 1992, pp. 3084-3091, vol. 31.

Brittain, et al., "Effects of Pharmaceutical Processing on Drug Polymorphs and Solvates", Polymorphism in Pharmaceutical Solids, 1999, pp. 331-360, Chapter 8.

Bruns, et al, "Solubilities of Adenosine Antagonists Determined by Radioreceptor Assay", Journal of Pharmacy and Pharmacology, vol. 41: pp. 590-594 (1989).

Chawla, et al., "Challenges in Polymorphism of Pharmaceuticals", Current Research & Information on Pharmaceutical Sciences, vol. 5(1): pp. 9-12 ( Jan.-Mar. 2004).

De Clercq, et al., "(S)-9-(2,3-Dihydroxypropyl)adenine: An Aliphatic Nucleoside Analaog with Broad-Spectrum Antiviral Activity", Science, 1978, pp. 563-565, vol. 200.

De Nardo, "Toll-Like Receptors: Activation, Signalling and Transcriptional Modulation", Cytokine, 2015, pp. 181-189, vol. 74.

Dermer, "Another Anniversary for the War on Cancer", Bio/Technology, vol. 12: pp. 320 (Mar. 1994).

Douglas, Jr., "Introduction of Viral Diseases", Cecil Textbook of Medicine, 20th Edition, vol. 2: pp. 1973-42 (1996).

Freshney, et al., Culture of Animal Cells, Manual of Basic Technique, 1983, pp. 1-6, Chapter 1.

Fried, et al., "Peginterferon Alfa-2a Plus Ribavirin for Chronic Hepatitis C Virus Infection", New England Journal of Medicine, Sep. 26, 2002, pp. 975-985, vol. 347 (13).

Grimm, et al., "Toll-like receptor (TLR) 7 and TLR8 expression on CD133+ cells in colorectal cancer points to a specific rold for inflammation inducted TLRs in tumourigenesis and tumour progression", European Journal of Cancer, 2010, pp. 2849-2857, vol. 46.

Hackam, et al., "Translation of Research Evidence From animals to Humans", JAMA, vol. 296 (14): pp. 1731-1732 (2006).

Hoffmann, "The Immune Response of Drosophila", Nature, vol. 426: pp. 33-38 (Nov. 6, 2003).

Hood, et al., "Immunoprofiling toll-like receptor ligands Comparison of Immunostimulatory and proinflammatory profiles in ex vivo human blood models", Human Vaccines, vol. 6(4): pp. 322-335 (Apr. 2010).

Horscroft, et al., "Antiviral applications of toll-like receptor agonists", J. Antimicrob. Chemother., pp. 1-13 (Jan. 18, 2016).

Huddleston, et al., "A Convenient Synthesis of 2-Substituted 3-Hydroxy—and 3-Amino-Thiophens From Derivatives of 2-Choroacrylic Acid", Synthetic Communications, vol. 9(8): pp. 731-734 (1979).

Isobe, et al., "Synthesis and Biological Evaluation of Novel 9-Substituted-8-Hydroxyadenine Derivatives as Potent Inferferon Inducers", J. Med. Chem., vol. 49; pp. 2088-2095 (2006).

Isobe, et al., "Synthesis and Structure-Activity Relationships of 2-Substituted-8-hydroxyadenine Derivatives as Orally Available Interferon Inducers without Emetic Side Effects", Bioorganic & Medicinal Chemistry, vol. 11: pp. 3641-3647, (2003).

Jiang, et al., "Synthesis of 4-chlorothieno[3,2-d]pyrimidine", Chemical Industry and Engineering Progress, vol. 30: pp. 2532-35, (2011). [With English Abstract].

Jordan, "Tamoxifen: A Most Unlikely Pioneering Medicine", Nature Reviews, vol. 2: pp. 205-213, (Mar. 2003).

Jurk, et al., "Human TLR7 or TLR8 Independently Confer Responsiveness to the Antiviral Compound R-848", Nature Immunology, Jun. 2002, pp. 499, vol. 3 (6).

(56) References Cited

OTHER PUBLICATIONS

Kanzler, et al., "Therapeutic Targeting of Innate Immunity with Toll-Like Receptor Agonists and Antagonists", Nature Medicine, vol. 13(5): pp. 552-559 (May 2007).
Krieger, et al, Enhancement of Hepatitis C Virus RNA Replication by Cell Culture, Journal of Virology, May 1, 2001, 4614-1624, 75-10, DE.
Kurimoto, et al., "Synthesis and Evaluation of 2-Substituted 8-Hydroxyadenines as Potent Interferon Inducers with Improved Oral Bioavailabilities", Bioorganic & Medicinal Chemistry, vol. 12; pp. 1091-1099 (2004).
Kurimoto, et al., "Synthesis and Structure—Activity Relationships of 2-Amino-8-hydroxyadenines as Orally Active Interferon Inducing Agents", Bioorganic & Medicinal Chemistry, vol. 11: pp. 5501-5508 (2003).
Lee et al., "Activation of Anti-Hepatitis C Virus Responses via Toll-Like Receptor 7", PNAS, vol. 3 (6); pp. 1828-1833 (Feb. 7, 2006).
Lu, et al., "Synthesis and Biological Activity of 3-and 5-Amino Derivatives of Pyridine-2Carboxaldehyde Thiosemicarbazone", J. Med. Chem, Vo. 39: pp. 2586-2593 (1996).
Lohmann et al, Viral and Cellular Determinants of Hepatitis C Virus RNA Replication in Cell Culture, Journal of Virology, Mar. 2003, pp. 3007-3019, vol. 77, No. 5.
Lohmann, et al., Replication of Subgenomic Hepatitis C Virus RNAs in a Hepatoma Cell Line, Science, 1999, pp. 110-113, vol. 285.
Makkouk et al., "The potential use of Toll-Like Receptors (TLR) agonistd and antagonists as prophylactic and/or therapeutic agents", Immunopharmacology and Immunotoxicology, vol. 31(3): pp. 331-338 (2009).
McGowan et al., "Novel Pyrimidine Toll-Like Receptor 7 and 8 Dual Agonists to Treat Hepatitis B Virus", Journal of Medicinal Chemistry, 2016, pp. 7936-7949, vol. 59 No. 17.
Mesguiche, et al., "4-Alkoxy-2,6-diaminopyrimidine Derivatives: Inhibitors of Cyclin Dependent Kinases 1 and 2", Bioorganic & Medicinal Chemistry Letters, vol. 13: pp. 217-22 (2003).
Moreau, et al., "Synthesis of cyclic adenosine 5'-diphosphate ribose analogues: a C2' endo/syn "southern" ribose conformation underlies activity at the sea urchin cADPR receptor", Organic & Biomolecular Chemistry, vol. 9: pp. 278-290 (2011).
Musmuca, et al, "Small-Molecule interferon Inducers. Toward the Comprehension of the Molecular Determinants through Ligand-Based Approaches", J. Chem. Inf. Model., vol. 49: pp. 1777-1786 (2009).
Newman, et al., "Solid-State Analysis of the Active Pharmaceutical Ingredient in Drug Products", Drug Discovery Today, Oct. 19, 2003, pp. 898-905, vol. 8(19).
O'Hara, et al., "Regioselective Synthesis of Imidazo[4,5-g]quinazoline Quinone Nucleosides and Quinazoline Amino Nucleosides. Studies of their Xanthine Oxidase and Purine Nucleoside Phosphorylase Substrate Activity", J. Org. Chem. vol. 56: pp. 776-785 (1991).
Ohto, et al., "Structure and Function of Toll-Like Receptor 8", Microbes and Infections, vol. 16: pp. 273-282 (2014).
Organic Syntheses Collective, "3-Methylcoumarone", Organic Syntheses Collective, 1963, pp. 43-46, vol. 4.
Roethle, et al., "Identification and Optimization of Pteridinone Toll-Like Receptor 7 (TLR7) Agonists for the Oral Treatment of Viral Hepatitis", Journal of Medicinal Chemistry, Vol. 56; pp. 7324-73333 (2013).
Takeda, et al., "Toll-Like Receptors", Annu. Rev. Immunol, vol. 21: pp. 335-376 (2003).
Thomas, et al., "Investigating Toll-Like Receptor Agonists for Potential to Treat Hepatitis C Virus Infection", Antimicrobial Agents and Chemotherapy, vol. 51(8): pp. 2969-2978 (Aug. 2007).
Tomonori, et al., "Ti-Crossed-Claisen Condensation between Carboxylic Ester and Acid Chlorides or Acids: A Highly Selective and General Method for the Preparation of Various β-Keto Esters", Journal of the American Chemical Society, vol. 127:pp. 2854-55 (2005).
Tran, et al., "Design and optimization of orally active TLR7 agonists for the treatment of hepatitis C virus infection", Bioorganic & Medicinal Chemistry Letters, vol. 21: pp. 2389-2393 (2011).
Ulevitch, "Therapeutics Targeting the Innate Immune System", Nature, vol. 4: pp. 512-520 (Jul. 2004).
Ulrich, et al., "Crystallization", Kirk-Othmer Encyclopedia of Chemical Technology, Chapter 4: pp. 1-63, (Aug. 16, 2002).
Vedantham, et al., "Mechanism of Interferon Action in Hairy Cell Leukemia: A Model of Effective Cancer Biotherapy", Cancer Research, vol. 52: pp. 1056-1066 (Mar. 1, 1992).
Vippagunta, et al., "Crystalline Solids", Advance Drug Delivery Reviews, vol. 48: pp. 3-26 (2001).
Warshakoon, et al., "Potential Adjuvantic Properties of Innate Immune Stimuli", Human Vaccines, vol. 5(6): pp. 381-394 (Jun. 2009).
Wermuth, "Molecular Variations Based on Isosteric Replacements", The Practice of Medicinal Chemistry, 1996, pp. 203-237, Ch. 13.
Wolff, et al, Burger's Medicinal Chemistry and Drug Discovery, -, 1994, pp. 975-977, 5th Edition, vol. 1.
Yin, et al., "Synthesis of 2,4-Diaminoquinazolines and Tricyclic Quinazolines by Cascade Reductive Cyclization of Methyl N-Cyano-2-nitrobenzimidates", J. Org. Chem., vol. 77: pp. 2649-2658 (2012).
Yu, et al, "Toll-Like Receptor 7 Agonists: Chemical Feature Based", PLOS ONE, vol. 8 (3): pp. 1-11 e56514, (Mar. 20, 2013).
Yu, et al., "Dual Character of Toll-Like Receptor Signaling: Pro-Tumorigenic Effects and Anti-Tumor Functions", Biochimica et Biophysica Acta, vol. 1835: pp. 144-154 (2013).
Zhao, et al., "Toll-Like Receptors and Prostate Cancer", Frontiers in Immunology, vol. 5 (Article 352): pp. 1-7 (Jul. 2014).

\* cited by examiner

MACROCYCLIC DEAZA-PURINONES FOR THE TREATMENT OF VIRAL INFECTIONS

CROSS REFERENCE TO RELATED APPLICATIONS

This application is a 35 U.S.C. §371 nationalization of PCT application PCT/EP2014/056270 filed Mar. 28, 2014, which claims priority to European patent application EP 13161865.4 filed Mar. 29, 2013, each of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 6, 2017, is named TIP0293USPCT_Sequence_listing.txt and is 620 bytes in size.

This invention relates to macrocyclic deaza-purinones derivatives, processes for their preparation, pharmaceutical compositions, and their use in treating viral infections.

The present invention relates to the use of macrocyclic deaza-purinones derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For detailed reviews on toll-like receptors see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as purine derivatives in WO 2006/117670, adenine derivatives in WO 98/01448 and WO 99/28321, and pyrimidines in WO 2009/067081.

However, there exists a strong need for novel Toll-Like receptor modulators having preferred selectivity, higher potency, higher metabolic stability, and an improved safety profile compared to the compounds of the prior art.

In the treatment of certain viral infections, regular injections of interferon (IFN-alfa) can be administered, as is the case for hepatitis C virus (HCV). For more information see Fried et al. Peginterferon-alfa plus ribavirin for chronic hepatitis C virus infection, *N Engl J Med* 2002; 347: 975-82. Orally available small molecule IFN inducers offer the potential advantages of reduced immunogenicity and convenience of administration. Thus, novel IFN inducers are potentially effective new class of drugs for treating virus infections. An example of a small molecule IFN inducer having antiviral effect see De Clercq, E.; Descamps, J.; De Somer, P. *Science* 1978, 200, 563-565.

IFN-alfa is also given in combination with other drugs in the treatment of certain types of cancer (Eur. J. Cancer 46, 2849-57, and Cancer Res. 1992, 52, 1056). TLR 7/8 agonists are also of interest as vaccine adjuvants because of their ability to induce pronounced Th1 response (Hum. Vaccines 2010, 6, 322-335, and Hum. Vaccines 2009, 5, 381-394).

In accordance with the present invention a compound of formula (I) is provided

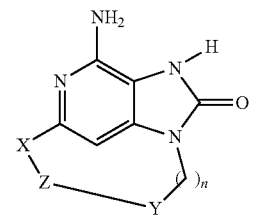

n = 1 to 3 and pharmaceutically accepted salts thereof, wherein
X is oxygen, nitrogen or sulfur
Y represents an aromatic ring or heterocyclic ring comprising at least a nitrogen, optionally substituted by one or more substituents independently selected from $C_{1-6}$alkyl, $C_{1-4}$alkoxy, trifluoromethyl or halogen,
Z represents $C_{1-10}$ saturated or unsaturated alkyl optionally substituted by an alkyl or alkylhydroxyl;
or Z represents $C_{1-6}$alkyl-NH—C(O)— $C_{1-6}$alkyl-, $C_{1-6}$alkyl-NH— or $C_{1-6}$alkyl-NH—C(O)—$C_{1-6}$alkyl-O—;
or Z represents $C_{1-10}$alkyl-O— wherein said alkyl is unsaturated or saturated and can optionally be substituted by an alkyl or alkylhydroxyl,
or Z represents $C_{1-6}$alkyl-O—$C_{1-6}$alkyl- wherein said alkyl is unsaturated or saturated and can optionally be substituted by an alkyl or alkylhydroxyl
or Z represents $C_{1-6}$alkyl-O—$C_{1-6}$alkyl-O— wherein said alkyl is unsaturated or saturated and can optionally be substituted by an alkyl or alkylhydroxyl.

Preferred compounds having one of the following formula's according to the invention were selected from the group of:

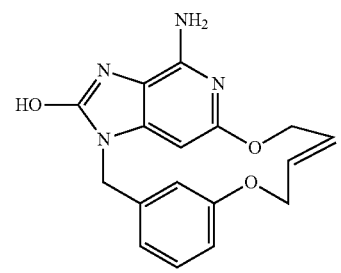

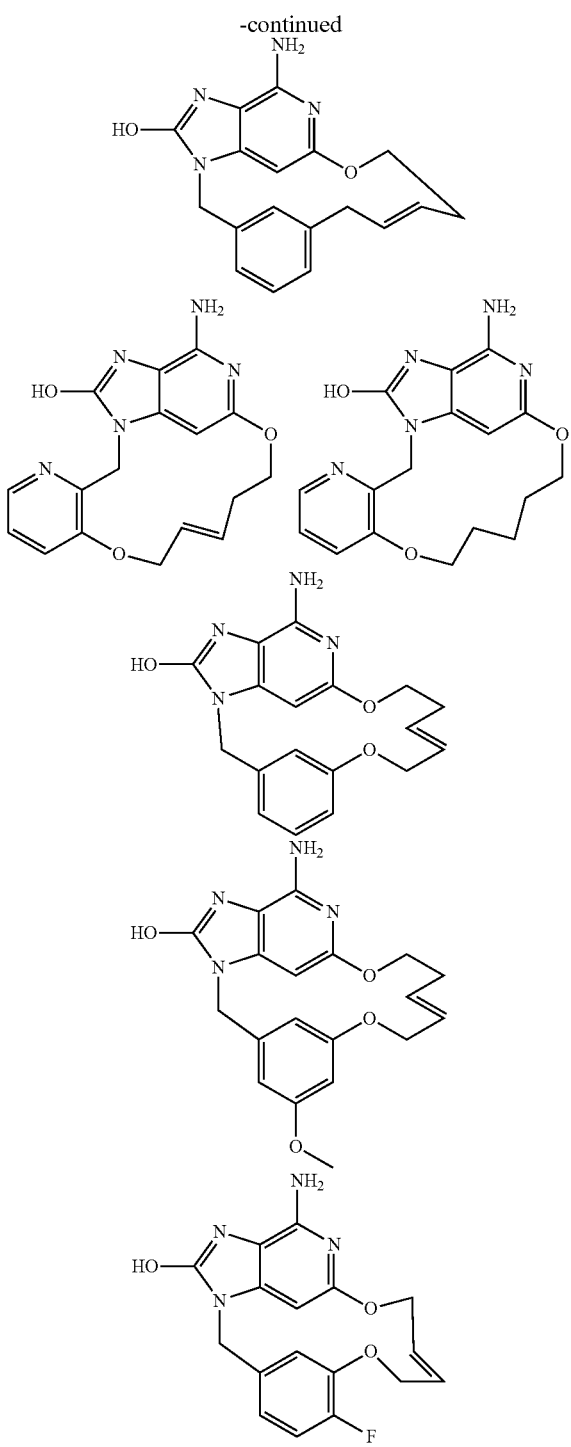

Part of the invention is also a pharmaceutical composition comprising a compound of formula (I) or a pharmaceutically acceptable salt, solvate or polymorph thereof together with one or more pharmaceutically acceptable excipients, diluents or carriers.

Furthermore to the invention belongs a compound of formula (I) or a pharmaceutically acceptable salt, solvate or polymorph thereof or a pharmaceutical composition above mentioned for use as a medicament.

The invention also relates to a compound of formula (I) or a pharmaceutically acceptable salt, solvate or polymorph thereof or a pharmaceutical composition above mentioned for use in the treatment of a disorder in which the modulation of TLR7 is involved.

The term "alkyl" refers to a straight-chain or branched-chain mostly saturated (but in specific compounds according to the invention being unsaturated) aliphatic hydrocarbon containing the specified number of carbon atoms.

The term "halogen" refers to fluorine, chlorine, bromine or iodine.

The term "alkoxy" refers to an alkyl (carbon and hydrogen chain) group singular bonded to oxygen like for instance a methoxy group or ethoxy group.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the invention can be present in a so-called "tautomer(s)" formation referring to isomers of organic compounds that readily interconvert by a chemical reaction called tautomerization. This reaction results in the formal migration of a hydrogen atom or proton, accompanied by a switch of a single bond and adjacent double bond.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets.

Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Overall Scheme in the Preparation of Final Products: Method 1

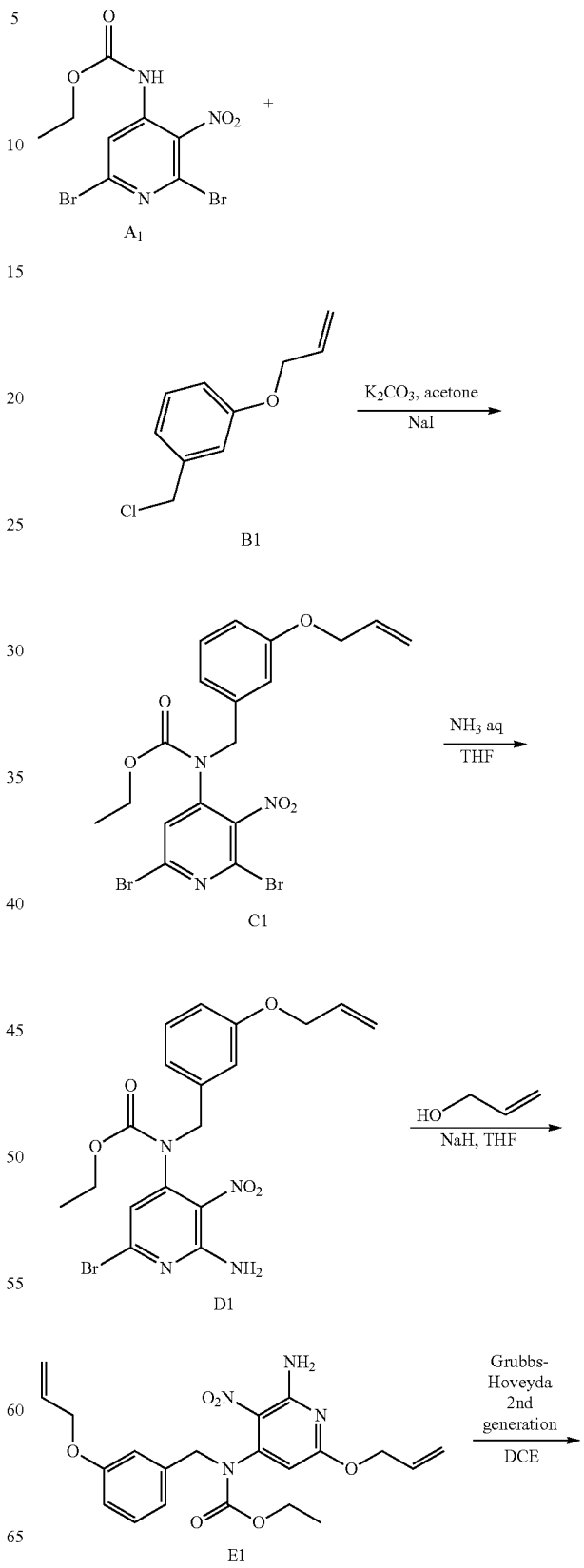

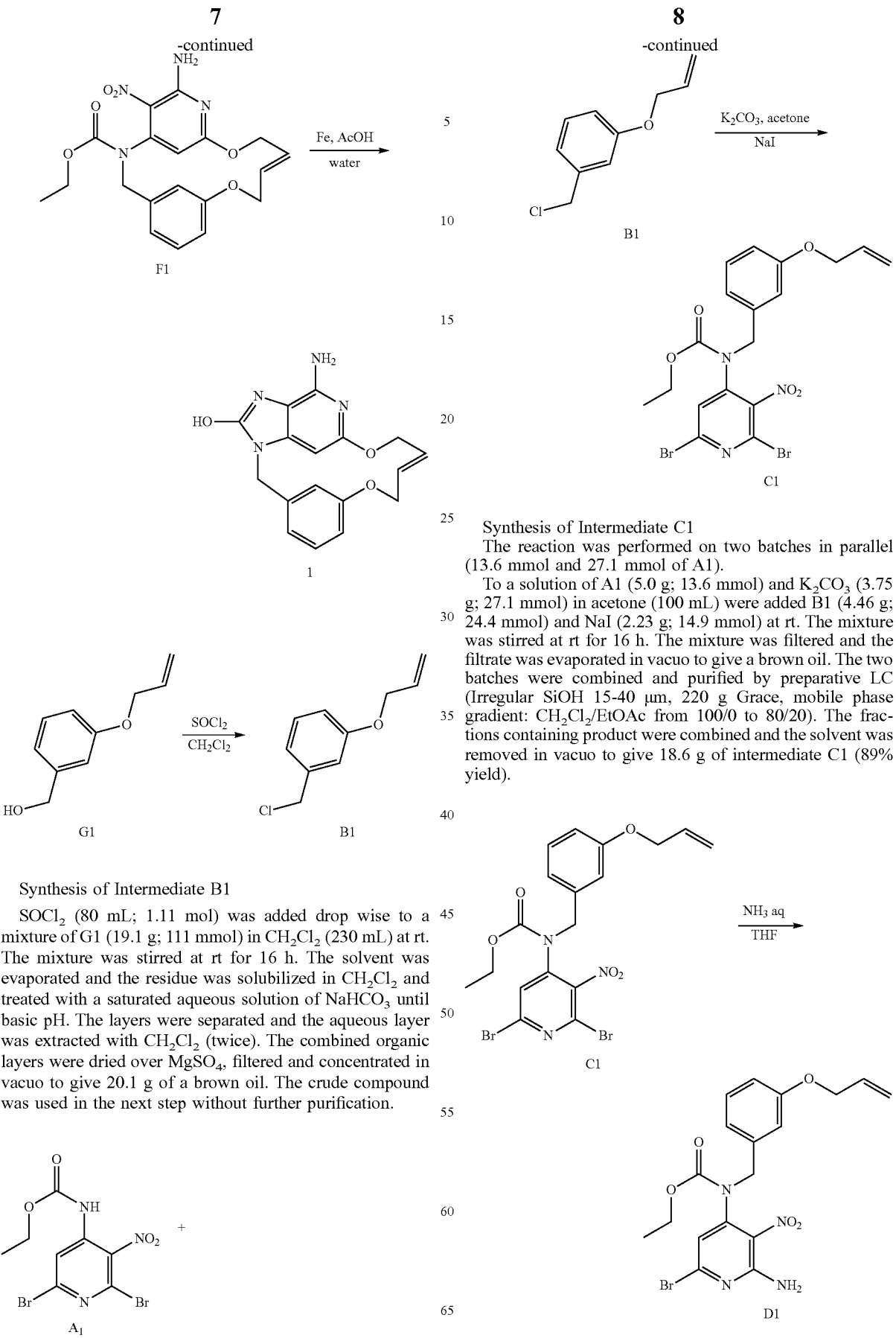

Synthesis of Intermediate C1

The reaction was performed on two batches in parallel (13.6 mmol and 27.1 mmol of A1).

To a solution of A1 (5.0 g; 13.6 mmol) and K$_2$CO$_3$ (3.75 g; 27.1 mmol) in acetone (100 mL) were added B1 (4.46 g; 24.4 mmol) and NaI (2.23 g; 14.9 mmol) at rt. The mixture was stirred at rt for 16 h. The mixture was filtered and the filtrate was evaporated in vacuo to give a brown oil. The two batches were combined and purified by preparative LC (Irregular SiOH 15-40 µm, 220 g Grace, mobile phase gradient: CH$_2$Cl$_2$/EtOAc from 100/0 to 80/20). The fractions containing product were combined and the solvent was removed in vacuo to give 18.6 g of intermediate C1 (89% yield).

Synthesis of Intermediate B1

SOCl$_2$ (80 mL; 1.11 mol) was added drop wise to a mixture of G1 (19.1 g; 111 mmol) in CH$_2$Cl$_2$ (230 mL) at rt. The mixture was stirred at rt for 16 h. The solvent was evaporated and the residue was solubilized in CH$_2$Cl$_2$ and treated with a saturated aqueous solution of NaHCO$_3$ until basic pH. The layers were separated and the aqueous layer was extracted with CH$_2$Cl$_2$ (twice). The combined organic layers were dried over MgSO$_4$, filtered and concentrated in vacuo to give 20.1 g of a brown oil. The crude compound was used in the next step without further purification.

Synthesis of Intermediate D1

To a solution of C1 (18.6 g; 36.1 mmol) in THF (300 mL) was added an aqueous solution of NH$_3$ (30%) (290 mL) at rt, and the mixture was stirred at rt for 16 h. The mixture was taken up with EtOAc and saturated NaCl solution, the layers were separated and the organic layer was dried over MgSO$_4$, filtered and the solvent was removed under reduced pressure to give 16.7 g of a yellow-orange oil. The crude was dried under high vacuum to give 16.5 g of a sticky yellow-orange solid, which was used directly in the next step.

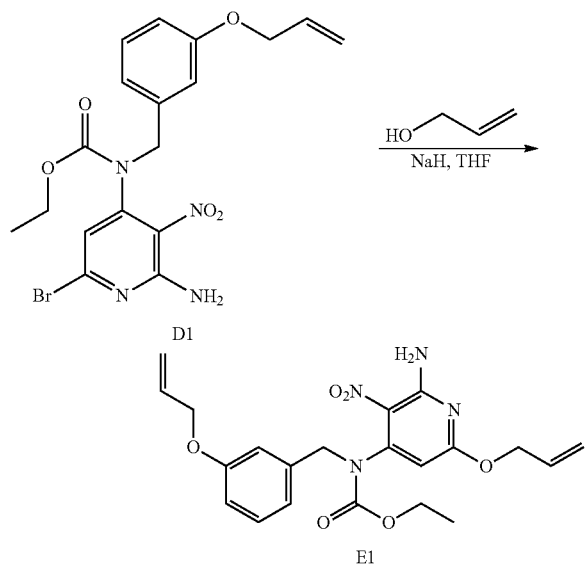

Synthesis of Intermediate E1

NaH (60% in oil) (1.75 g; 43.7 mmol) was added portion wise to allyl alcohol (50 mL) at rt. The mixture was stirred at rt for 30 min before being added drop wise to a solution of D1 (5 g; 11.1 mmol) in THF (124 mL) at 0° C. The resulting mixture was then stirred at rt for 1 h and was poured in saturated NH$_4$Cl aqueous solution. EtOAc and saturated NaCl aqueous solution were added, the layers were separated and the aqueous layer was extracted with EtOAc (once). The combined organic layers were dried over MgSO$_4$, filtered and the solvent was removed under reduced pressure to give a yellow oil. The crude compound was purified by preparative LC (Irregular SiOH 15-40 μm, 120 g Grace, liquid injection, mobile phase gradient: from Heptane/EtOAc 100/0 to 50/50) to give 4.04 g of intermediate E1 as a yellow oil (79% yield).

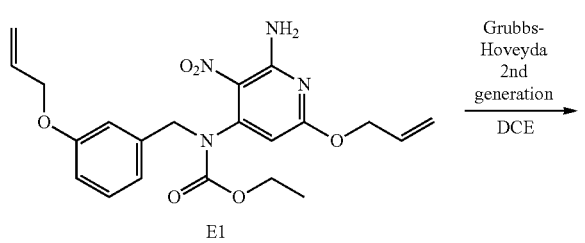

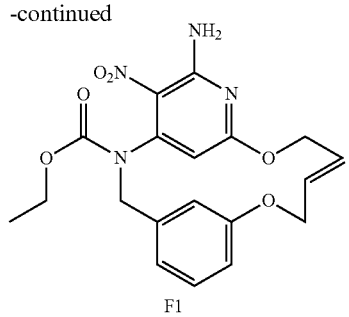

Synthesis of Intermediate F1

The reaction was performed in 2 batches of 850 mg and 2 batches of 1 g of E1.

Herein is the procedure for one batch of 850 mg:

In a schlenk flask, a solution of E1 (0.85 g; 1.98 mmol) and chlorodicyclohexylborane (1M solution in hexane) (400 μL; 400 μmol) in dichloroethane (570 mL) was stirred at 80° C. under N$_2$ atmosphere for 1 h. Grubbs-Hoveyda catalyst 2$^{nd}$ generation (124 mg; 198 μmol) was added and the mixture was stirred at 120° C. for 16 h. The mixture was degassed by N$_2$ bubbling for 10 min and further Grubbs-Hoveyda catalyst 2$^{nd}$ generation (124 mg; 198 μmol) and chlorodicyclohexylborane (1M solution in hexane) (400 μL; 400 μmol) were added. The mixture was stirred at 120° C. for 20 h.

The 2 batches were mixed and a ruthenium scavenger (SiliaBond DMT from SiliCycle) (10.4 g; 6.35 mmol) was added and the mixture was stirred at rt for 20 h. The reaction mixture was filtered through a pad of celite and the solvent was removed under reduced pressure to give a brown residue.

The residue was combined with the residue obtained from the two batches of 1 g of E1. The resulting brown residue was purified by preparative LC (Irregular SiOH 15-40 μm, 120 g Grace, dry loading, mobile phase gradient: from Heptane/EtOAc 100/0 to 0/100) to give 1.19 g of a brown solid. The brown solid was further purified by preparative LC (Stationary phase: irregular bare silica 40 g, mobile phase gradient: from CH$_2$Cl$_2$/EtOAc 90/10 to 80/20) to give 705 mg of a yellow solid. The yellow solid was further purified by achiral SFC (stationary phase: Amino 6 μm 150×21.2 mm), mobile phase: Gradient from 85% CO$_2$, 15% MeOH to 65% CO$_2$, 35% MeOH) to give 660 mg of intermediate F1 as a yellow solid (19% yield, E isomer).

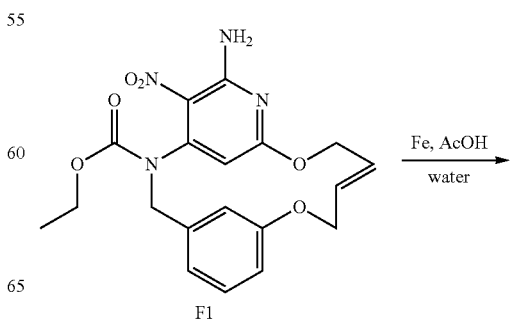

-continued

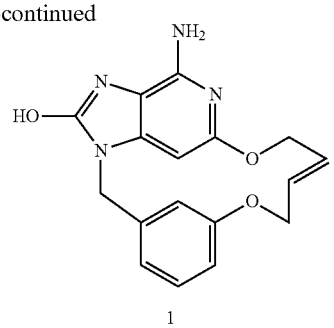

1

Synthesis of Final Compound 1

A mixture of F1 (570 mg; 1.42 mmol) and iron (795 mg; 14.2 mmol) in AcOH (21 mL) and water (4.2 mL) was stirred at 50° C. for 2 h. The mixture was concentrated until dryness. DMF was added, the mixture was sonicated, heated and filtered through a pad of celite and the celite was rinsed with hot DMF. An iron scavenger (SiliaBond Imidazole from SiliCycle) (25.4 g; 29.5 mmol) was added to the filtrate and the mixture was stirred at rt for 16 h. The mixture was filtered through celite, the celite was rinsed with DMF and the filtrate was concentrated in vacuo to give 620 mg of a brown solid. The crude was purified by preparative LC (irregular SiOH, 15-40 µm, 30 g Merck, mobile phase gradient: from $CH_2Cl_2$/MeOH/$NH_3$aq 98/2/0.2 to 85/15/1.5) to give 360 mg of final compound 1 as an off-white solid (75% yield).

Alternative Synthesis of Intermediate C1

At 0° C., diisopropylazodicarboxylate (DIAD) (3.0 mL, 15.0 mmol) was added drop wise to a mixture of A1 (3.70 g, 10.028 mmol), G1 (1.98 g, 12.0 mmol) and $PPh_3$ (3.94 g, 15.0 mmol) in THF (70 mL). The mixture was stirred at rt for 12 h. EtOAc and water were added. The layers were decanted. The organic layer was washed with water, dried over $MgSO_4$, filtered and the solvent was evaporated. The crude was purified by preparative LC on (Irregular SiOH 20-45 µm 450 g Matrex), mobile phase (85% Heptane, 15% AcOEt) to give 4.5 g of intermediate C1 (87% yield).

Overall Scheme in the Preparation of Final Products: Method 2

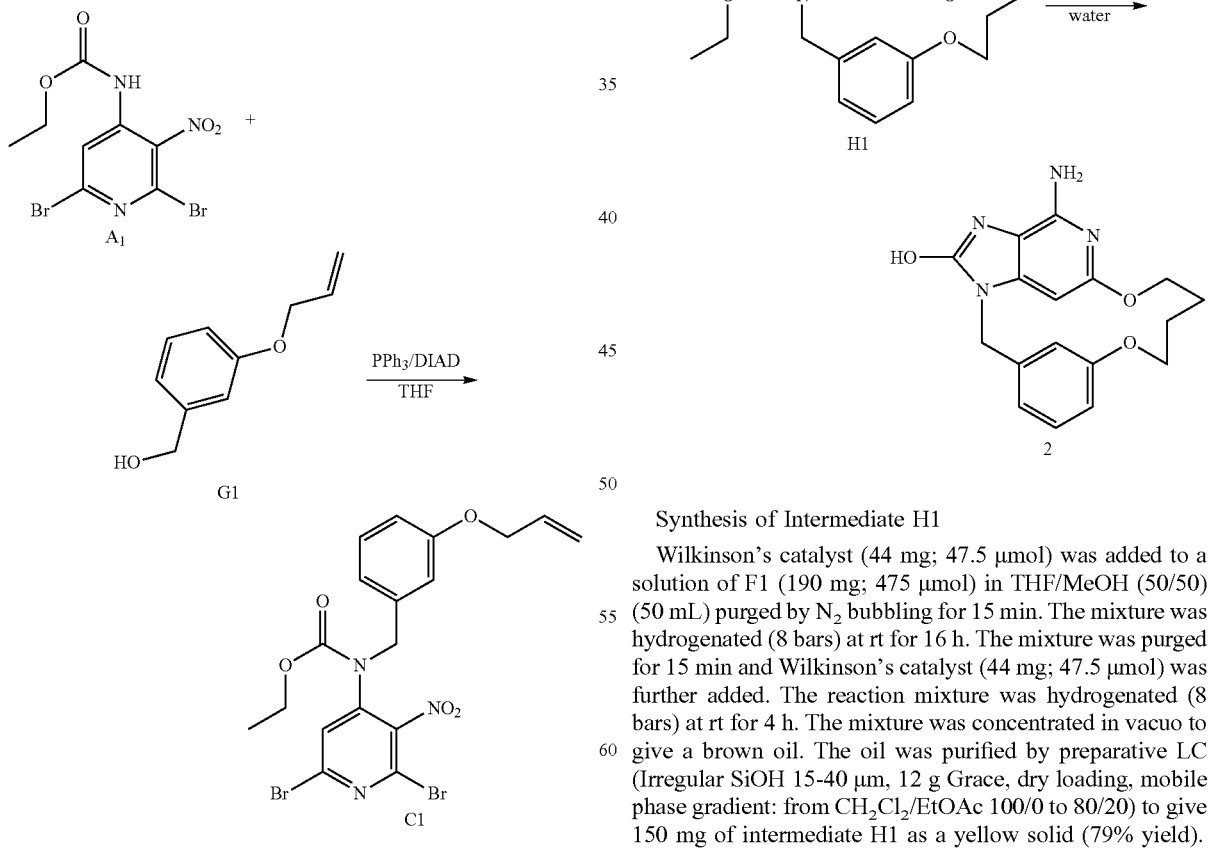

Synthesis of Intermediate H1

Wilkinson's catalyst (44 mg; 47.5 µmol) was added to a solution of F1 (190 mg; 475 µmol) in THF/MeOH (50/50) (50 mL) purged by $N_2$ bubbling for 15 min. The mixture was hydrogenated (8 bars) at rt for 16 h. The mixture was purged for 15 min and Wilkinson's catalyst (44 mg; 47.5 µmol) was further added. The reaction mixture was hydrogenated (8 bars) at rt for 4 h. The mixture was concentrated in vacuo to give a brown oil. The oil was purified by preparative LC (Irregular SiOH 15-40 µm, 12 g Grace, dry loading, mobile phase gradient: from $CH_2Cl_2$/EtOAc 100/0 to 80/20) to give 150 mg of intermediate H1 as a yellow solid (79% yield).

Synthesis of Final Compound 2

Compound 2 was obtained using the procedure to prepare compound 1 (54 mg, 44% yield).

Overall Scheme in the Preparation of Final Products: Method 3

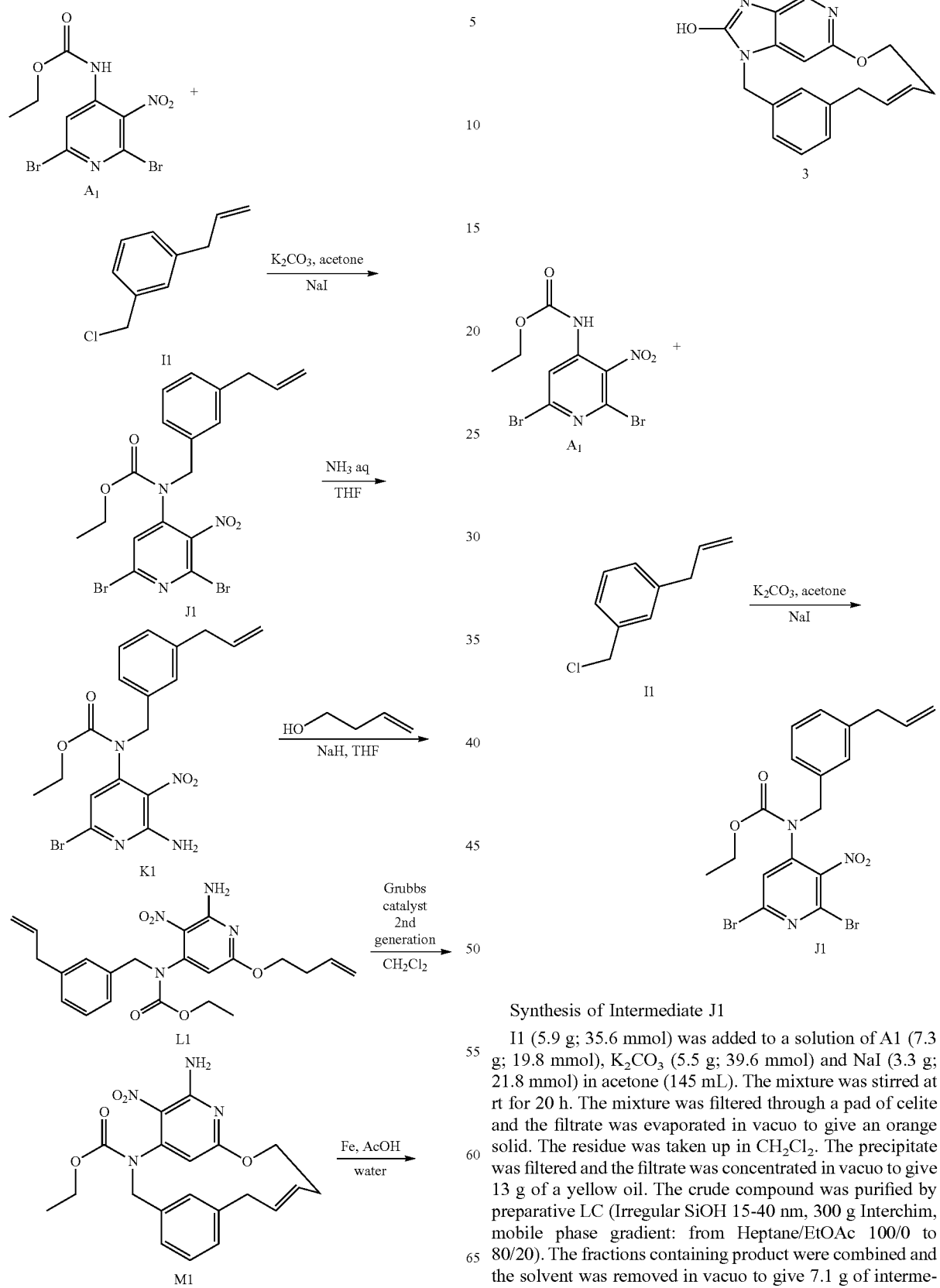
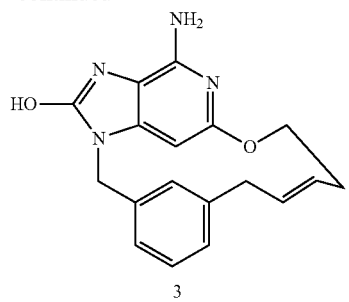

Synthesis of Intermediate J1

I1 (5.9 g; 35.6 mmol) was added to a solution of A1 (7.3 g; 19.8 mmol), K₂CO₃ (5.5 g; 39.6 mmol) and NaI (3.3 g; 21.8 mmol) in acetone (145 mL). The mixture was stirred at rt for 20 h. The mixture was filtered through a pad of celite and the filtrate was evaporated in vacuo to give an orange solid. The residue was taken up in CH₂Cl₂. The precipitate was filtered and the filtrate was concentrated in vacuo to give 13 g of a yellow oil. The crude compound was purified by preparative LC (Irregular SiOH 15-40 nm, 300 g Interchim, mobile phase gradient: from Heptane/EtOAc 100/0 to 80/20). The fractions containing product were combined and the solvent was removed in vacuo to give 7.1 g of intermediate J1 (72% yield) as a yellow oil.

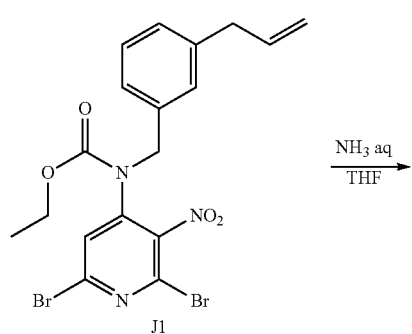

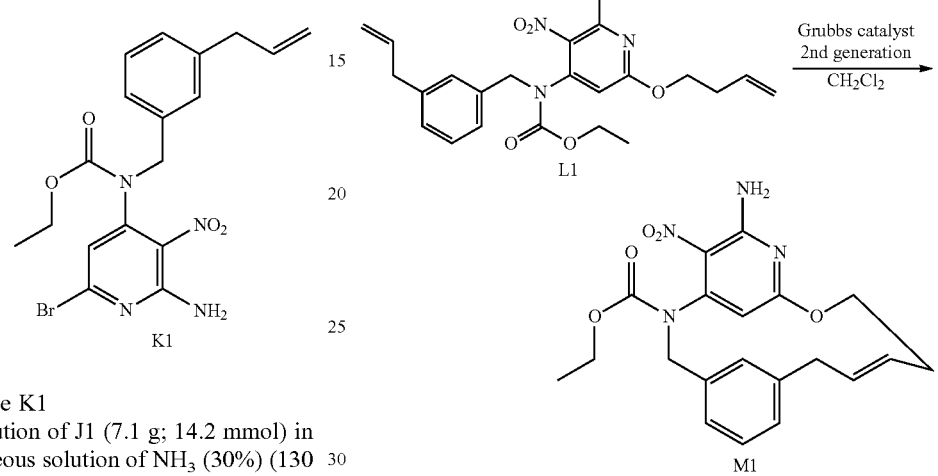

Synthesis of Intermediate K1

In a schlenk flask, a solution of J1 (7.1 g; 14.2 mmol) in THF (130 mL) and an aqueous solution of NH$_3$ (30%) (130 mL) was stirred at rt for 16 h. The mixture was taken up with EtOAc and a saturated water solution of NaCl, layers were separated. The organic layer was dried over MgSO$_4$, filtered and concentrated in vacuo to give 6.4 g of a yellow oil (100% yield).

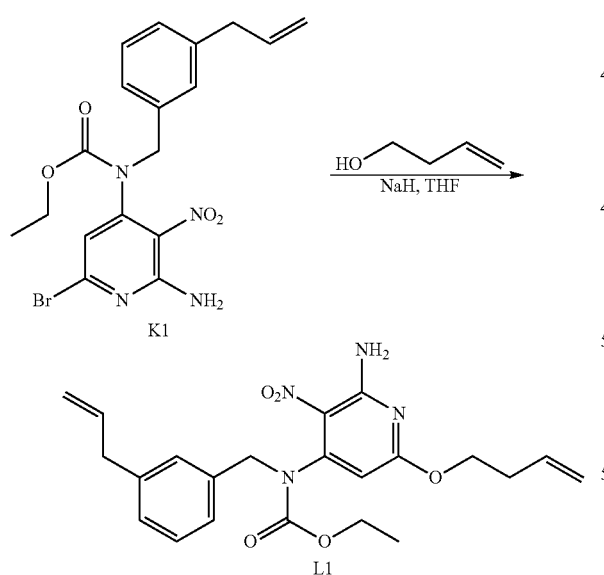

Synthesis of Intermediate L1

NaH (2.2 g; 54.2 mmol) was added portion wise at rt and under N$_2$ atmosphere to 3-buten-1-ol (76 mL). The mixture was stirred at rt for 30 min before being added drop wise at 0° C. to a solution of K1 (5.9 g; 13.6 mmol) in THF (150 mL). The resulting mixture was stirred at 0° C. for 1 h. The mixture was poured into an aqueous saturated NH$_4$Cl solution. EtOAc and satured aqueous NaCl solution were added, the layers were separated. The organic layers was dried over MgSO$_4$, filtered and concentrated in vacuo to give a yellow residue which was azeotropically distilled with toluene (once) to give 6.6 g of a yellow oil. The crude compound was purified by preparative LC (Irregular SiOH 15-40 µm, 220 g Grace, mobile phase gradient: from Heptane/EtOAc 100/0 to 50/50). The fractions containing product were combined and the solvent was removed in vacuo to give 4.46 g of intermediate L1 (77% yield) as a yellow oil.

Synthesis of Intermediate M1

The reaction was performed in 2 batches.

Typical procedure for one batch:

A solution of L1 (2.45 g; 5.75 mmol) in dry CH$_2$Cl$_2$ (1.7 L) was degassed by N$_2$ bubbling for 15 min. Grubbs catalyst 2$^{nd}$ generation (488 mg; 574 µmol) was added and the mixture was stirred at rt for 72 h. SiliaBond DMT (7.66 g; 4.59 mmol) was added and the mixture was stirred at rt for 16 h. The 2 batches were combined and filtered through celite. The filtrate was concentrated in vacuo to give a black solid. The crude compound was purified by preparative LC (Irregular SiOH 15-40 µm, 150 g Merck, mobile phase gradient: from Heptane/EtOAc 100/0 to 50/50). The fractions containing product were combined and the solvent was removed in vacuo to give 230 mg of fraction 1 and 2.3 g of fraction 2. Fraction 2 was re-purified by preparative LC (Stationary phase: irregular SiOH 40 µm 120 g, mobile phase: Heptane/CH$_2$Cl$_2$/MeOH 55/43/2). The isolated compound was combined with fraction 1 and purified by achiral SFC (Stationary phase: Chiralpak IC 5 µm 250×20 mm, mobile phase: 70% CO$_2$, 30% iPrOH) to give 1.51 g of intermediate M1 (33% yield, isomer E) as a yellow solid.

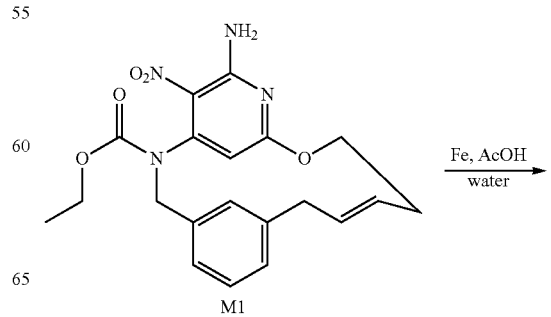

-continued

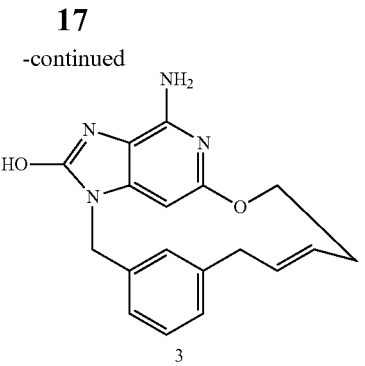

3

Synthesis of Final Compound 3

Iron (631 mg; 11.3 mmol) was added to a solution of M1 (750 mg; 1.88 mmol) in AcOH (150 mL) and water (25 mL). The mixture was stirred at 80° C. for 16 h. Iron (315 mg; 5.65 mmol) was added and the mixture was stirred at 80° C. for 2 h. Iron (315 mg; 5.65 mmol) was added and the mixture was stirred at 80° C. for 4 h. Iron (315 mg; 5.65 mmol) was added and the mixture was stirred at 80° C. for 16 h. The mixture was concentrated until dryness. DMF was added, the mixture was filtered through celite and the celite was rinsed with hot DMF. SiliaBond imidazole (48.7 g; 56.5 mmol) was added to the filtrate and the mixture was stirred at rt for 16 h. The mixture was filtered through celite, the celite was rinsed with DMF and the filtrate was concentrated in vacuo. The crude compound was purified by preparative LC (irregular SiOH, 15-40 µm, 25 g Merck, mobile phase gradient: from $CH_2Cl_2$/MeOH/$NH_3$aq 98/2/0.2 to 85/15/1.5) to give 2 fractions. Fraction 1 was taken-up with EtOH and filtered to give fraction 3 and fraction 2 was taken-up with MeCN and filtered to give fraction 4. Fractions 3 and 4 were combined in EtOH, filtered and dried in vacuo to give 199 mg of final compound 3 (33% yield).

Overall Scheme in the Preparation of Final Products: Method 4

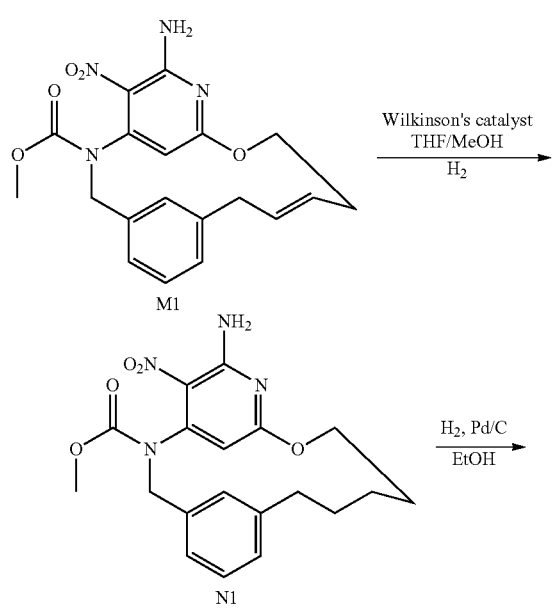

-continued

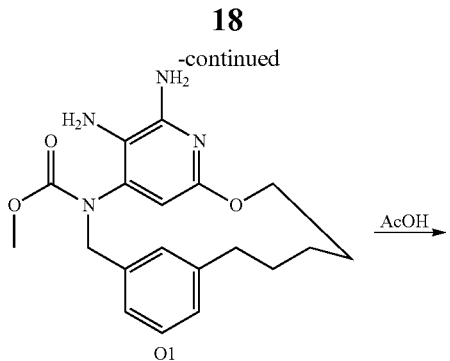

Synthesis of Intermediate N1

Wilkinson's catalyst (46 mg; 50.2 µmol) was added to a solution of M1 (200 mg; 502 µmol) in THF/MeOH (50/50) (50 mL) purged by $N_2$ bubbling for 15 min. The mixture was hydrogenated (7 bars) at rt for 20 h. The mixture was purged by $N_2$ bubbling for 15 min, further Wilkinson's catalyst (46 mg; 50.2 µmol) was added and the reaction mixture was hydrogenated (7 bars) at rt for 16 h. The reaction mixture was concentrated in vacuo to give a green oil. The oil was purified by preparative LC (Irregular SiOH 15-40 nm, 25 g Merck, dry loading, mobile phase gradient: from Heptane/EtOAc 100/0 to 70/30) to give 130 mg of intermediate N1 as a yellow solid (66% yield).

Synthesis of Intermediate O1

In a pressure vessel reactor, N1 (110 mg; 275 µmol) was hydrogenated in EtOH (5 mL) with Pd/C (10%) (30 mg; 28.5 µmol) as catalyst at 40° C. (3 bars) for 6 h. The catalyst was removed by filtration over celite, the celite was washed with EtOH and the filtrate was evaporated under vacuum to give 100 mg of a yellow residue (98% yield). Intermediate O1 was used in the next step without further purification.

Synthesis of Final Compound 4

In a sealed tube, O1 (100 mg; 270 µmol) in pure acetic acid (5 mL) was stirred at rt for 90 min. The solvent was removed under reduced pressure to give a yellow residue. The residue was taken up with $CH_2Cl_2$ and the solvent was removed under reduced pressure (twice) to give 87 mg of a yellow-green solid. The solid was azeotropically distilled with toluene (four times), and was then triturated and sonicated in $Et_2O$. The mixture was filtered off (glass frit n° 5) to give 75 mg of final compound 4 (77% yield, acetate salt).

Overall Scheme in the Preparation of Final Products: Method 5

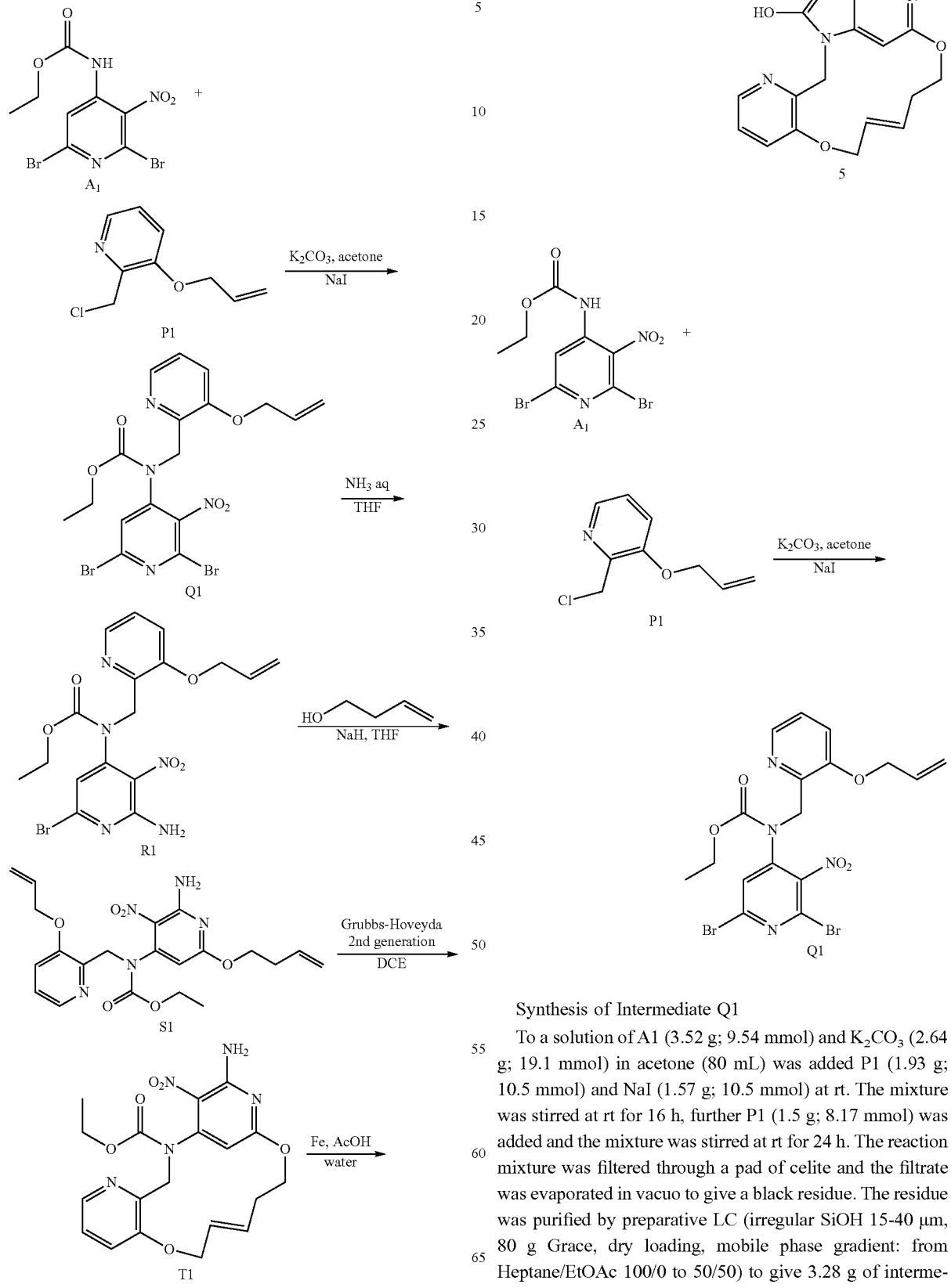

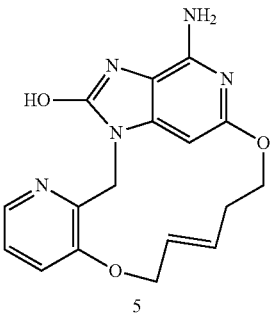

Synthesis of Intermediate Q1

To a solution of A1 (3.52 g; 9.54 mmol) and $K_2CO_3$ (2.64 g; 19.1 mmol) in acetone (80 mL) was added P1 (1.93 g; 10.5 mmol) and NaI (1.57 g; 10.5 mmol) at rt. The mixture was stirred at rt for 16 h, further P1 (1.5 g; 8.17 mmol) was added and the mixture was stirred at rt for 24 h. The reaction mixture was filtered through a pad of celite and the filtrate was evaporated in vacuo to give a black residue. The residue was purified by preparative LC (irregular SiOH 15-40 μm, 80 g Grace, dry loading, mobile phase gradient: from Heptane/EtOAc 100/0 to 50/50) to give 3.28 g of intermediate Q1 as an orange oil (67% yield).

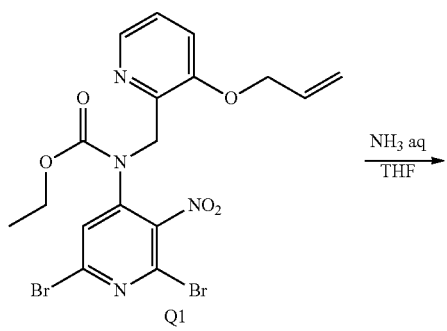

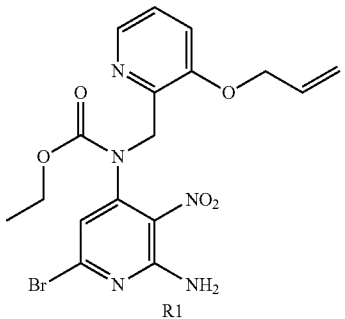

a solution of R1 (2.74 g; 5.63 mmol) in THF (62 mL) at 0° C. The resulting mixture was stirred at rt for 1 h and was poured in NH$_4$Cl saturated aqueous solution. EtOAc and NaCl saturated aqueous solution were added, the layers were separated and the aqueous layer was extracted with EtOAc (once). The combined organic layers were dried over MgSO$_4$, filtered and the solvent was removed under reduced pressure to give a yellow oil. The oil was purified by preparative LC (Irregular SiOH 15-40 nm, 80 g Grace, dry loading, mobile phase gradient: from Heptane/EtOAc 100/0 to 20/80) to give 1.06 g of intermediate S1 as a yellow residue (42% yield).

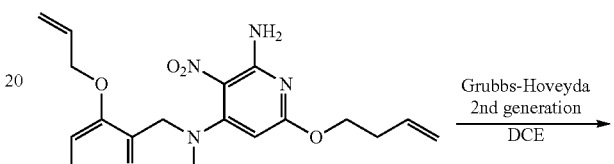

Synthesis of Intermediate R1

In a schlenk flask, to a solution of Q1 (3.28 g; 6.36 mmol) in THF (52 mL), was added an aqueous solution of NH$_3$ (30%) (52 mL) at rt. The mixture was stirred at rt for 26 h and further aqueous solution of NH$_3$ (10 mL) was added and the mixture was stirred at rt for 4 h. The mixture was taken up with EtOAc and saturated aqueous solution of NaCl, the layers were separated and the organic layer was dried over MgSO$_4$, filtered and the solvent was removed under reduced pressure to give 2.74 g of intermediate R1 as a yellow oil (87% yield).

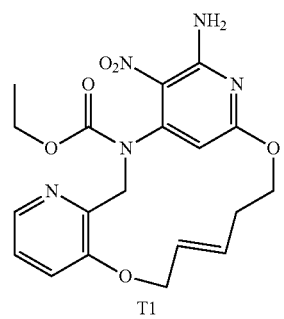

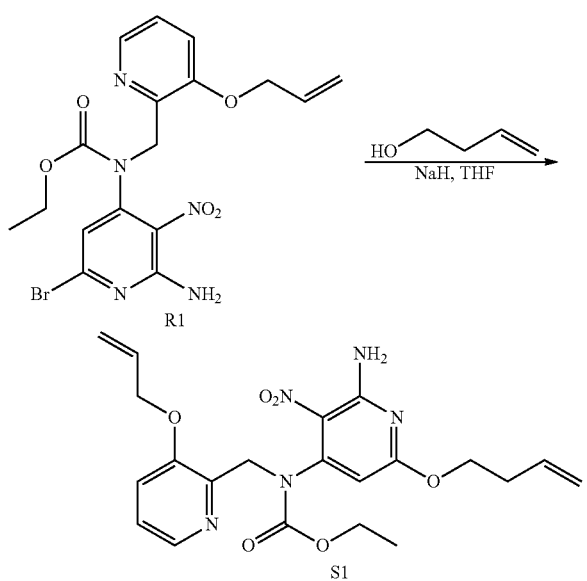

Synthesis of Intermediate S1

NaH (60% in oil) (888 mg; 22.2 mmol) was added portion wise to 3-buten-1-ol (30 mL; 354 mmol) at rt. The mixture was stirred at rt for 30 min before being added drop wise to

Synthesis of Intermediate T1

The reaction was performed in two batches of 480 mg of intermediate S1.

Herein is reported the procedure for one batch:

In a schlenck flask, a solution of S1 (480 mg; 1.08 mmol) and chlorodicyclohexylborane (1M in hexane) (216 µL; 216 µmol) in dry dichloroethane (300 mL) was stirred at 80° C. and under N$_2$ atmosphere for 1 h. Grubbs-Hoveyda catalyst $2^{nd}$ generation (68 mg; 108 µmol) was added and the mixture was stirred at 120° C. for 2 h.

The two batches were mixed, SiliaBond DMT (2.84 g; 1.73 mmol) was added and the mixture was stirred at rt for 20 h.

The mixture was filtered through a pad of celite, the celite was washed with EtOAc and the filtrate was evaporated in vacuo to give a brown solid. The brown solid was purified by preparative LC (Irregular SiOH 15-40 µm, 40 g Grace, dry loading, mobile phase gradient: CH$_2$Cl$_2$/EtOAc from 100/0 to 20/80) to give 610 mg of a yellow residue (mixture of E and Z isomers, intermediate U1). 310 mg of intermediate U1 was purified by Reverse phase (Stationary phase: Nucleodur-Sphinx rp 5 µm 21×150 mm, mobile phase: Gradient from 70% formic acid 0.1%, 30% MeCN to 0% formic acid 0.1%, 100% MeCN) to give 195 mg of intermediate T1 (E isomer) as a yellow solid (22% yield).

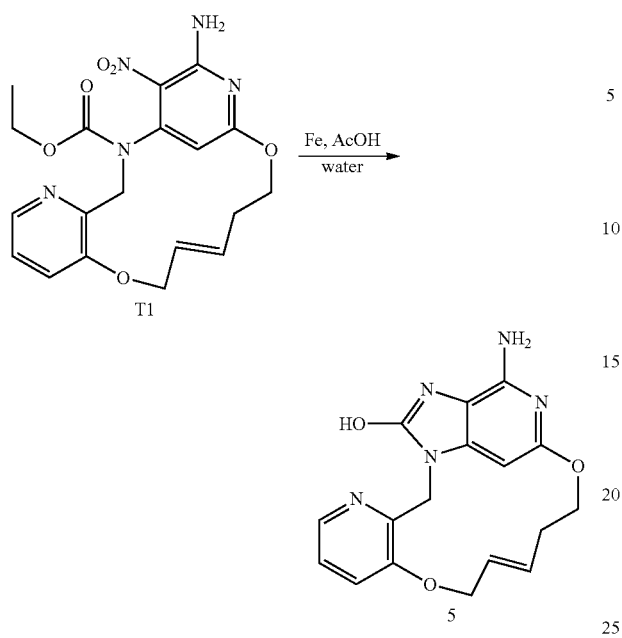

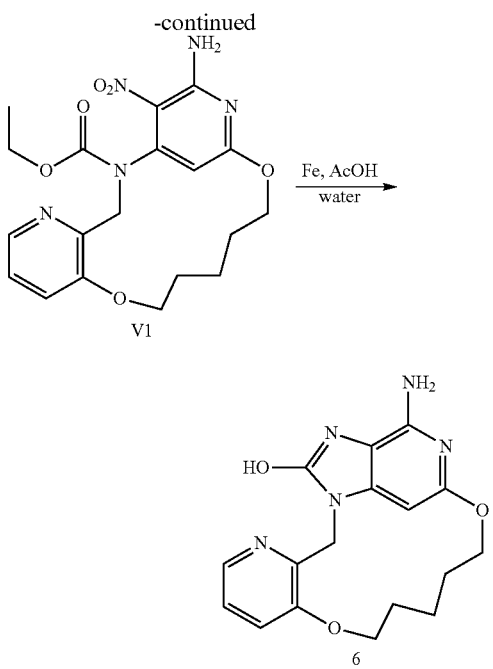

Synthesis of Final Compound 5

A mixture of T1 (160 mg; 385 µmol) and iron (129 mg; 2.31 mmol) in acetic acid (21 mL) and water (2.4 mL) was stirred at 80° C. for 7 h. Further iron (129 mg; 2.31 mmol) was added and the mixture was stirred at 80° C. for 16 h. Further iron (129 mg; 2.31 mmol) was added and the mixture was stirred at 80° C. for 3 h. The mixture was concentrated in vacuo to give a residue. The residue was diluted in DMF and filtered through a pad of celite. Sili-aBond imidazole (12.7 g; 14.7 mmol) was added to the filtrate and the mixture was stirred at rt for 16 h. The mixture was filtered through a pad of celite and the filtrate was evaporated in vacuo to give a brown solid. The brown solid was purified by preparative LC (irregular SiOH 15-40 µm, 12 g Grace, dry loading, mobile phase gradient: from $CH_2Cl_2$/MeOH/$NH_3$aq 97/3/0.3 to 80/20/2) to give 65 mg of an off-white solid. The solid was purified by Reverse phase (Stationary phase: X-Bridge-C18 5 µm 30*150 mm, mobile phase gradient: from $H_2O$ (0.5% $NH_4CO_3$)/MeOH 70/30 to 0/100) to give 43 mg of final compound 5 as a white solid (31% yield, E isomer).

Overall Scheme in the Preparation of Final Products: Method 6

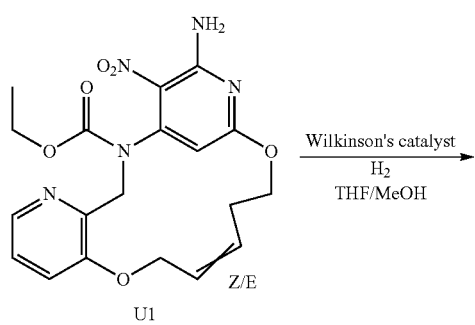

Synthesis of Intermediate V1

Wilkinson's catalyst (58 mg; 62.6 µmol) was added to a solution of U1 (Z/E mixture, 260 mg; 626 µmol) in THF/MeOH (50/50) (66 mL) purged by $N_2$ bubbling for 15 min. The mixture was hydrogenated (7 bars) at rt for 16 h. Further Wilkinson's catalyst (58 mg; 62.6 µmol) was added and the mixture was hydrogenated (7 bars) at rt for 6 h. The reaction mixture was concentrated in vacuo to give a brown solid. The solid was purified by preparative LC (Irregular SiOH 15-40 µm, 25 g Merck, dry loading, mobile phase gradient: from Heptane/EtOAc 100/0 to 50/50) to give 250 mg of intermediate V1 as a yellow oil (54% yield).

Synthesis of Final Compound 6

A mixture of V1 (238 mg; 359 µmol) and iron (120 mg; 2.16 mmol) in acetic acid (20 mL) and water (2.2 mL) was stirred at 80° C. for 6 h. Further iron (120 mg; 2.16 mmol) was added and the mixture was stirred at 80° C. for 20 h. Further iron (120 mg; 2.16 mmol) was added and the mixture was stirred at 80° C. for 5 h. The mixture was concentrated in vacuo to give a residue. The residue was diluted in DMF and filtered through a pad of celite. Sili-aBond imidazole (11.1 g; 12.9 mmol) was added to the filtrate and the mixture was stirred at rt for 16 h. The mixture was filtered through a pad of celite and the filtrate was evaporated in vacuo to give a brown solid. The solid was purified by preparative LC (irregular SiOH 15-40 µm, 12 g Grace, dry loading, mobile phase gradient: from $CH_2Cl_2$/MeOH/$NH_3$aq 97/3/0.3 to 80/20/2) to give 32 mg of an off-white solid. The solid was taken up with water, triturated and sonicated. The resulting suspension was filtered off (glass frit n° 5) and washed with $Et_2O$ (twice) to give 19 mg of final compound 6 as an off-white solid (15% yield).

Overall Scheme in the Preparation of Final Products: Method 7

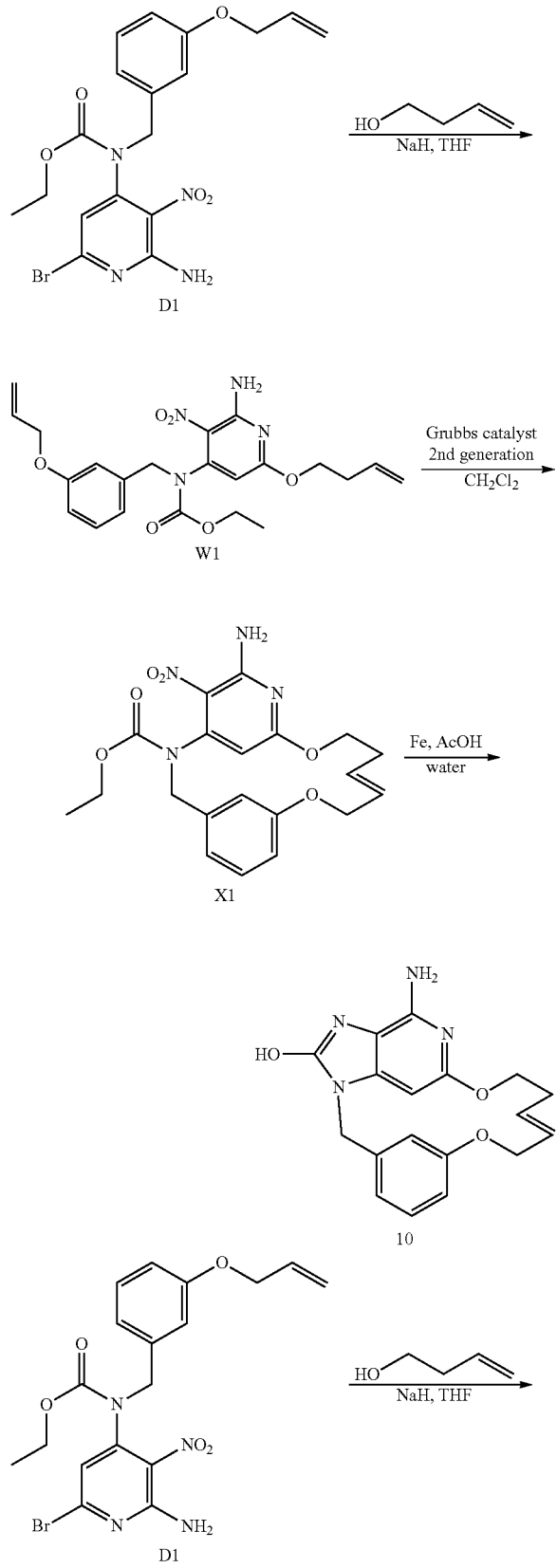

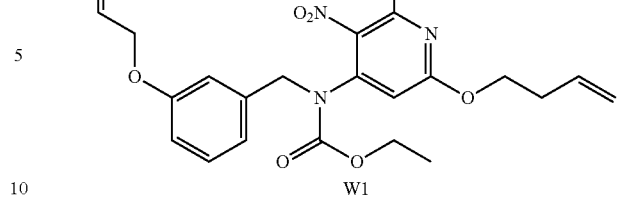

Synthesis of Intermediate W1

NaH (60% in oil) (2.1 g; 52.1 mmol) was added portion wise to 3-buten-1-ol (74 mL) at rt. The mixture was stirred at rt for 30 min before being added drop wise to a solution of D1 (5.97 g; 13.2 mmol) in THF (150 mL) at 0° C. The resulting mixture was then stirred at rt for 2 h 30 min and was poured in aqueous saturated solution of $NH_4Cl$. EtOAc and saturated aqueous solution of NaCl were added, the layers were separated and the aqueous layer was extracted with EtOAc (once). The combined organic layers were dried over $MgSO_4$, filtered and the solvent was removed under reduced pressure to give 6.77 g of a yellow oil. The crude was purified by preparative LC (Irregular SiOH 15-40 µm, 120 g Grace, liquid injection, mobile phase gradient: from Heptane/EtOAc 100/0 to 50/50) to give 5.12 g of intermediate W1 as a yellow oil (83% yield).

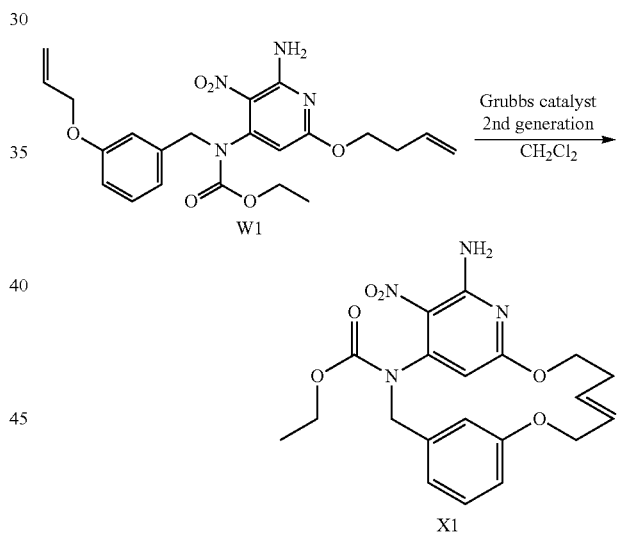

Synthesis of Intermediate X1

To a solution of W1 (3 g; 6.78 mmol) in $CH_2Cl_2$ (1.3 L) degassed by $N_2$ bubbling for 15 min was added Grubbs catalyst $2^{nd}$ generation (578 mg; 678 µmol) at rt. The solution was stirred at rt for 20 h. SiliaBond DMT (8.89 g; 5.42 mmol) was added and the mixture was stirred at rt for 20 h. The reaction mixture was filtered through a pad of celite and the solvent was removed under reduced pressure to give a brown residue, which was combined with another batch (0.226 mmol scale). The combined residue was taken up with MeOH, sonicated and heated to give a precipitate which was filtered off to give 3.2 g of a brown solid. The crude was purified by preparative LC (irregular SiOH, 15-40 µm, 220 g grace, liquid injection, mobile phase gradient: from $CH_2Cl_2$/EtOAc 100/0 to 50/50) to give 1.7 g of fraction 1 as a pale brown solid. Fraction 1 was taken up with MeOH, sonicated and heated to give a precipitate which was filtered off to give 820 mg of fraction 2 as a pale brown solid.

The filtrate was concentrated in vacuo to give 590 mg of fraction 3 as a brown residue (impure X1). Fraction 2 was purified by preparative LC (Stationary phase: Spherical bare silica 5 μm 150×30.0 mm, mobile phase gradient: from Heptane/EtOAc 85/15 to 0/100) to give 435 mg of intermediate X1 as a yellow solid (E isomer, 15% yield).

Fraction 3 was Purified with Another Batch.

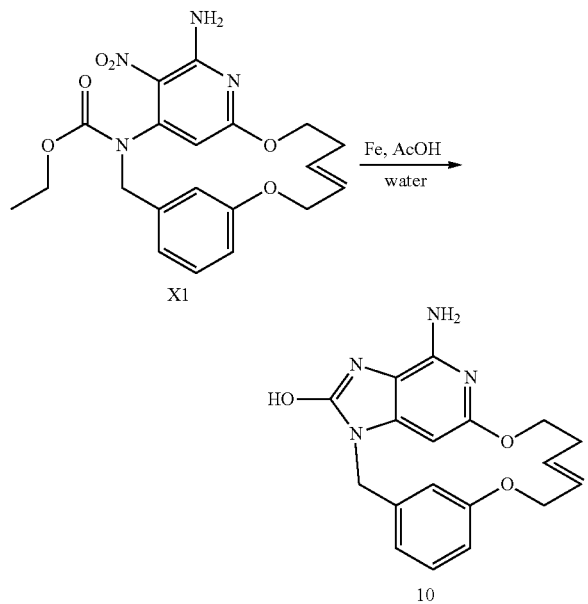

Synthesis of Final Compound 10

A mixture of X1 (430 mg; 1.04 mmol) and iron (579 mg; 10.4 mmol) in acetic acid (43 mL) and water (3 mL) was stirred at 50° C. for 4 h. The mixture was concentrated until dryness. DMF was added. The mixture was sonicated, heated and filtered through a pad of celite and the celite was rinsed with hot DMF. SiliaBond imidazole (17.9 g; 20.8 mmol) was added to the filtrate and the mixture was stirred at rt for 16 h. The mixture was filtered through celite, the celite was rinsed with DMF and the filtrate was concentrated in vacuo to give 670 mg of crude compound. The crude was purified by preparative LC (irregular SiOH, 15-40 μm, 25 g Merck, mobile phase gradient: from $CH_2Cl_2$/MeOH/$NH_3$aq 98/2/0.2 to 85/15/1.5) to give an off-white solid. The solid was dried at 40° C. under reduced pressure during 20 h to give 295 mg of final compound 10 as an off-white solid (84% yield).

Overall Scheme in the Preparation of Final Products: Method 8

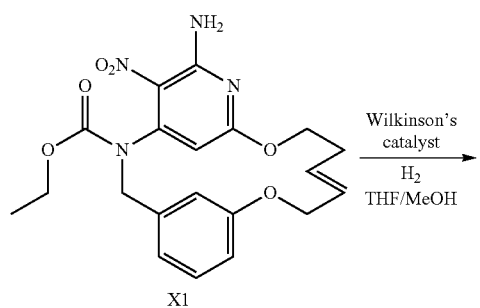

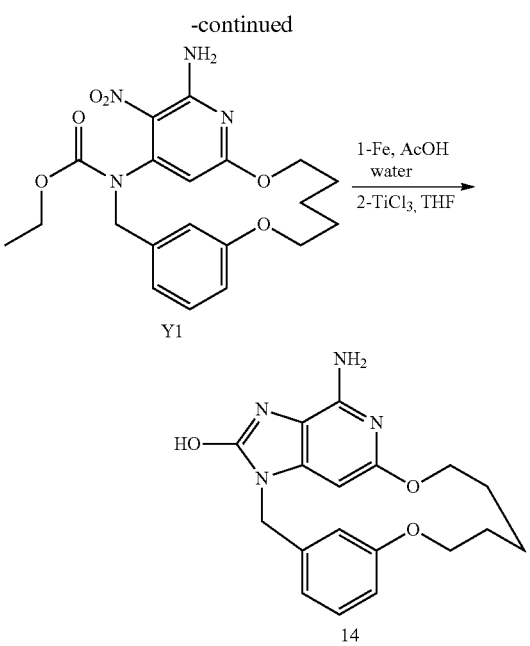

Synthesis of Intermediate Y1

Wilkinson's catalyst (103 mg; 111 μmol) was added to a solution of X1 (230 mg; 0.555 mmol) in THF/MeOH (50/50) (40 mL) purged by $N_2$ bubbling for 15 min. The mixture was hydrogenated (8 bars) at rt for 24 h. The reaction mixture was concentrated in vacuo to give a brown residue. The solid was purified by preparative LC (irregular SiOH, 15-40 μm, 12 g Grace, dry loading, mobile phase gradient: from $CH_2Cl_2$/EtOAc 100/0 to 90/10) to give 55 mg of intermediate Y1 as a yellow residue (24% yield).

Synthesis of Final Compound 14

A mixture of Y1 (55 mg; 0.132 mmol) and iron (74 mg; 1.32 mmol) in acetic acid (5.5 mL) and water (0.4 mL) was stirred at 50° C. for 20 h. More iron (37 mg; 0.66 mmol) was added and the mixture was stirred at 50° C. for 3 h. More iron (37 mg; 0.66 mmol) was added and the mixture was stirred at 50° C. for 20 h. The mixture was filtered through a pad of celite and the celite was rinsed with acetic acid. More iron (74 mg; 1.32 mmol) was added to the filtrate and the mixture was stirred at 50° C. for 88 h. More iron (74 mg; 1.32 mmol) was added to the filtrate and the mixture was stirred at 80° C. for 24 h. The cyclisation was not complete. The mixture was concentrated in vacuo to give a brown solid.

$TiCl_3$ (8.60 mL; 10.0 mmol) was added drop wise to a solution of the brown solid in C (19 mL). The mixture was stirred at rt overnight. The mixture was basified by addition of $K_2CO_3$ powder at 0° C. The resulting mixture was filtered through a pad of celite and the celite was washed with a solution of AcOEt/MeOH (8:2). The filtrate was concentrated in vacuo. The crude solid was purified by preparative LC (irregular SiOH, 15-40 μm, 10 g Merck, dry loading, mobile phase gradient: from $CH_2Cl_2$/MeOH/$NH_3$aq 98/2/0.2 to 85/15/1.5). The fractions containing product were combined and the solvent was removed in vacuo to give 20 mg of final compound 14 (12% yield) as an off-white solid.

Overall Scheme in the Preparation of Final Products: Method 9

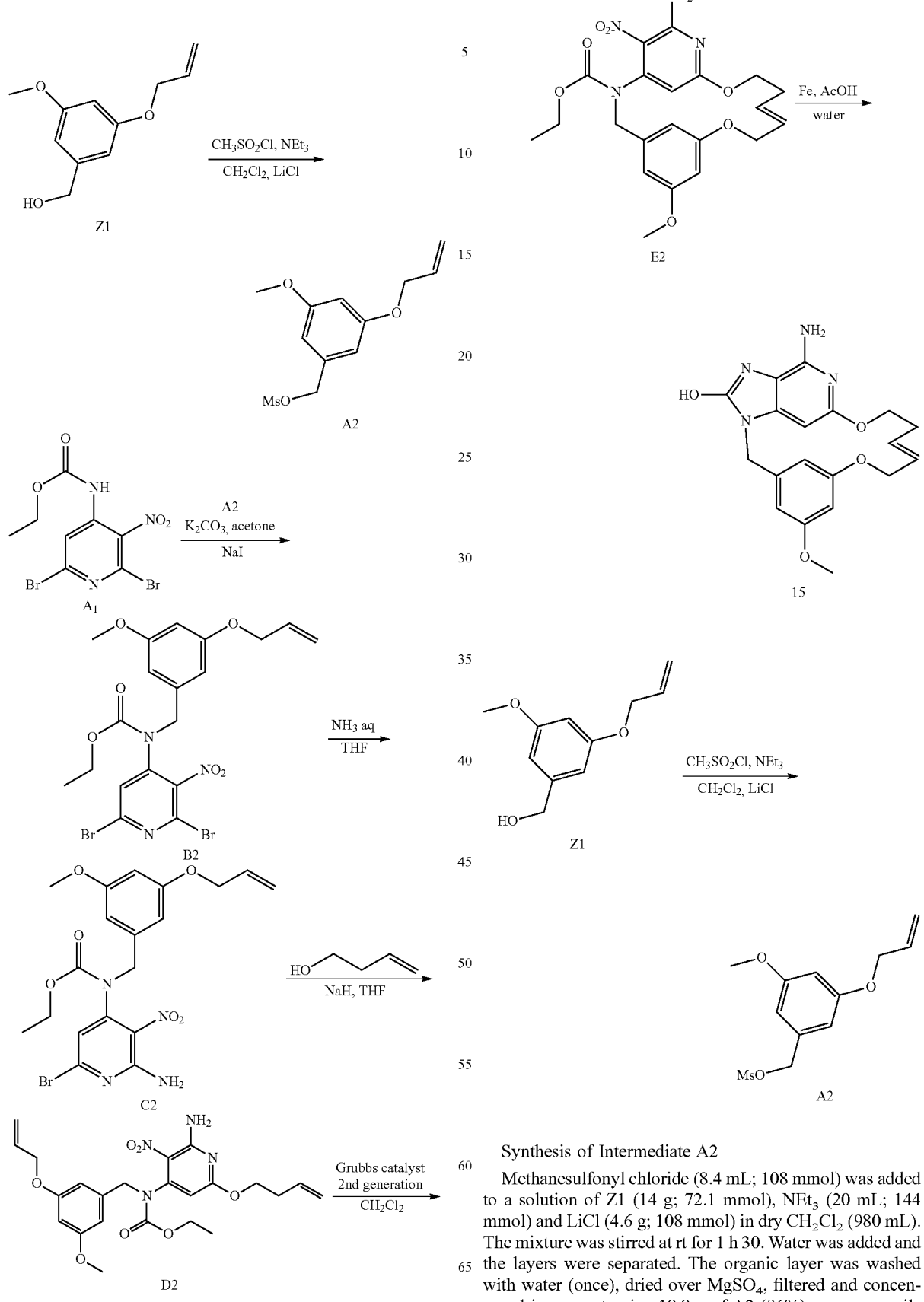

Synthesis of Intermediate A2

Methanesulfonyl chloride (8.4 mL; 108 mmol) was added to a solution of Z1 (14 g; 72.1 mmol), $NEt_3$ (20 mL; 144 mmol) and LiCl (4.6 g; 108 mmol) in dry $CH_2Cl_2$ (980 mL). The mixture was stirred at rt for 1 h 30. Water was added and the layers were separated. The organic layer was washed with water (once), dried over $MgSO_4$, filtered and concentrated in vacuo to give 18.8 g of A2 (96%) as a green oil.

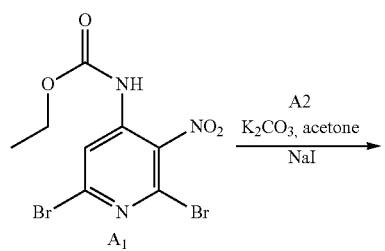

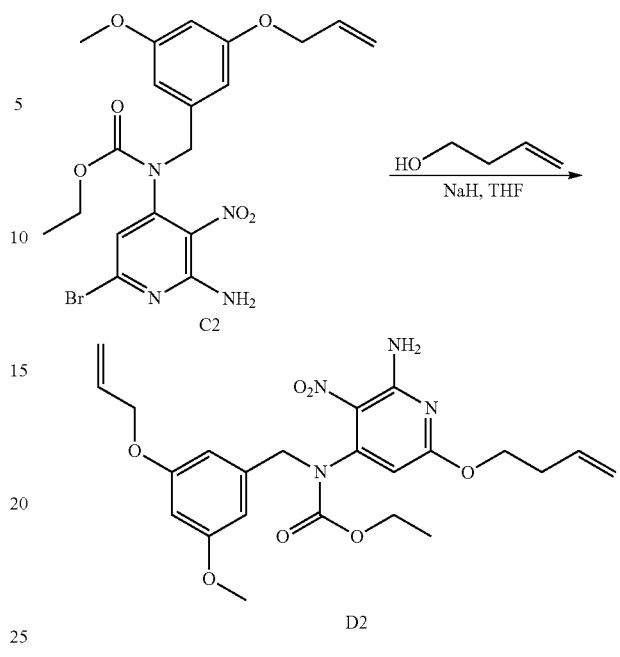

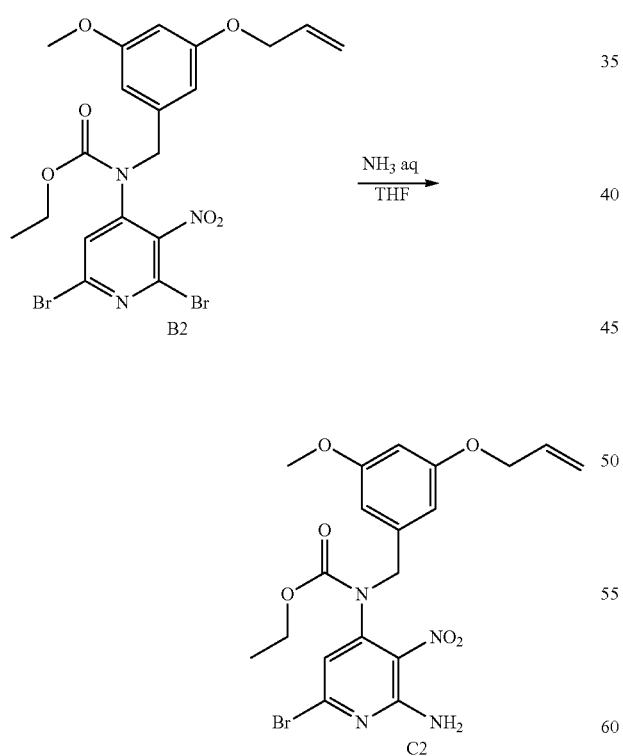

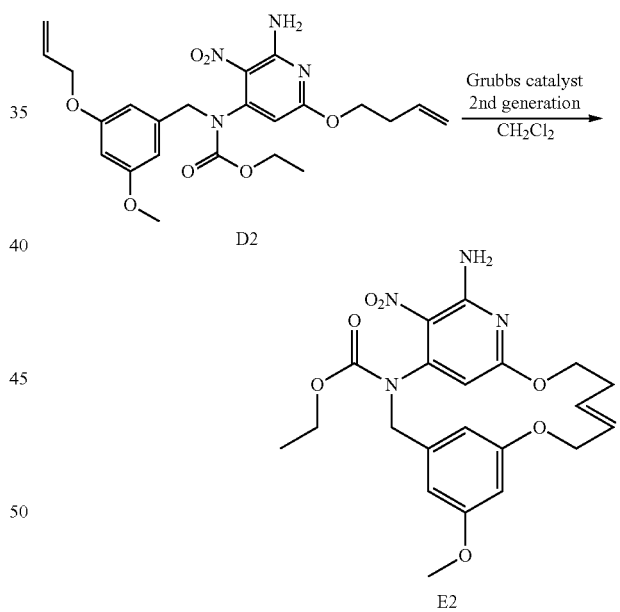

Synthesis of Intermediate B2

Intermediate B2 was obtained using the procedure described for intermediate C1 (78% yield as a yellow oil).

Synthesis of Intermediate C2

Intermediate C2 was obtained using the procedure described for intermediate D1 (quantitative yield as a yellow oil).

Synthesis of Intermediate D2

Intermediate D2 was obtained using the procedure described for intermediate W1 (64% yield as a yellow solid).

Synthesis of Intermediate E2

A solution of D2 (1 g; 2.12 mmol) in $CH_2Cl_2$ (400 mL) was degassed by $N_2$ bubbling for 15 min. Grubbs catalyst $2^{nd}$ generation (181 mg; 212 µmol) was added and the mixture was stirred at rt for 16 h. SiliaBond DMT (2.78 g; 1.69 mmol) was added and the mixture was stirred at rt for 16 h. The mixture was filtered through a pad of celite and the filtrate was concentrated in vacuo to give 1.11 g of a brown oil. The crude was purified by preparative LC (Irregular SiOH 15-40 µm, 50 g Merck, mobile phase gradient: from $CH_2Cl_2$/EtOAc 100/0 to 90/10). The fractions containing product were combined and the solvent was removed in vacuo to give 386 mg of intermediate E2 (41%, isomer E (96.2%)+isomer Z (3.8%)) as a yellow foam.

Overall Scheme in the Preparation of Final Products: Method 10

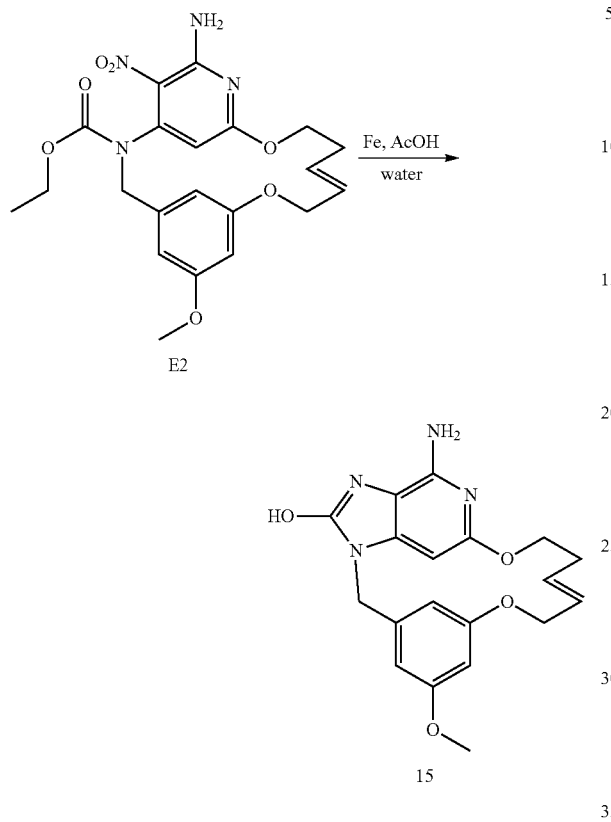

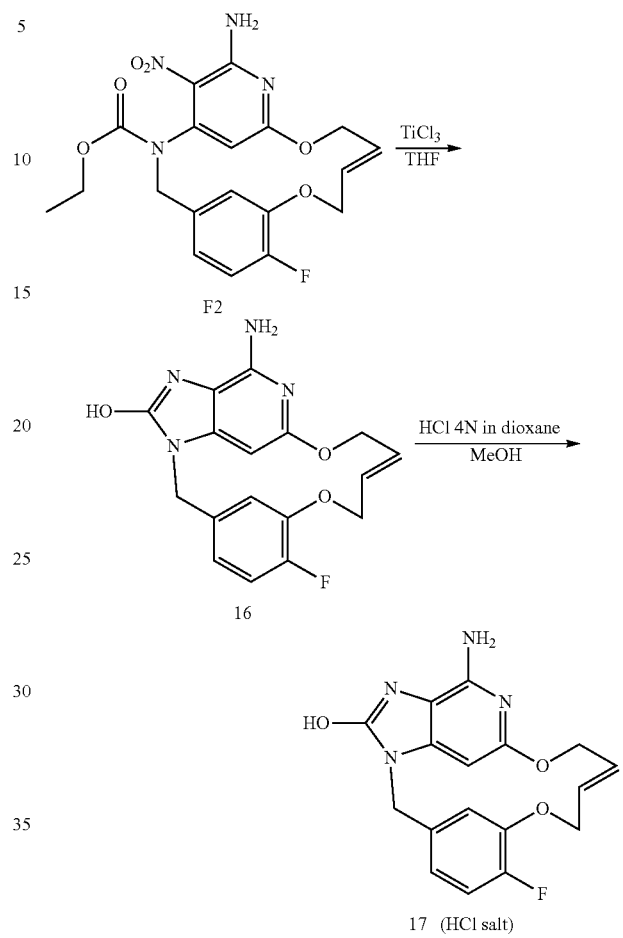

Synthesis of Final Compound 15

Iron (291 mg; 5.21 mmol) was added to a solution of E2 (386 mg; 0.869 mmol) in acetic acid (36 mL) and water (3 mL). The mixture was stirred at 80° C. for 6 h. Iron (146 mg; 2.61 mmol) was added and the mixture was stirred at 80° C. for 16 h. Iron (146 mg; 2.61 mmol) was added again and the mixture was stirred at 80° C. for 5 h. The mixture was concentrated until dryness. DMF was added, the mixture was filtered through celite and the celite was rinsed with DMF. Siliabond Imidazole (18 g; 20.9 mmol) was added to the filtrate and the mixture was stirred at rt for 72 h.

The mixture was filtered through celite, the celite was rinsed with DMF and the filtrate was concentrated in vacuo to give 428 mg of a brown solid. The solid was taken up in $CH_3CN$ leading to precipitation. The precipitate was filtered to give 267 mg of a brown solid. The solid was purified by preparative LC (Irregular SiOH 15-40 µm, 10 g Merck, dry loading, mobile phase gradient: from $CH_2Cl_2$/MeOH/ $NH_3$aq 95/5/0.5 to 85/15/1.5). The fractions containing product were combined and the solvent was removed in vacuo to give 124 mg of an off-white solid. The solid was purified by Reverse phase (Stationary phase: Sunfire-C18 5 µm 19×150 mm, mobile phase gradient: from $CH_3CN/H_2O$ (formic acid 0.1%) 5/95 to 50/50) to give 72 mg of final compound 15 (23% yield) as a white solid.

Synthesis of Intermediate F2

Intermediate F2 was obtained with the procedures described for intermediate F1 (E isomer).

Synthesis of Final Compound 16

At rt, $TiCl_3$ (12.3 mL; 14.341 mmol) was added drop wise to a mixture of F2 (300 mg; 0.717 mmol) in THF (30 mL). The mixture was stirred at rt for 2 hours. The mixture was cooled down to 0° C. and basified with $K_2CO_3$ powder. The resulting muddy mixture was filtered through a pad of celite and the celite was washed with a solution of AcOEt/$CH_3OH$ 8/2. The filtrate was partially evaporated to give 175 mg of final compound 16 after filtration of a white solid and drying under vacuum pressure at 85° C. (71% yield).

Synthesis of Final Compound 17

The hydrochloride salt was prepared with 10 eq of HCl 4N in dioxane, which was added to the suspension of compound 16 (100 mg; 0.292 mmol) in $CH_3OH$ (10 mL). The precipitate was stirred for 3 h, filtered and dried under vacuum at 90° C. overnight. The solid was solubilized in MeOH/$CH_2Cl_2$ 50/50, $CH_3CN$ was added and the solvent was evaporated up to precipitation of a white solid, which was filtered and dried under vacuum at 90° C. to give 47 mg of final compound 17 as an HCl salt (0.93 HCl, 0.51 $H_2O$; 42% yield).

Overall Scheme in the Preparation of Final Products: Method 11
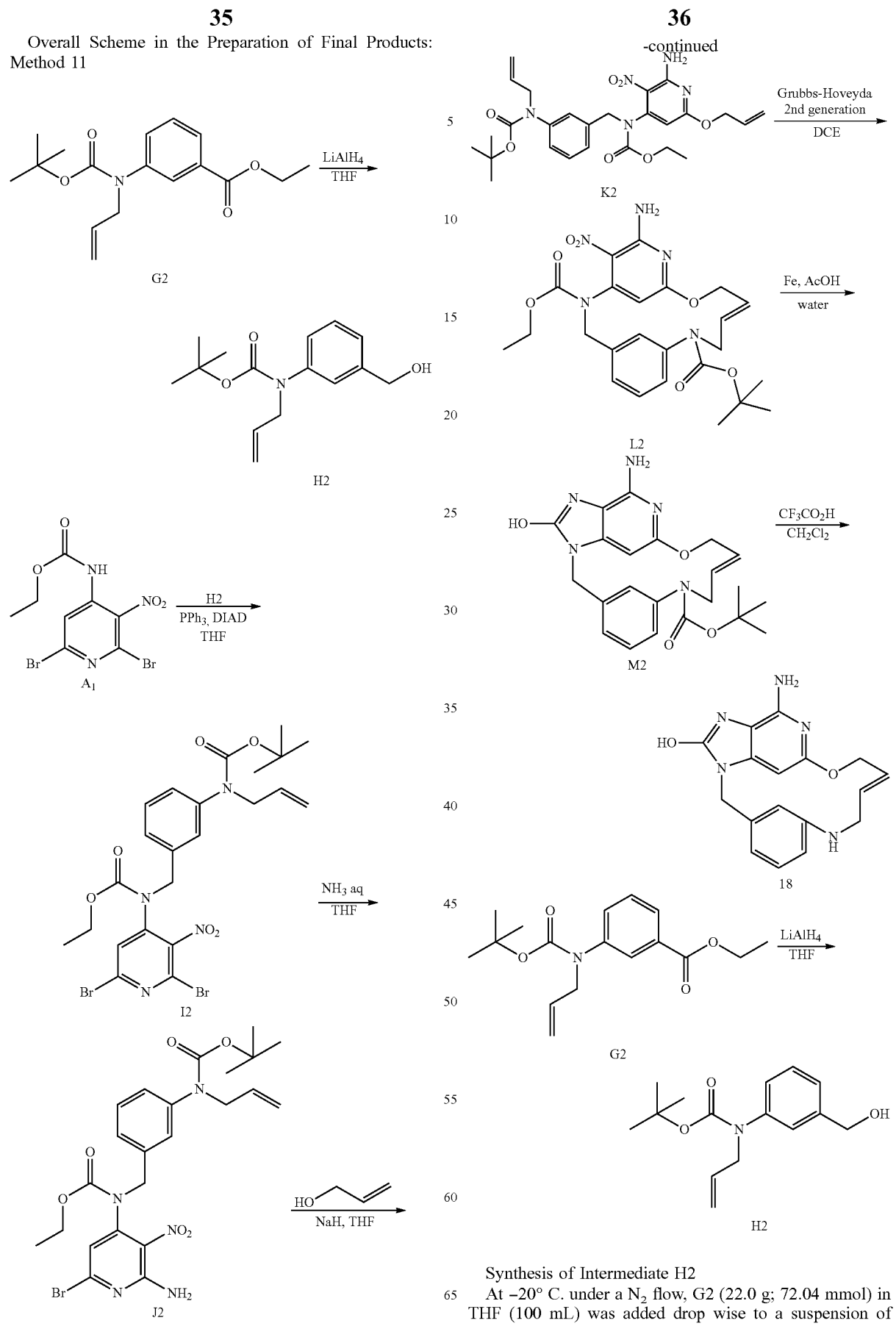
Synthesis of Intermediate H2
At −20° C. under a N₂ flow, G2 (22.0 g; 72.04 mmol) in THF (100 mL) was added drop wise to a suspension of LiAlH₄ (3.28 g; 86.45 mmol) in THF (120 mL). The mixture was stirred at 0° C. for 1 h. 3.5 mL of water was added dropwise, followed by 3.5 mL of NaOH 3N and 10 mL of water. The resulting mixture was filtered through a pad of celite and the celite was washed with EtOAc. The filtrate was concentrated under reduced pressure to give 19 g of intermediate H2 as a yellow oil (quantitative yield).

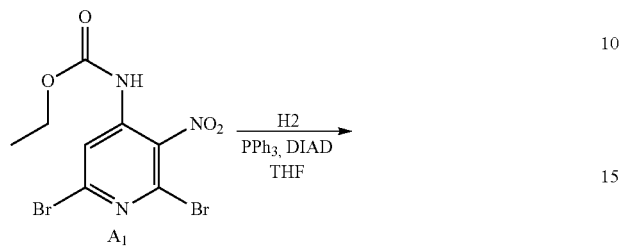

Synthesis of Intermediate 12

At 0° C., diisopropylazodicarboxylate (4.0 mL; 20.32 mmol) was added drop wise to a mixture of A1 (5.0 g; 13.55 mmol), H2 (4.28 g; 16.26 mmol) and PPh₃ (5.33 g; 20.327 mmol) in THF (100 mL). The mixture was stirred at rt for 12 h. EtOAc and water were added. The layers were decanted. The organic layer was washed with water, dried over MgSO₄, filtered and the solvent was evaporated. The crude compound was dissolved in Heptane/EtOAc 80/20, the precipitate was filtered off (mainly POPh3) and the filtrate was purified by chromatography. Purification was carried out by flash chromatography over silica gel (15-40 µm, 220 g, Heptane/EtOAc 80/20) The pure fractions were collected and evaporated to dryness to give 8.2 g of intermediate 12 (99% yield).

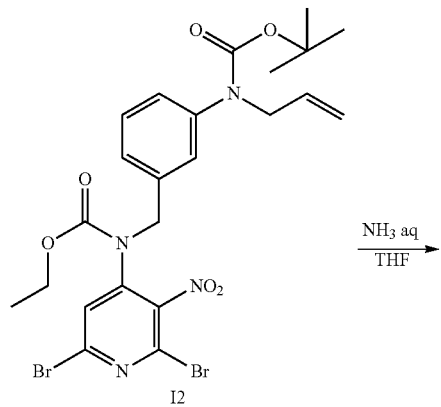

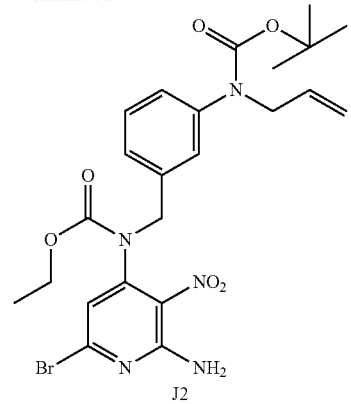

Synthesis of Intermediate J2

I2 (8.2 g; 13.349 mmol) was stirred in NH₄OH (100 mL) and THF (100 mL) at rt for 24 h. The mixture was half evaporated under reduced pressure. The residue was taken up with EtOAc. The organic layer was washed with water, dried over MgSO₄, filtered and the solvent was evaporated to give 8.15 g of intermediate J2 (quantitative yield). The crude compound was used directly in the next reaction step.

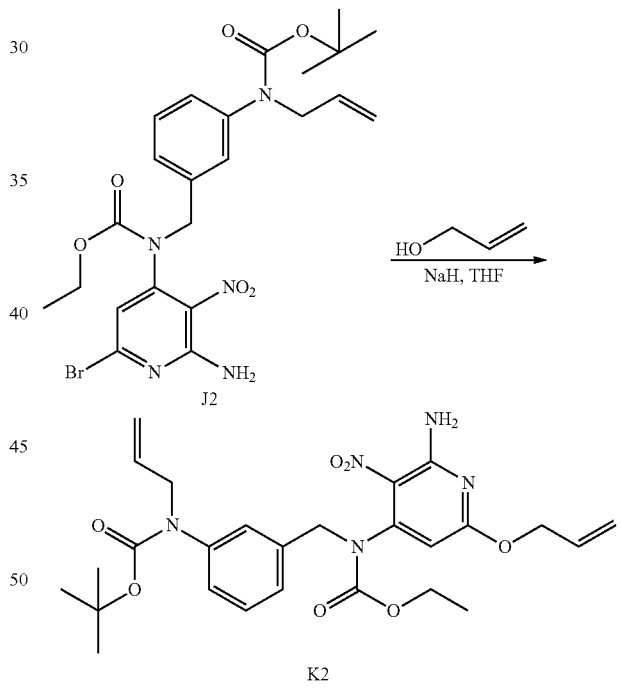

Synthesis of Intermediate K2

Under a N₂ flow, NaH (60% in oil) (1.15 g; 28.64 mmol) was added portion wise to allyl alcohol (35 mL) at rt. The mixture was stirred at rt for 30 min before being added drop wise to a solution of J2 (4.0 g; 7.26 mmol) in THF (80 mL) at 0° C. The resulting mixture was then stirred at rt for 2 h 30 min and was poured in a saturated solution of NH4Cl. EtOAc and a saturated aqueous solution of NaCl were added, the layers were separated and the aqueous layer was extracted with EtOAc (once). The combined organic layers were dried over MgSO₄, filtered and the solvent was removed under reduced pressure to give 4.7 g of a yellow oil. Purification was carried out by flash chromatography over silica gel (15-40 μm, 80 g, CH₂Cl₂/Heptane 65/35). The pure fractions were collected and evaporated to dryness to give 2.65 g of intermediate K2 (69% yield).

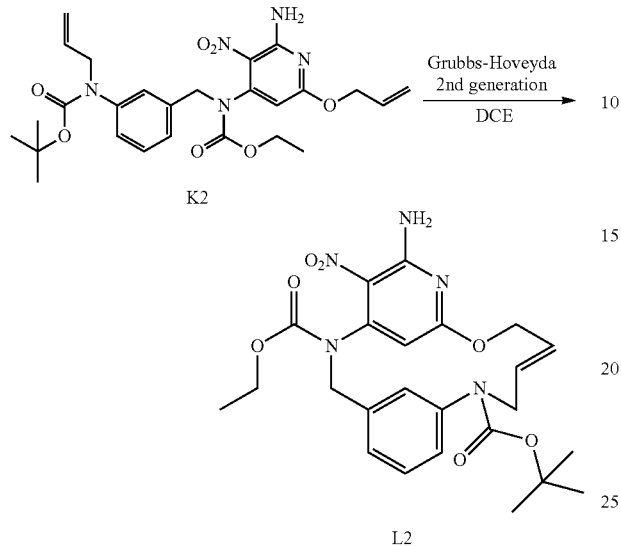

Synthesis of Intermediate L2

Prior to the reaction, the dichloroethane was degassed by bubbling N₂ through.

In a Slenck tube, a solution of K2 (1.3 g; 2.464 mmol) and chlorodicyclohexylborane (1 M in hexane) (493 μL; 0.493 mmol) in dichloroethane (600 mL) was stirred at 80° C. under N₂ for 1 h. Grubbs-Hoveyda catalyst 2$^{nd}$ generation (609 mg; 0.493 mmol) was added and the mixture was stirred at 120° C. for 16 h. Siliabond DMT (2.98 g; 1.82 mmol) was added and the mixture was stirred at rt for 16 h. The reaction mixture was filtered through celite and the filtrate was evaporated in vacuo to give 1.6 g which was combined with another reaction (2.46 mmol scale) before purification (total weight to purify 3.2 g). Purification was carried out by flash chromatography over silica gel (15-40 μm, 80 g, CH₂Cl₂/CH₃OH: 99.5/0.5). The pure fractions were collected and evaporated to dryness to give 0.99 g of F1 (E/Z mixture of expected compound, 40% yield) and 0.65 g of F2 (starting material K2).

F1 was further purified by achiral SFC (Stationary phase: NH₂ 5 μm 150*30 mm), Mobile phase: 92% CO₂, 8% MeOH) to give 664 mg of intermediate L2 (E isomer, 27% yield).

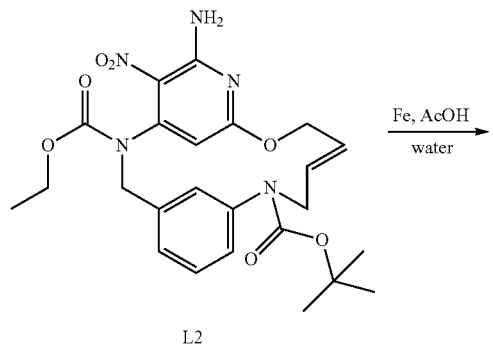

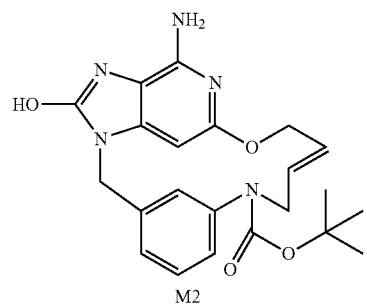

Synthesis of Intermediate M2

Iron (1.45 g; 26.025 mmol) was added to a mixture of L2 (0.65 g; 1.301 mmol) in acetic acid (15 mL) and water (1.5 mL). The mixture was stirred at 50° C. for 3 h, and then filtered through celite with CH₂Cl₂/MeOH. The filtrate was concentrated under reduced pressure. The compound was purified by flash chromatography over silica gel column (15-40 μm; 80 g, eluent CH₂Cl₂/CH₃OH/NH₄OH 96/4/0.5) to give 640 mg. A second purification was carried out by flash chromatography over silica gel (15-40 μm, 40 g, CH₂Cl₂/CH₃OH/NH₄OH: 97/3/0.2). The pure fractions were collected and evaporated to dryness to give 240 mg of intermediate M2 (38% yield).

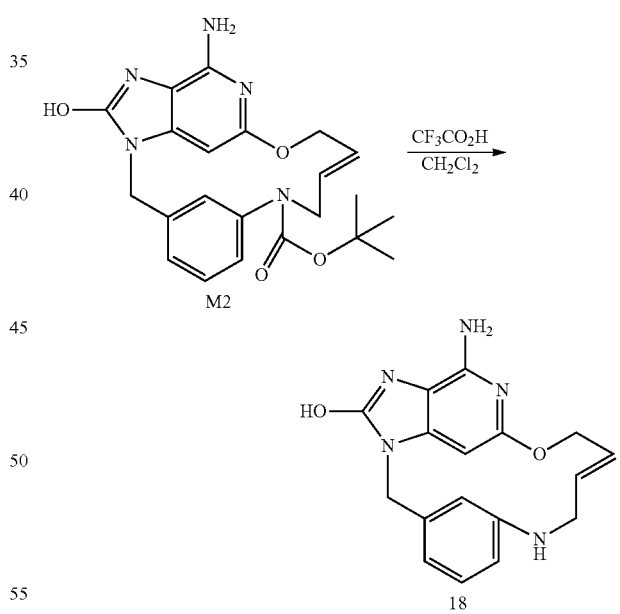

Synthesis of Final Compound 18

At 0° C., CF₃CO₂H (0.455 mL) was added drop wise to a mixture of M2 (100 mg, 0.236 mmol) in CH₂Cl₂ (1 mL). The mixture was stirred at rt overnight, and then basified with a 10% solution of K₂CO₃ in water. The precipitate was filtered off, washed with water and CH₃CN, and finally dried under vacuum to afford 35 mg of final compound 18 (E isomer, 46% yield).

Overall Scheme in the Preparation of Final Products: Method 12

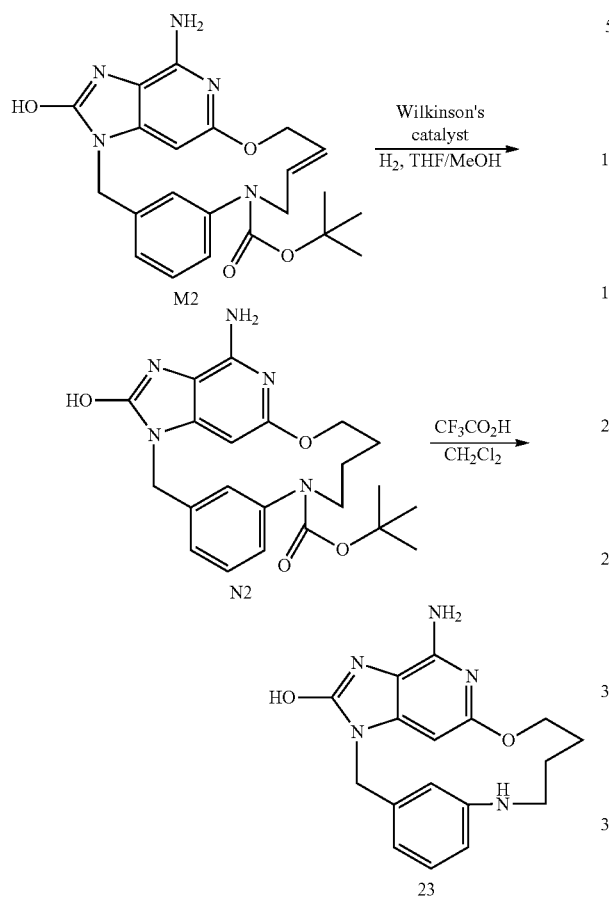

Overall Scheme in the Preparation of Final Products: Method 13

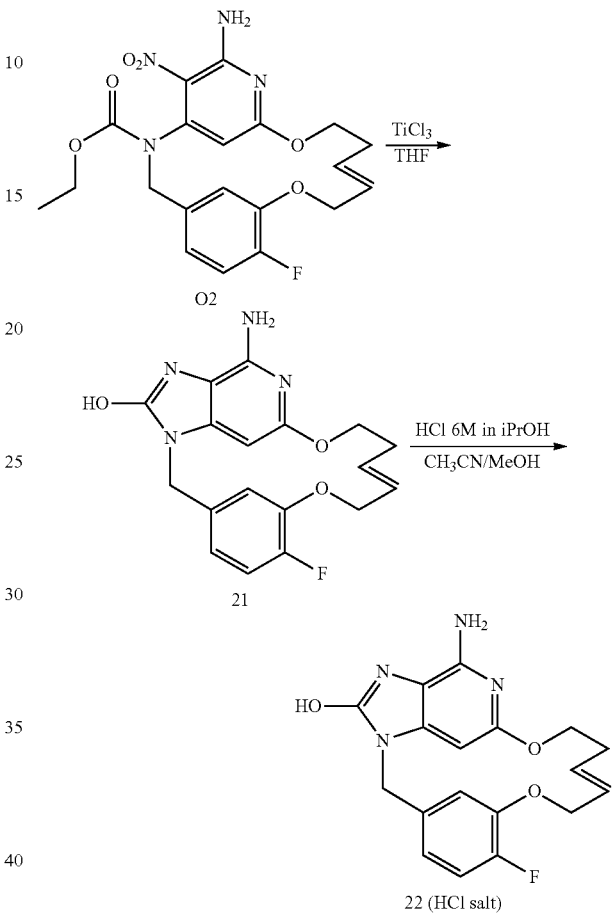

Synthesis of Intermediate N2

A mixture of M2 (140 mg, 0.331 mmol) in THF/CH$_3$OH (50/50) (30 mL) was hydrogenated under a 10 Bars pressure with Wilkinson's catalyst (61.2 mg, 0.0661 mmol) for 72 h. Siliabond DMT (441 mg, 0.264 mmol) was added and the mixture was stirred at rt for 18 h. The mixture was filtered through a pad of celite and the celite was washed with CH$_2$Cl$_2$/CH$_3$OH 95/5. The filtrate was concentrated under reduced pressure. Purification was carried out by flash chromatography over silica gel (15-40 μm, 10 g, CH$_2$Cl$_2$/CH$_3$OH/NH$_4$OH: 97/3/0.1). The pure fractions were collected and evaporated to dryness to give 62 mg of intermediate N2 (44% yield) used as such in the next step.

Synthesis of Final Compound 23

At 0° C., CF$_3$CO$_2$H (0.281 mL, 3.643 mmol) was added drop wise to a mixture of N2 (62 mg, 0.146 mmol) in CH$_2$Cl$_2$ (1 mL). The mixture was stirred at rt overnight. The mixture was basified with a 10% solution of K$_2$CO$_3$ in water. The mixture was extracted twice with CH$_2$Cl$_2$ and CH$_3$OH (80/20). The organic layer was dried over MgSO$_4$, filtered and the solvent was evaporated. The crude compound was taken up with DMF, 2 g of SiO$_2$ 60-200 μm was added and the resulting suspension was evaporated until dryness. This residue was put on the top of a chromatography column (solid deposit). Purification was carried out by flash chromatography over silica gel (15-40 μm, 25 g, CH$_2$Cl$_2$/CH$_3$OH/NH$_4$OH: 95/5/0.5). The pure fractions were collected and evaporated to dryness to give 20 mg. The fraction was taken up with CH$_3$CN, the precipitate was filtered off and dried under vacuum to afford 18 mg of final compound 23 (38% yield).

Synthesis of Intermediate O2

Intermediate O2 was obtained with the procedures described for intermediate X1 (E isomer).

Synthesis of Final Compound 21

At rt, TiCl$_3$ (51.5 mL; 60.128 mmol) was added drop wise to a mixture of O2 (1.3 g; 3.006 mmol) in THF (130 mL). The mixture was stirred at rt for 2 h. The mixture was cooled down to 0° C. and then basified with K$_2$CO$_3$ powder. The resulting muddy mixture was filtered through a pad of celite and the celite was washed with a solution of AcOEt/CH$_3$OH 8/2. The filtrate was partially evaporated to give 380 mg of final compound 21 (35% yield) after filtration of a white solid and drying under vacuum at 85° C.

Synthesis of Final Compound 22

Compound 21 (118 mg, 0.331 mmol) in CH$_3$OH (2 mL)+CH$_3$CN (2 mL) was cooled down to 10° C. HCl (6M in isopropanol) (0.16 mL, 0.993 mmol) was added drop wise and the mixture was stirred at rt for 1 h. The precipitate was filtered off, washed with Et$_2$O and dried under vacuum to give 109 mg of final compound 22 as an HCl salt (0.76 HCl 0.81 H$_2$O, 83% yield).

Overall Scheme in the Preparation of Final Products: Method 14

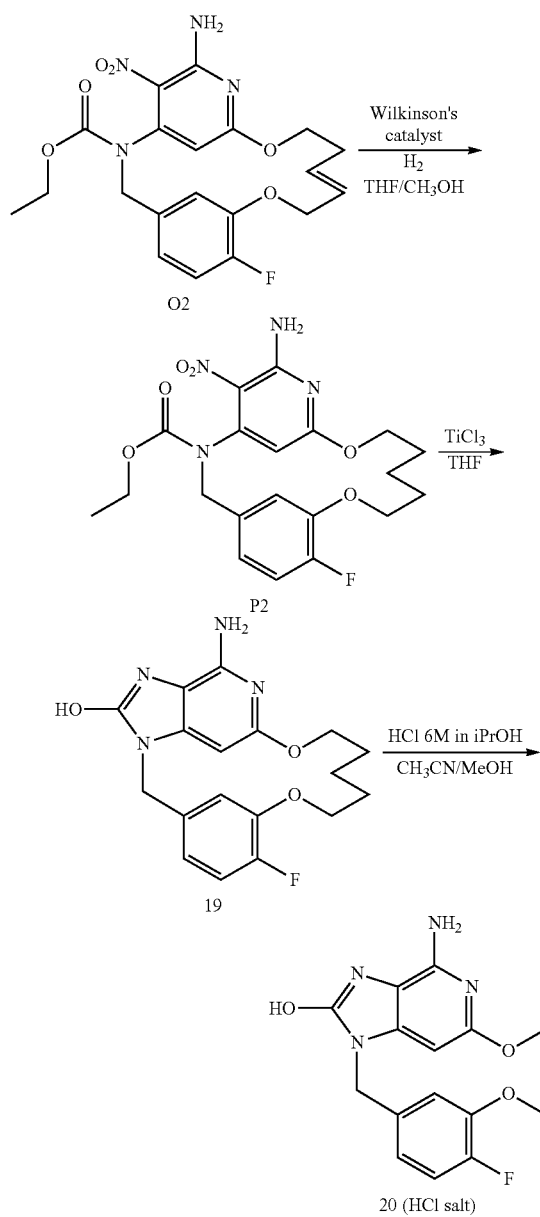

Synthesis of Intermediate P2

A mixture of O2 (320 mg; 0.74 mmol), Wilkinson's catalyst (137 mg; 0.148 mmol) in THF/CH$_3$OH (50/50) (45 mL) was hydrogenated under 10 bars pressure at rt for 20 h. Solvent was evaporated under vacuum. The crude compound was purified by flash chromatography over silica gel column (15-40 μm; 24 g) in Heptane/AcOEt 80/20 to give 310 mg of intermediate P2 (96% yield).

Synthesis of Final Compound 19

At rt, TiCl$_3$ (9.5 mL; 11.049 mmol) was added drop wise to a mixture of P2 (0.24 g; 0.552 mmol) in THF (25 mL). The mixture was stirred at rt for 2 h. The mixture was cooled down to 0° C. and then basified with K$_2$CO$_3$ powder. The resulting muddy mixture was filtered through a pad of celite and the celite was washed with a solution of AcOEt/CH$_3$OH 8/2. The filtrate was partially evaporated to give 100 mg of final compound 19 (50% yield) after filtration of a white solid and drying under vacuum at 85° C.

Synthesis of Final Compound 20

Compound 19 (58 mg; 0.162 mmol) in CH$_3$OH (2 mL)+ CH$_3$CN (4 mL) was cooled down to 5° C. HCl (6M in isopropanol) (81 μL; 0.486 mmol) was added drop wise and the mixture was stirred at rt for 1 h. The precipitate was filtered off, washed with diisopropylether and dried under vacuum at 90° C. to give 57 mg of final compound 20 as an HCl salt (0.88 HCl 0.04 H$_2$O, 89% yield).

Overall Scheme in the Preparation of Final Products: Method 15

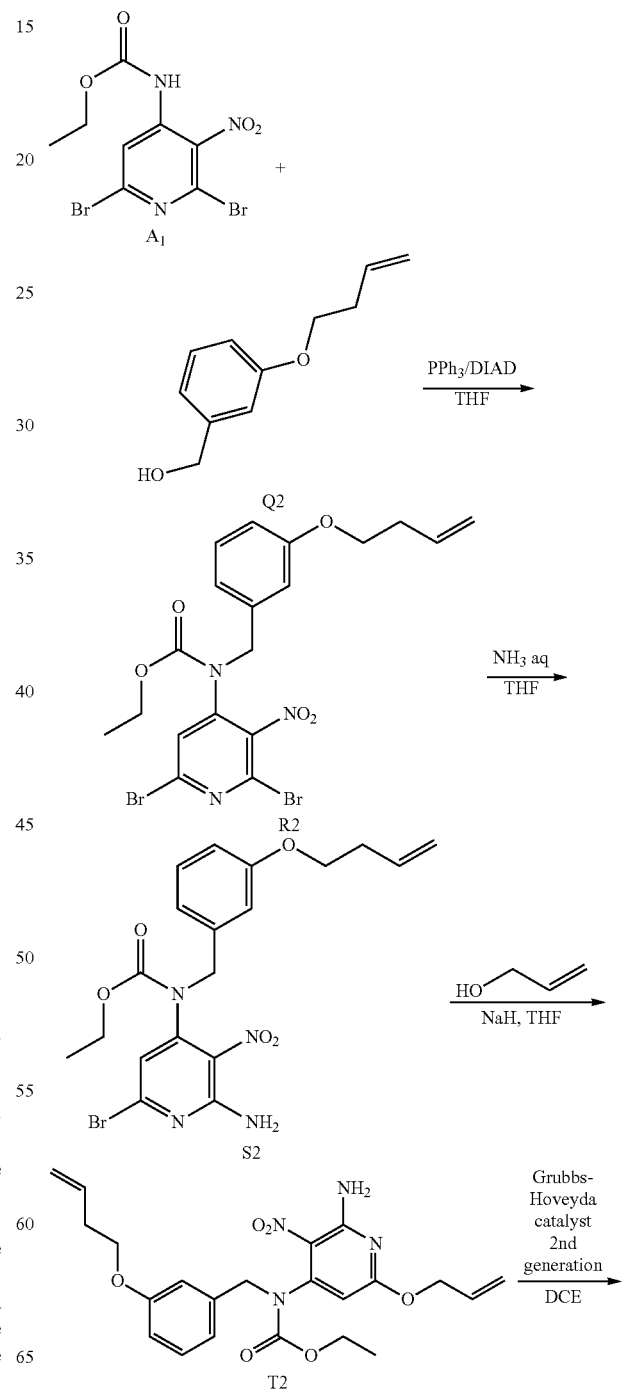

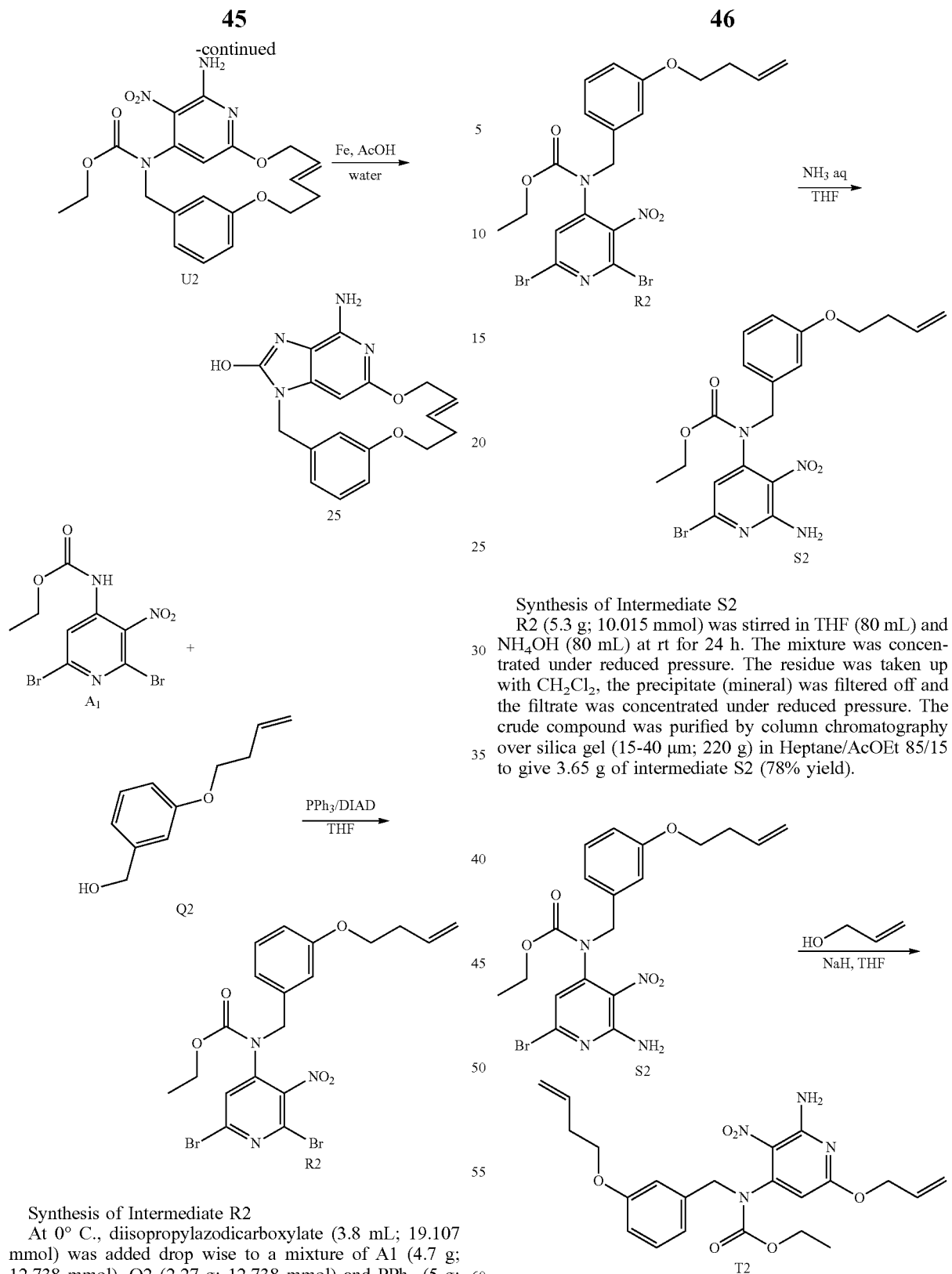

Synthesis of Intermediate S2

R2 (5.3 g; 10.015 mmol) was stirred in THF (80 mL) and NH$_4$OH (80 mL) at rt for 24 h. The mixture was concentrated under reduced pressure. The residue was taken up with CH$_2$Cl$_2$, the precipitate (mineral) was filtered off and the filtrate was concentrated under reduced pressure. The crude compound was purified by column chromatography over silica gel (15-40 μm; 220 g) in Heptane/AcOEt 85/15 to give 3.65 g of intermediate S2 (78% yield).

Synthesis of Intermediate R2

At 0° C., diisopropylazodicarboxylate (3.8 mL; 19.107 mmol) was added drop wise to a mixture of A1 (4.7 g; 12.738 mmol), Q2 (2.27 g; 12.738 mmol) and PPh$_3$ (5 g; 19.107 mmol) in THF (100 mL). The mixture was stirred at rt for 12 h. EtOAc and water were added. The layers were decanted. The organic layer was washed with water, dried over MgSO$_4$, filtered and the solvent was evaporated. The crude compound was purified by column chromatography over silicagel (15-40 μm; 220 g) in Heptane/AcOEt 85/15 to 5.3 g of intermediate R2 (79% yield).

Synthesis of Intermediate T2

NaH (1.35 g; 33.88 mmol) was added portion wise to allyl alcohol (41 mL) at rt. The mixture was stirred at rt for 30 min before being added drop wise to a solution of S2 (4 g; 8.597 mmol) in THF (100 mL) at 0° C. The resulting mixture was then stirred at rt for 2 h 30 min and was poured in an saturated aqueous solution of NH4Cl. EtOAc and a saturated aqueous solution of NaCl were added, the layers were separated and the aqueous layer was extracted with EtOAc (once). The combined organic layers were dried over MgSO$_4$, filtered and the solvent was removed under reduced pressure to give a yellow oil. The crude compound was purified by preparative LC (Irregular SiOH 15-40 µm, 120 g Grace, liquid injection, mobile phase gradient: Heptane/EtOAc 85/15) to give 3.2 g of intermediate T2 as a yellow oil (84% yield).

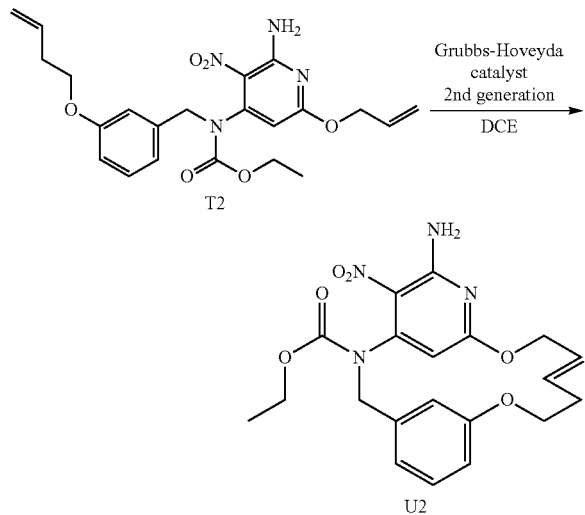

Synthesis of Intermediate U2

A solution of T2 (1 g; 2.26 mmol) and chlorodicyclohexylborane (1M in hexane) (904 µL; 904.013 µmol) in dry dichloroethane (540 mL) was stirred at 80° C. and under N$_2$ atmosphere for 1 h. The mixture was degassed by N$_2$ bubbling for 15 min, Grubbs-Hoveyda catalyst $2^{nd}$ generation (141.6 mg; 226 µmol) was added, the mixture was degassed again by N$_2$ bubbling for 15 min and then stirred at 120° C. for 16 h. 0.25 eq of catalyst were added again and mixture was stirred at 120° C. for 16 h. Siliabond DMT (5.9 g; 3.616 mmol) was added and the mixture was stirred rt for 16 h. The mixture was filtered through a pad of celite and the filtrate was concentrated under vacuum to give a black oil. The crude compound was purified by preparative LC (Irregular SiOH 15-40 µm, 80 g Merck, mobile phase: CH$_2$Cl$_2$/AcOEt 97/3). The fractions containing product were combined and the solvent was removed under vacuum to give 335 mg of intermediate U2 (E isomer, 36% yield).

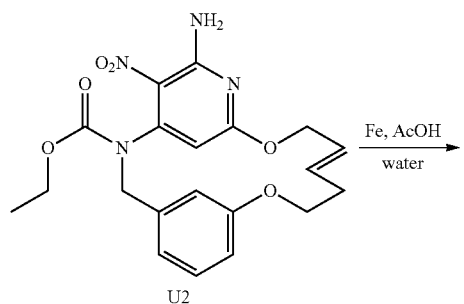

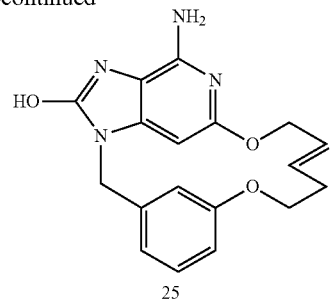

Synthesis of Final Compound 25

Iron (0.45 g; 8.084 mmol) was added to a mixture of U2 (0.335 g; 0.808 mmol) in acetic acid (24 mL)+water (5 mL). The mixture was stirred vigorously at 50° C. for 5 h.

CH$_2$Cl$_2$ was added and the reaction mixture was filtered through a pad of celite, and then washed with acetic acid. The solvent was removed under reduced pressure. The crude was purified by chromatography over silicagel column (SiO2 15-40 µm, 25 g) in CH$_2$Cl$_2$/CH$_3$OH/NH$_4$OH 96/4/0.5 to give 154 mg of final compound 25 (56% yield). The compound was crystallized in CH$_3$OH, filtered and dried under vacuum at 90° C. to give 70 mg (25% yield).

Overall Scheme in the Preparation of Final Products: Method 16

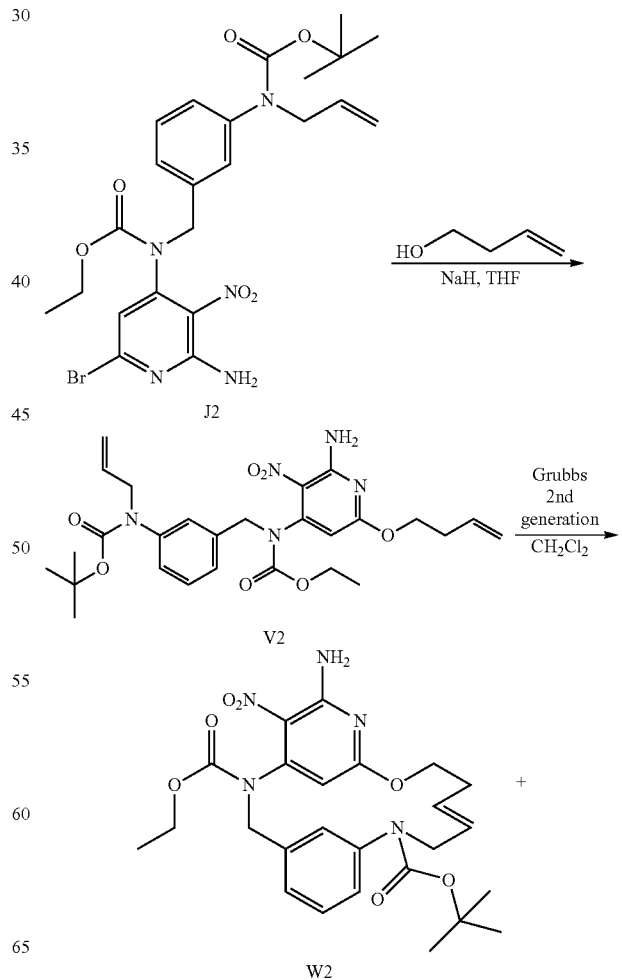

49
-continued
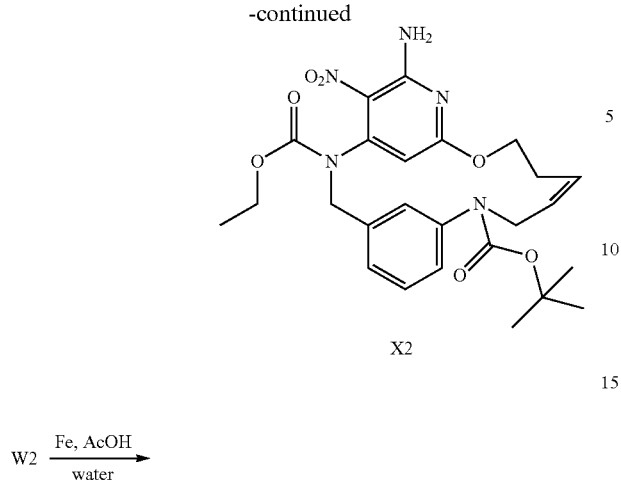
X2
W2 →(Fe, AcOH, water)
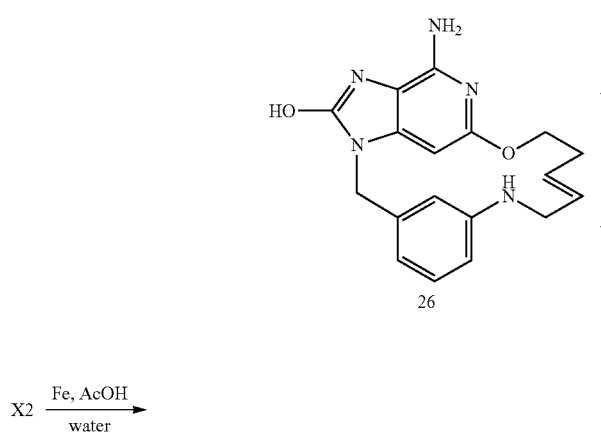
Y2
→(CF₃CO₂H, CH₂Cl₂)
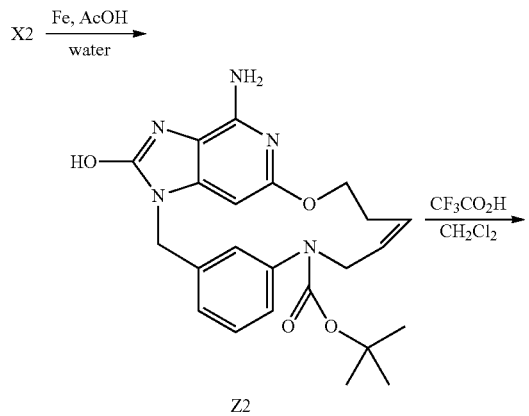
26
X2 →(Fe, AcOH, water)
Z2 →(CF₃CO₂H, CH₂Cl₂)
50
-continued
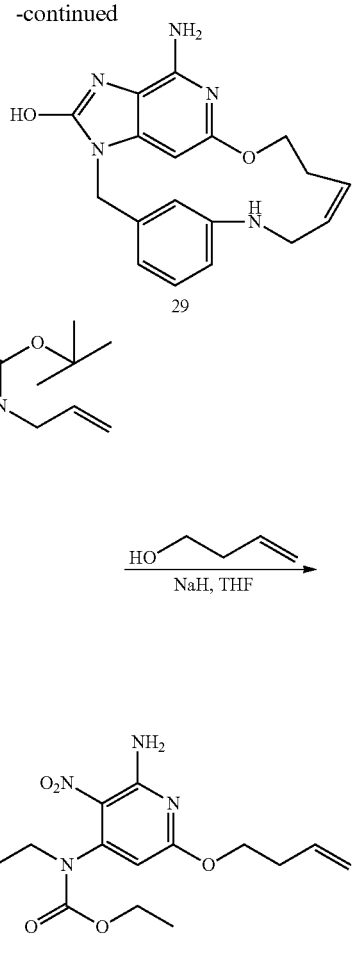
29
J2 →(HO-CH₂CH₂CH=CH₂, NaH, THF)
V2
Synthesis of Intermediate V2
Intermediate V2 was synthesized using the procedure described for intermediate K2 with 3-butenol as starting material (3.9 g, 44% yield).
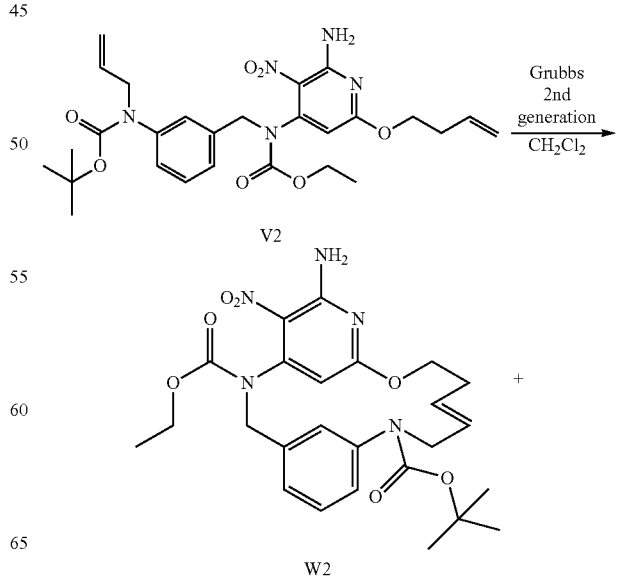
V2 →(Grubbs 2nd generation, CH₂Cl₂) W2 +

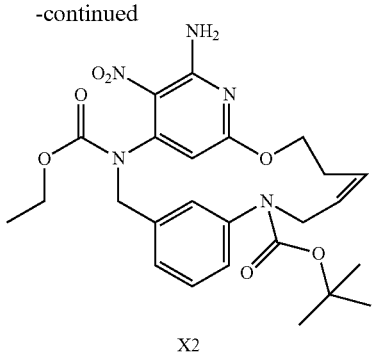

X2

Synthesis of Intermediates W2 and X2

Grubbs catalyst 2$^{nd}$ generation (236 mg, 0.277 mmol) was added to a mixture of V2 (1.5 g, 2.77 mmol) in dry CH$_2$Cl$_2$ (400 mL). The mixture was stirred at rt under a N$_2$ flow for 24 h. Siliabond DMT (3.6 g, 2.216 mmol) was added and the mixture was stirred at rt for 12 h. The mixture was filtered through celite, the celite was washed with CH$_2$Cl$_2$ and the filtrate was evaporated. Purification was carried out by flash chromatography over silica gel (15-40 μm, 80 g, CH$_2$Cl$_2$/CH$_3$OH: 99.5/0.5) pure fractions were collected and evaporated to dryness to give 0.98 g of a mixture of W2 and X2. The two isomers were separated by achiral SFC (Stationary phase: CHIRALPAK IC 5 μm 250×20 mm), Mobile phase: 70% CO$_2$, 30% CH$_3$OH) to give 0.805 g of intermediate W2 (E isomer, 57% yield) and 0.14 g of intermediate X2 (Z isomer, 10% yield).

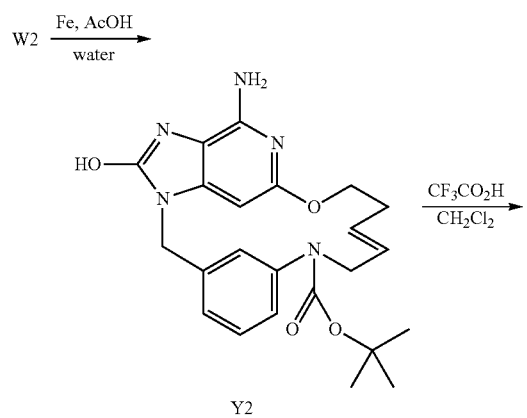

Y2

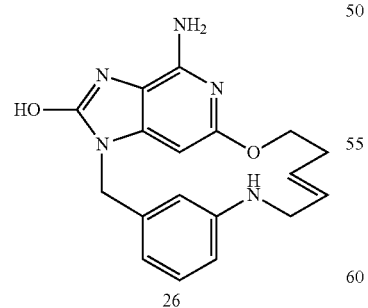

26

Synthesis of Final Compound 26

Final compound 26 was synthesized with the procedures described for final compound 18 (1$^{st}$ step: Y2, 0.68 g, 99% yield; 2$^{nd}$ step: 52 mg, 27% yield).

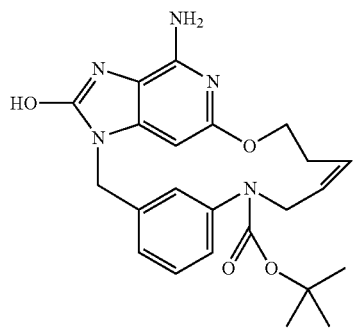

Z2

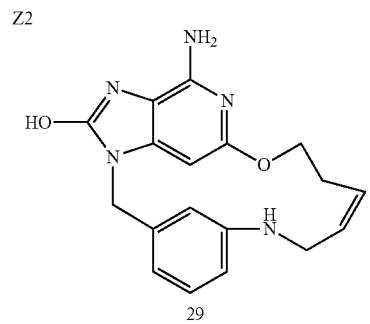

29

Synthesis of Final Compound 29

Final compound 29 was synthesized with the procedures described for final compound 18 (1$^{st}$ step: Z2, 0.12 g, 100% yield; 2$^{nd}$ step: 8 mg, 9% yield).

Overall Scheme in the Preparation of Final Products: Method 17

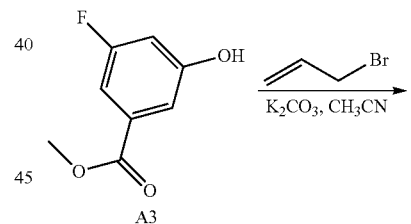

A3

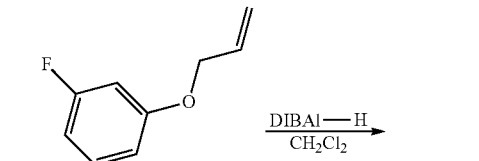

B3

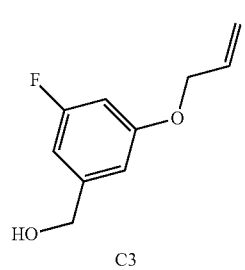

C3

53
-continued

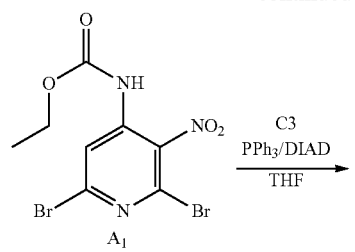

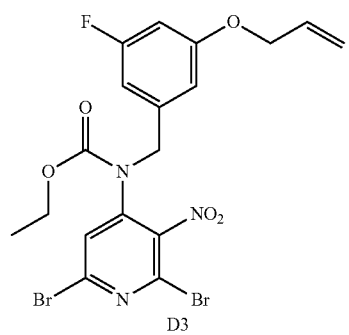

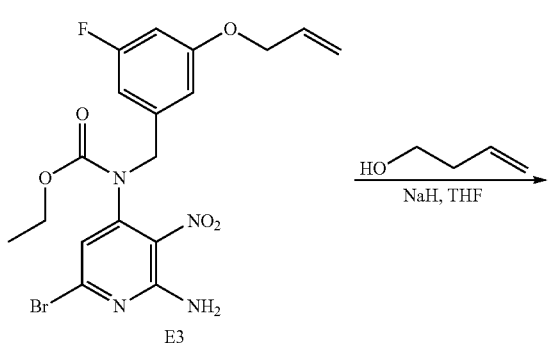

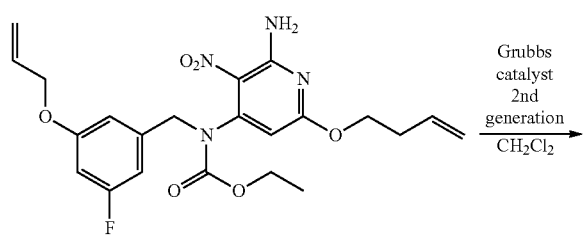

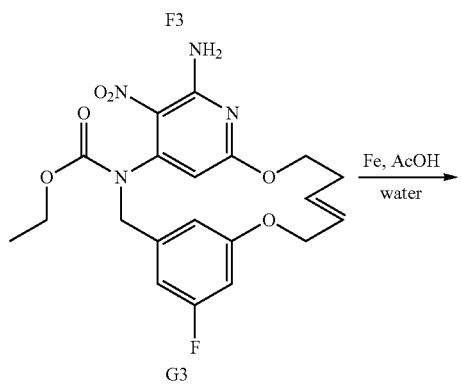

54
-continued

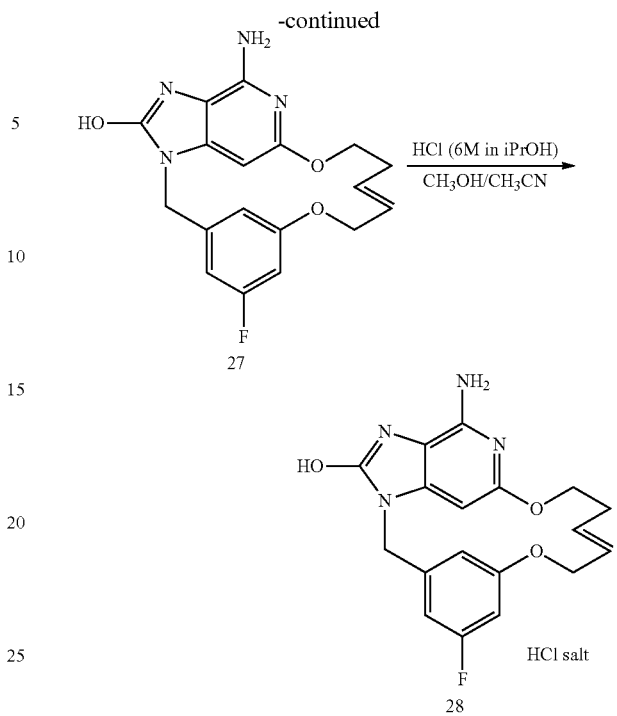

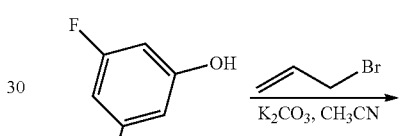

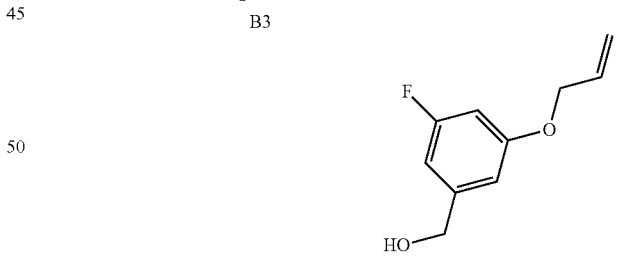

Synthesis of Intermediate B3

Allyl bromide (13 mL, 0.15 mmol) was added drop wise to a mixture of A3 (23 g, 0.135 mmol) and $K_2CO_3$ (28 g, 0.2 mmol) in $CH_3CN$ (460 mL). The mixture was stirred at reflux for 4 h, and then concentrated under reduced pressure. The residue was taken up with water and was extracted with EtOAc. The organic layers were combined, washed with water, dried over $MgSO_4$, filtered and the solvent was evaporated. The crude compound (27 g, 95% yield) was used directly in the next reaction step.

Synthesis of Intermediate C3

Under N$_2$, DIBAL-H (1.2 M in toluene) (97 mL; 116.5 mmol) was added to a solution of B3 (9.8 g; 46.6 mmol) in dry CH$_2$Cl$_2$ (250 mL) at 0° C. The reaction mixture was stirred at 0° C. for 1 h, and then 1 h at rt. Water was added. The organic layer was separated from the aqueous layer, dried over MgSO$_4$, filtered and concentrated under vacuum to give 8.4 g of intermediate C3 (99% yield). The crude compound was used directly in the next reaction step.

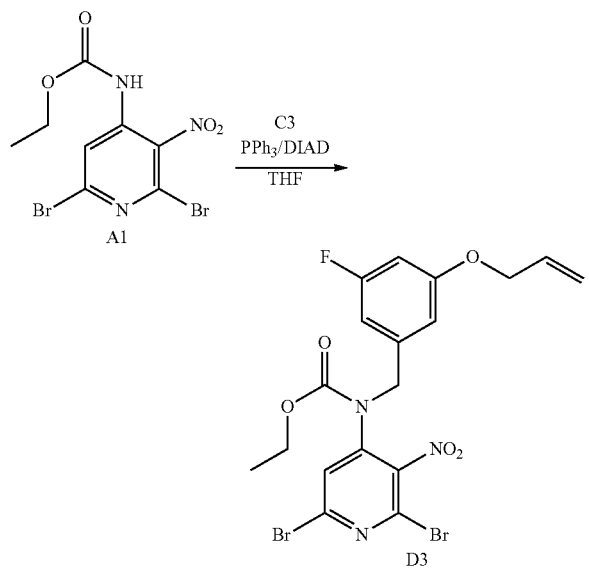

Synthesis of Intermediate D3

Intermediate D3 was synthesized using the procedure described for intermediate R2 with C3 as starting material (1.9 g, 88% yield).

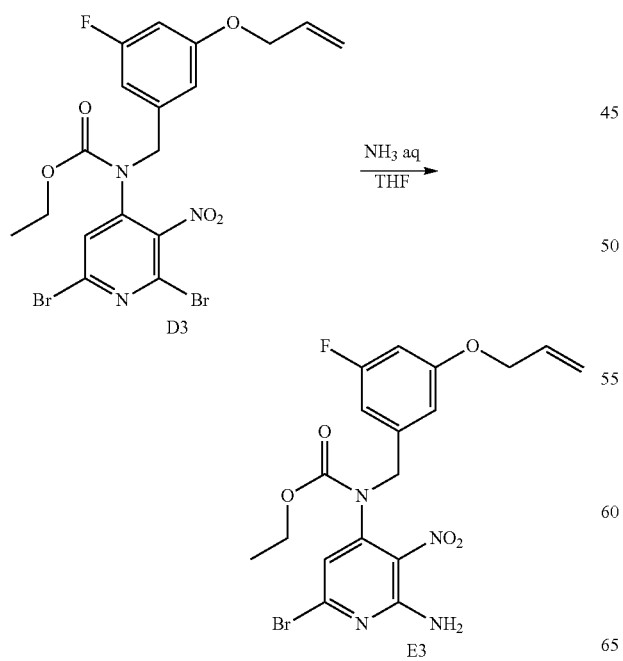

Synthesis of Intermediate E3

Intermediate E3 was synthesized using the procedure described for intermediate S2 with D3 as starting material (1.8 g, 93% yield).

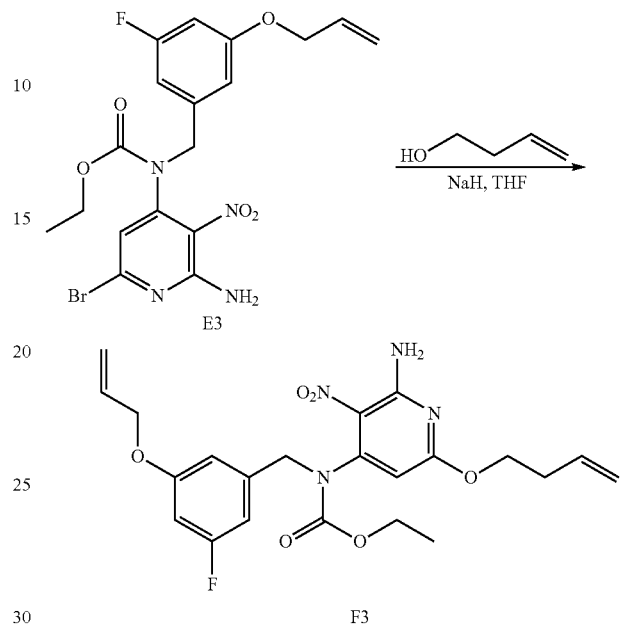

Synthesis of Intermediate F3

Intermediate F3 was synthesized using the procedure described for intermediate W1 with E3 as starting material (0.65 g, 66% yield).

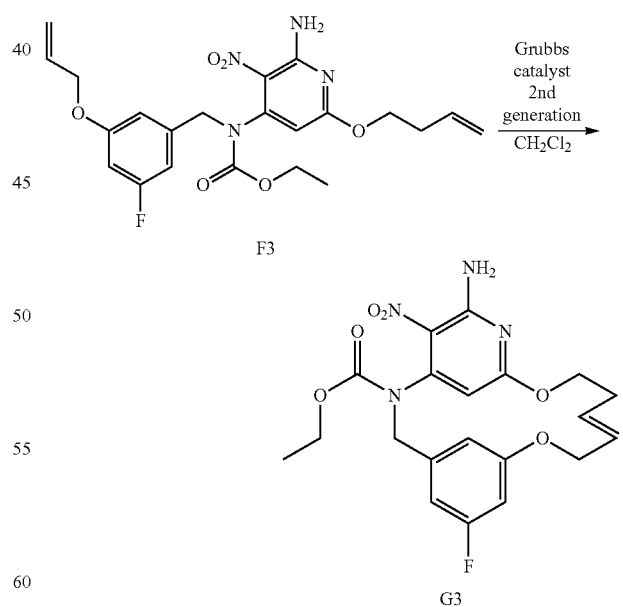

Synthesis of Intermediate G3

Intermediate G3 was synthesized using the procedure described for intermediate X1 with intermediate F3 as starting material (E isomer, 520 mg, 19% yield).

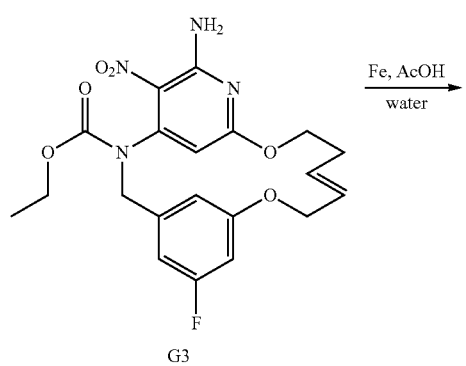

G3

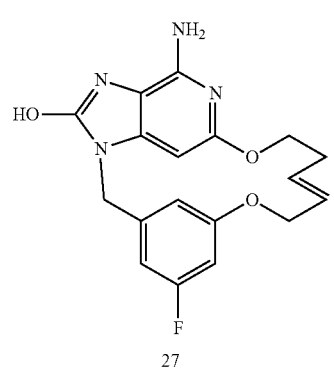

27

Synthesis of Final Compound 27

Final compound 27 was synthesized using the procedure described for final compound 10 with intermediate G3 as starting material (174 mg, 42% yield).

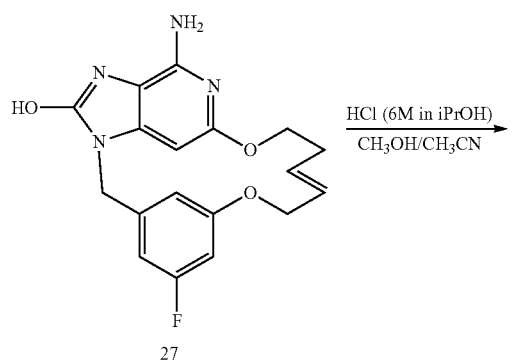

27

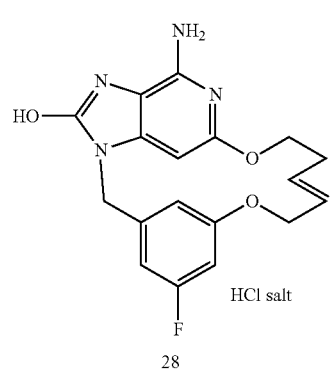

28

Synthesis of Final Compound 28

Final compound 28 was synthesized using the procedure described for final compound 20 with compound 27 as starting material (1.01 HCl 0.89 $H_2O$, 95 mg, 69% yield).

Overall Scheme in the Preparation of Final Products: Method 18

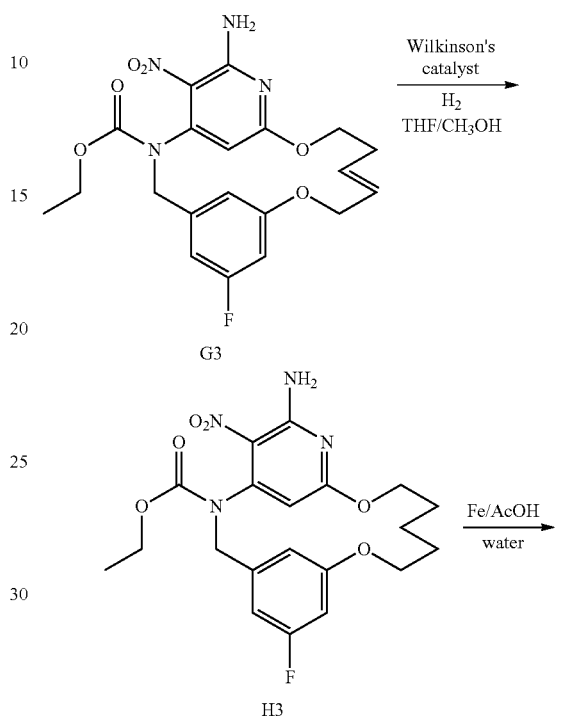

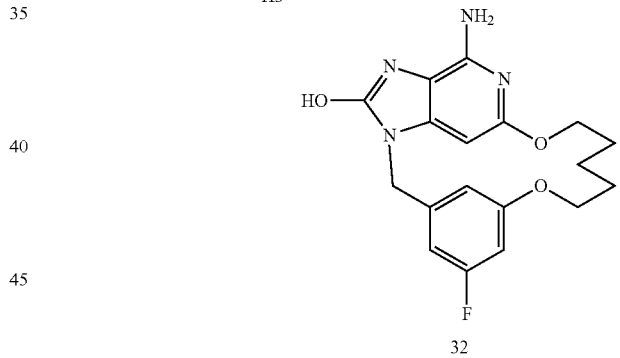

32

Synthesis of Intermediate H3

A mixture of G3 (600 mg, 1.39 mmol), Wilkinson's catalyst (257 mg; 0.278 mmol) in THF/$CH_3OH$ (50/50) (120 mL) was hydrogenated under 12 bars pressure at rt for 20 h. The solution was concentrated under reduced pressure. Purification was carried out by flash chromatography over silica gel (15-40 μm, 30 g, $CH_2Cl_2$/$CH_3OH$: 99.5/0.5). The pure fractions were collected and evaporated to dryness, and then crystallized from $CH_3CN$ to give 150 mg of intermediate H3 (25% yield).

Synthesis of Final Compound 32

A mixture of H3 (150 mg; 0.345 mmol) and iron (190 mg; 3.45 mmol) in acetic acid (13 mL) and water (1.5 mL) was stirred at 50° C. for 5 h. $CH_2Cl_2$ was added and the reaction mixture was filtered through a pad of celite and concentrated under vacuum. The crude compound was taken up with DMF, filtered through a pad of celite and concentrated. The solid was pre-purified by chromatography over silicagel column (SiO$_2$ 63-200 µm. 80 g) in CH$_2$Cl$_2$/CH$_3$OH/NH$_4$OH (98/2/0.1 to 90/10/0.5). A second purification by achiral SFC (Stationary phase: Whelk O1 (S,S) 5 µm 250*21.1 mm), Mobile phase: 60% CO$_2$, 40% CH$_3$OH (0.3% iPrNH$_2$)) afforded 27 mg of final compound 32 (22% yield).

Overall Scheme in the Preparation of Final Products: Method 19

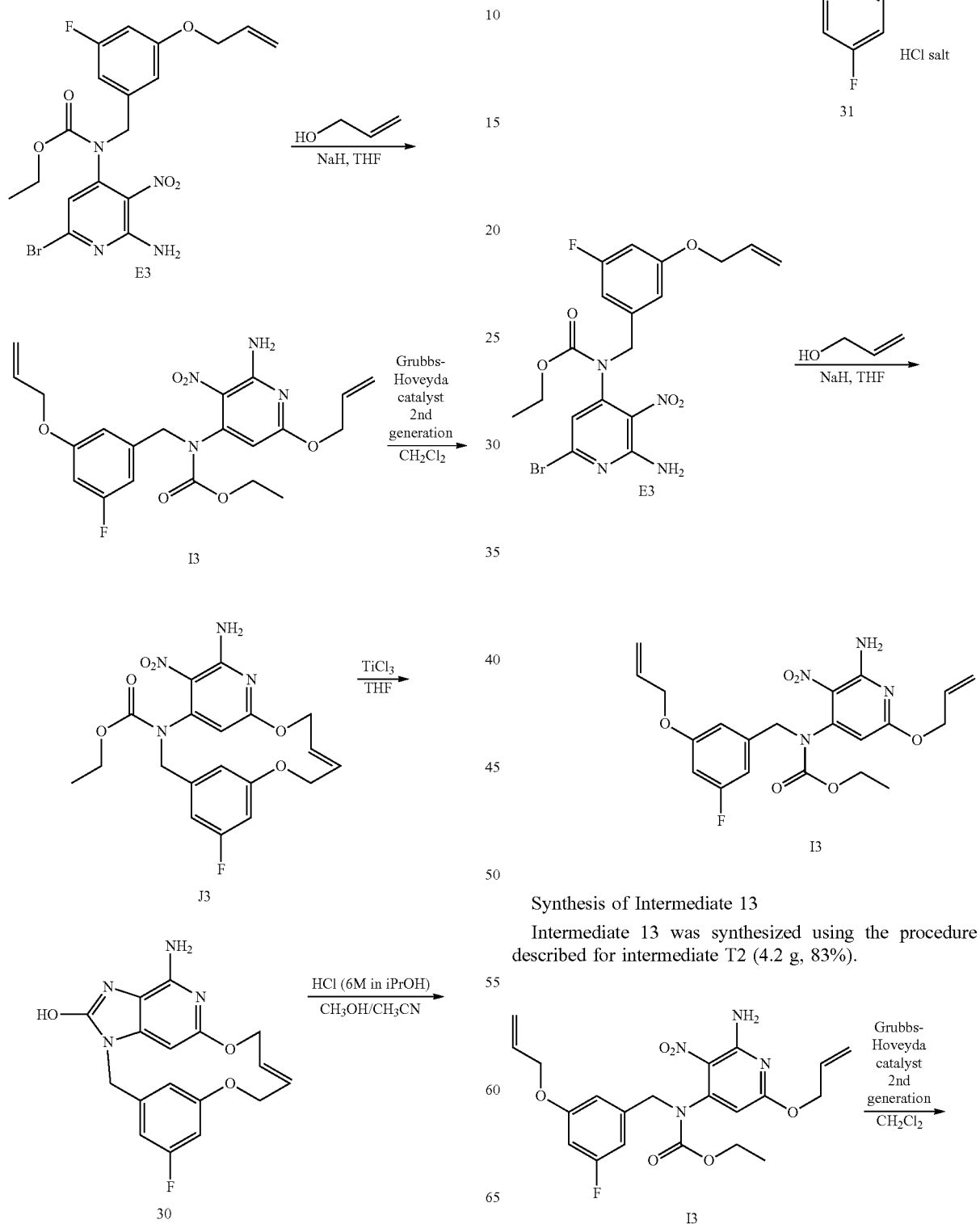

Synthesis of Intermediate 13

Intermediate 13 was synthesized using the procedure described for intermediate T2 (4.2 g, 83%).

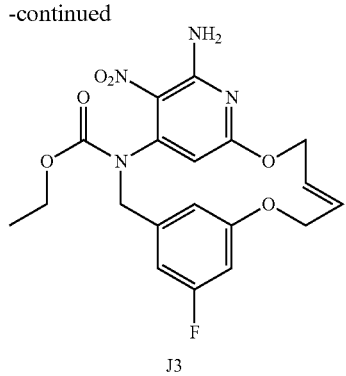

Synthesis of Intermediate J3

Intermediate J3 was synthesized using the procedure described for intermediate F1 (isomer E, 125 mg, 17%).

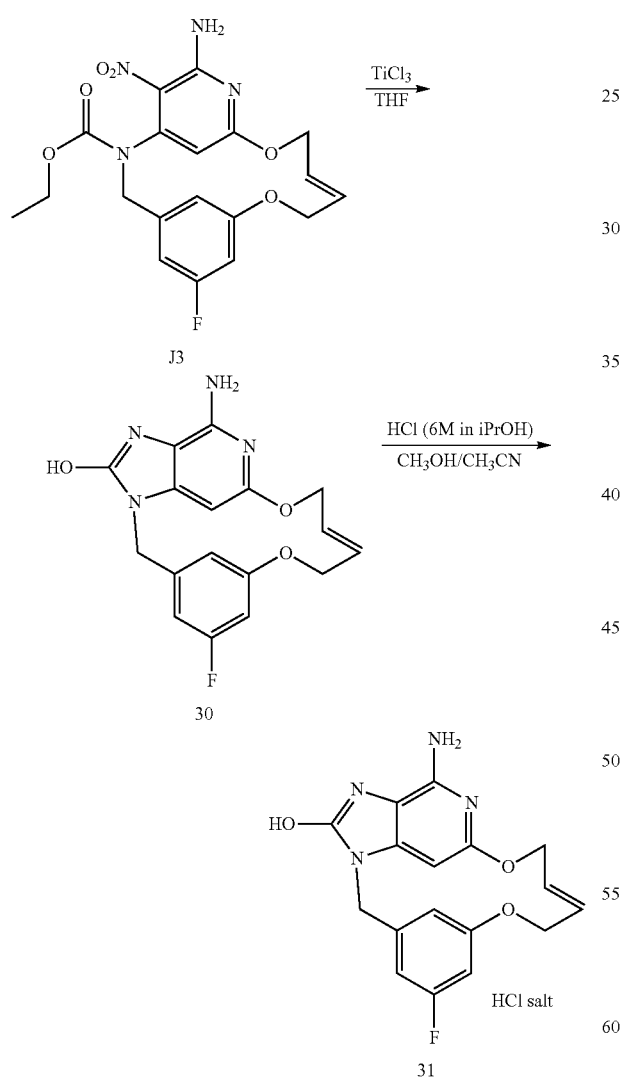

Synthesis of Final Compound 30

Final compound 30 was synthesized using the procedure described for final compound 21 (72 mg, 44% yield).

Synthesis of Final Compound 31

Final compound 31 was synthesized using the procedure described for final compound 22 (0.98 HCl 0.15 H₂O, 72 mg, 59% yield).

Overall Scheme in the Preparation of Final Products: Method 20

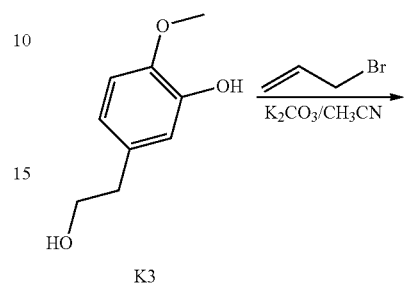

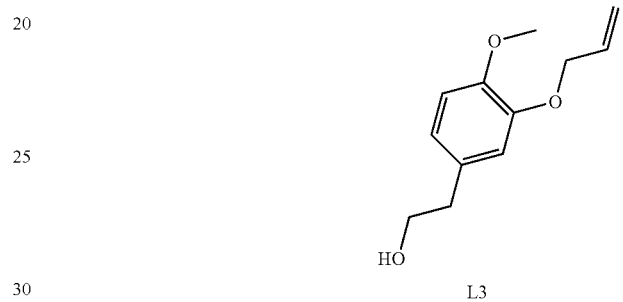

-continued

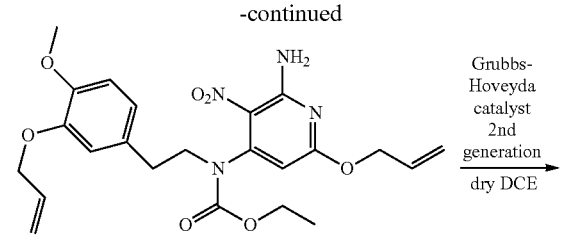

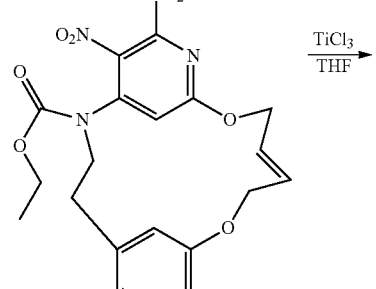

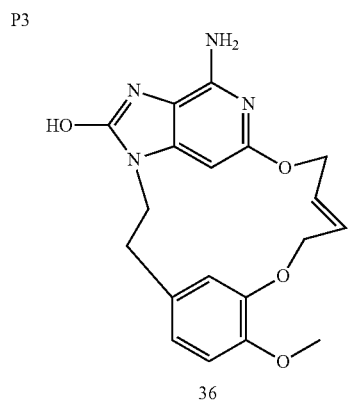

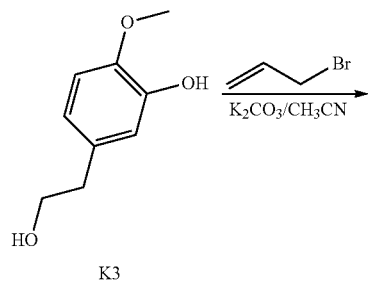

Synthesis of Intermediate L3

Allyl bromide (1.7 mL; 19.6 mmol) was added to a solution of K3 (3 g; 17.8 mmol) and $K_2CO_3$ (2.7 g; 19.6 mmol) in $CH_3CN$ (90 ml). The mixture was stirred at 90° C. for 20 h, and then filtered. The filtrate was concentrated under vacuum. The crude product was taken up with $CH_2Cl_2$ and an aqueous solution of NaOH 5%. The layers were separated and the organic layer was dried over $MgSO_4$, filtered and the solvent was removed under reduced pressure to give 3.9 g of intermediate L3 (quantitative yield). The crude compound was used directly in the next reaction step.

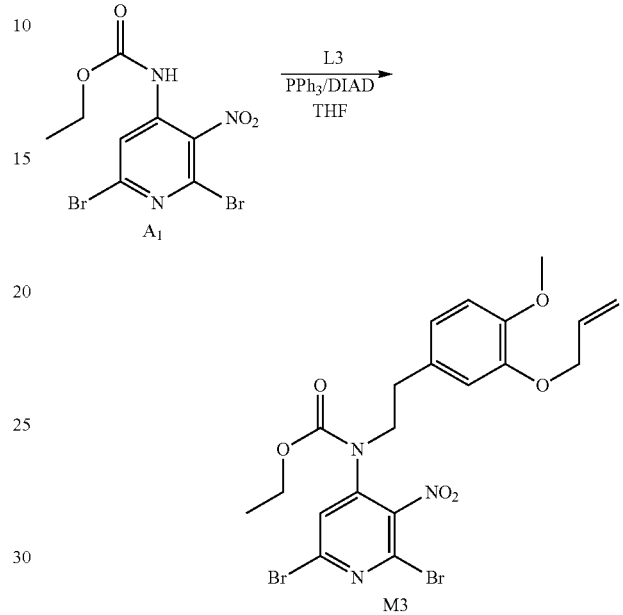

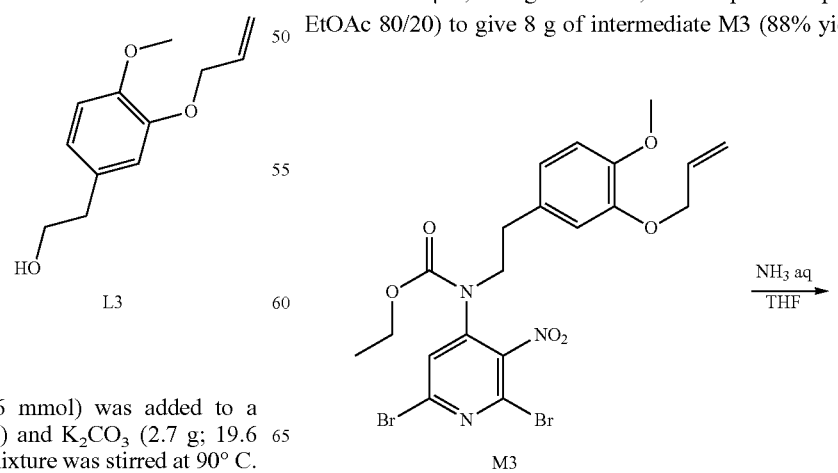

Synthesis of Intermediate M3

At 0° C., diisopropylazodicarboxylate (4.8 mL; 24.36 mmol) was added drop wise to a mixture of A1 (6 g; 16.2 mmol), L3 (3.2 g; 15.36 mmol) and $PPh_3$ (6.4 g; 24.36 mmol) in THF (120 mL). The mixture was stirred at rt for 12 h. EtOAc and water were added. The layers were decanted. The organic layer was washed with water, dried over $MgSO_4$, filtered and the solvent was evaporated. 20 mL of Heptane/AcOEt 70/30 were added to precipitate a large part of the formed $PPh_3O$, which was removed by filtration. The crude product was purified by preparative LC (Irregular SiOH 15-40 μm, 120 g Interchim, mobile phase Heptane/EtOAc 80/20) to give 8 g of intermediate M3 (88% yield).

-continued

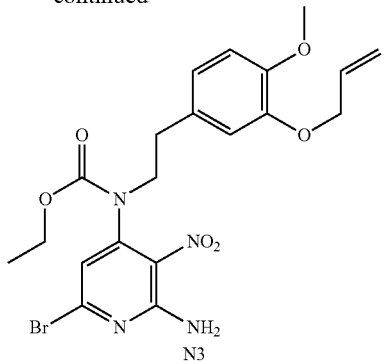

Synthesis of Intermediate N3

M3 (8.8 g; 15.7 mmol) was stirred in THF (120 mL) and NH$_4$OH (120 mL) at rt for 24 h. The mixture was concentrated under reduced pressure. The residue was taken up with CH$_2$Cl$_2$, the precipitate (mineral) was filtered off and the filtrate was dried over MgSO$_4$, filtered through a pad of celite and concentrated under vacuum. The crude product was purified by preparative LC (Irregular SiOH 15-40 µm, 120 g Interchim, mobile phase Heptane/EtOAc 80/20) to afford 3 g of intermediate N3 (38% yield).

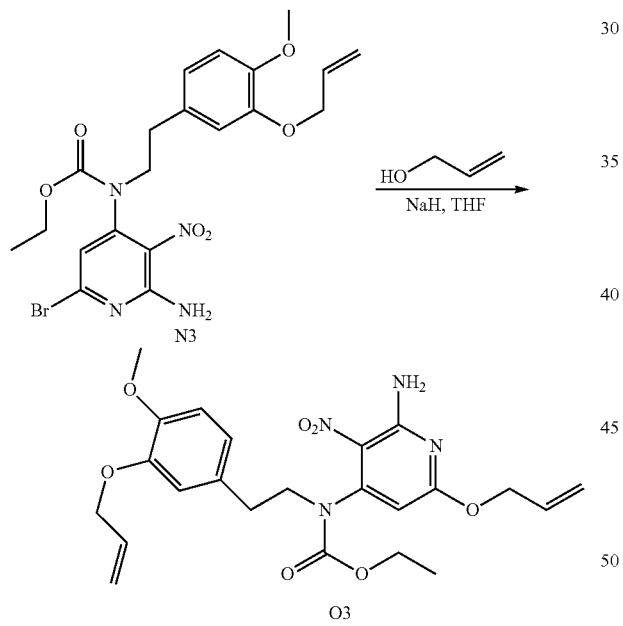

Synthesis of Intermediate O3

NaH (60% in oil) (0.93 g; 23 mmol) was added portion wise to allyl alcohol (28 mL) at rt. The mixture was stirred at rt for 30 min before being added drop wise to a solution of N3 (2.9 g; 5.85 mmol) in THF (70 mL) at 0° C. The resulting mixture was then stirred at rt for 2 h 30 min and was poured into a saturated aqueous solution of NH$_4$Cl. EtOAc and a saturated aqueous solution of NaCl were added, the layers were separated and the aqueous layer was extracted with EtOAc (once). The combined organic layers were dried over MgSO$_4$, filtered and the solvent was removed under reduced pressure to give a yellow oil. The crude product was purified by preparative LC (Irregular SiOH 15-40 µm, 120 g Grace, liquid injection, mobile phase heptane/EtOAc 80/20) to give 2.4 g of intermediate O3 (87% yield).

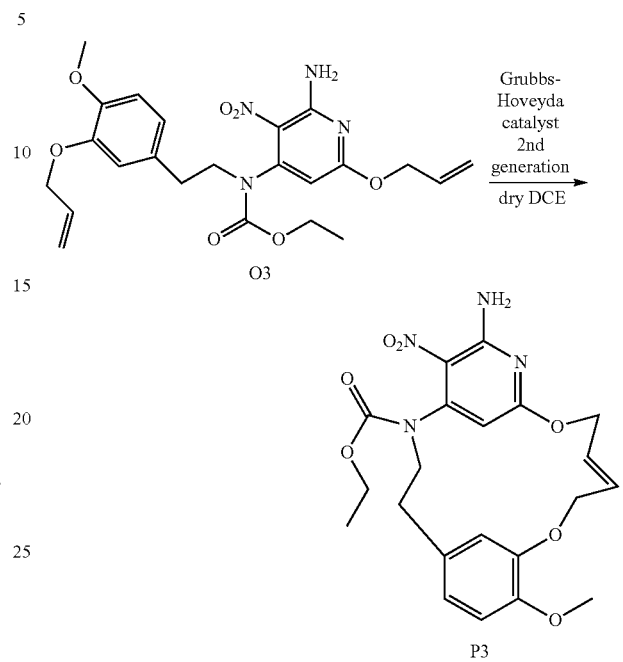

Synthesis of Intermediate P3

The reaction was carried out on three batches.

A solution of O3 (0.8 g; 1.7 mmol) and chlorodicyclohexylborane (1M in hexane) (0.68 mL; 0.68 mmol) in dry dichloroethane (400 mL) was stirred at 80° C. and under N$_2$ atmosphere for 1 h. The mixture was degassed by N$_2$ bubbling for 15 min, Grubbs-Hoveyda catalyst 2$^{nd}$ generation (110 mg; 0.17 mol) was added, the mixture was degassed again by N$_2$ bubbling for 15 min and then stirred at 120° C. for 16 h. 0.050 eq of catalyst (49 mg, 0.084 mmol) were added and mixture was stirred at 120° C. for 7 h. Siliabond DMT (3.3 g; 2.03 mmol) was added and the mixture was stirred rt for 16 h. The mixture was filtered through a pad of celite and the filtrate was concentrated under vacuum to give a black oil. The crude product was purified by preparative LC (Irregular SiOH 15-40 µm, 80 g Interchim, mobile phase Heptane/EtOAc 65/35) to give 190 mg of intermediate P3 (isomer E, 25% yield).

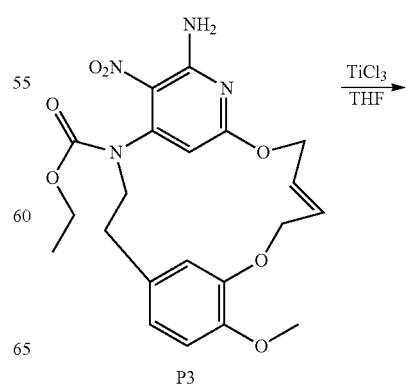

-continued

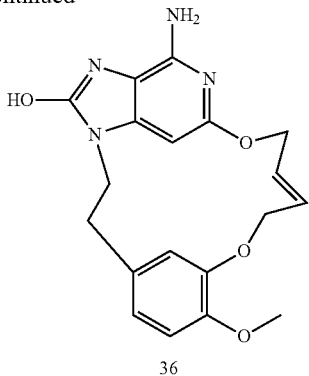

36

Synthesis of Final Compound 36

At rt, TiCl$_3$ (19.3 mL; 22.5 mmol) was added drop wise to a mixture of P3 (500 mg; 1.125 mmol) in THF (90 mL). The mixture was stirred at rt for 2 h. At 0° C., the mixture was basified with K$_2$CO$_3$ powder. The resulting muddy mixture was filtered through a pad of celite and celite was washed with a solution of CH$_2$Cl$_2$/CH$_3$OH (90/10). The filtrate was concentrated under reduced pressure. The residue was taken up in MeOH. The white solid was filtered off and dried under vacuum. The product was purified by preparative LC (Irregular SiOH 15-40 µm, 40 g Interchim, mobile phase CH$_2$Cl$_2$/CH$_3$OH/NH$_4$OH 98/2/0.1) to give 140 mg of final compound 36 (34% yield).

LCMS Methods:

General Procedure VDR2 (For Methods V300xV30xx.olp)

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method V3018V3001

In addition to the general procedure VDR2: Reversed phase UPLC was carried out on a Waters Acquity BEH (bridged ethylsiloxane/silica hybrid) C18 column (1.7 nm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 µl was used. Cone voltage was 20V for positive and negative ionization mode. Mass spectra were acquired by scanning from 100 to 1000 in 0.2 seconds using an interscan delay of 0.1 seconds.

TABLE 1

Compounds of formula (I).

| # | STRUCTURE | Exact Mass | Mass Found [M + H] | LCMS Ret Time, Method | Synthesis method | NMR |
|---|-----------|------------|--------------------|-----------------------|------------------|-----|
| 1 | 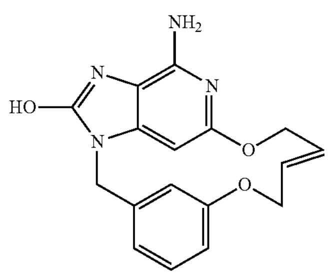 [SMILES: Nc1nc2cc3c1nc(O)n3Cc1cccc(c1)OC/C=C/CO2] | 324.1 | 325 | 1.96, V3018V3001 | Method 1 | $^1$H NMR (500 MHz, DMSO-d$_6$) δ 10.06 (s, 1H), 7.36 (s, 1H), 7.20 (t, J = 7.9 Hz, 1H), 6.76-6.93 (m, 2H), 6.05 (s, 1H), 5.94 (dt, J = 6.0, 16.1 Hz, 1H), 5.43-5.64 (m, 3H), 4.84 (s, 2H), 4.40-4.66 (m, 4H) |
| 2 | 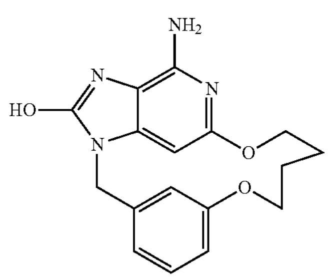 [SMILES: Nc1nc2cc3c1nc(O)n3Cc1cccc(c1)OCCCCO2] | 326.1 | 327 | 2.02, V3018V3001 | Method 2 | $^1$H NMR (400 MHz, DMSO-d$_6$) δ 10.04 (br. s., 1H), 7.49 (s, 1H), 7.17 (t, J = 7.9 Hz, 1H), 6.69-6.83 (m, 2H), 6.15 (s, 1H), 5.54 (s, 2H), 4.89 (s, 2H), 4.28 (t, J = 6.3 Hz, 2H), 4.14 (t, J = 6.6 Hz, 2H), 1.34-1.62 (m, 4H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 3 | 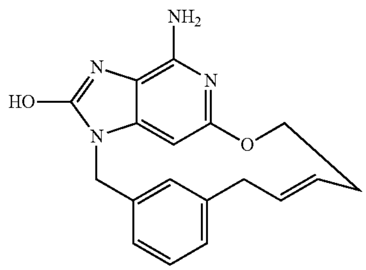 | 322.1 | 323 | 2.3, V3018V3001 | Method 3 | ¹H NMR (500 MHz, DMSO-d₆) δ 10.11 (br. s., 1H), 7.22 (t, J = 7.6 Hz, 1H), 7.12 (br. s., 1H), 7.09 (d, J = 7.6 Hz, 1H), 7.05 (d, J = 7.6 Hz, 1H), 5.74 (s, 1H), 5.51-5.63 (m, 3H), 5.03 (td, J = 7.2, 14.9 Hz, 1H), 4.93 (s, 2H), 4.15-4.26 (m, 2H), 3.15-3.23 (m, 2H), 2.24-2.33 (m, 2H) |
| 4 | 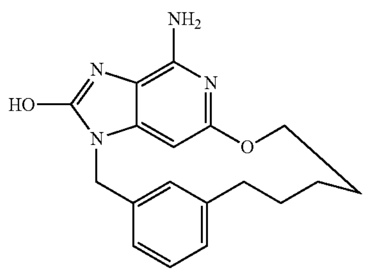 | 324.2 | 325 | 2.36, V3018V3001 | Method 4 | ¹H NMR (500 MHz, DMSO-d₆) δ 10.20 (br. s., 1H), 7.34 (s, 1H), 7.21 (t, J = 7.3 Hz, 1H), 7.06 (d, J = 7.3 Hz, 1H), 6.97 (d, J = 7.3 Hz, 1H), 5.59 (s, 2H), 4.93 (s, 2H), 3.91-4.03 (m, 2H), 2.55-2.62 (m, 2H), 1.59-1.71 (m, 2H), 1.12-1.27 (m, 4H) |
| 5 | 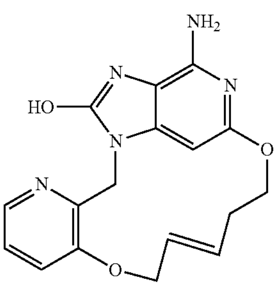 [SMILES: Nc1nc2cc3c1nc(O)n3Cc1ncccc1OC/C=C/CCO2] | 339.1 | 340 | 1.85, V3018V3001 | Method 5 | ¹H NMR (400 MHz, DMSO-d₆) δ 9.91 (br. s., 1H), 8.05 (d, J = 4.6 Hz, 1H), 7.38 (d, J = 8.6 Hz, 1H), 7.27 (dd, J = 4.6, 8.6 Hz, 1H), 6.20 (s, 1H), 5.82 (dt, J = 7.0, 15.6 Hz, 1H), 5.68 (dt, J = 7.1, 15.6 Hz, 1H), 5.46 (s, 2H), 4.91 (s, 2H), 4.33 (d, J = 7.1 Hz, 2H), 4.12-4.27 (m, 2H), 2.36-2.46 (m, 2H) |
| 6 | 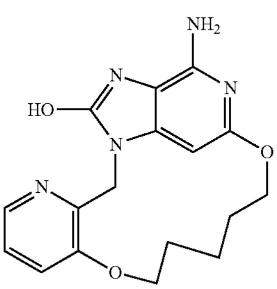 [SMILES: Nc1nc2cc3c1nc(O)n3Cc1ncccc1OCCCCCO2] | 341.1 | 342 | 1.85, V3018V3001 | Method 6 | ¹H NMR (400 MHz, DMSO-d₆) δ 9.92 (s, 1H), 8.09 (d, J = 4.0 Hz, 1H), 7.43 (d, J = 8.1 Hz, 1H), 7.30 (dd, J = 4.0, 8.1 Hz, 1H), 6.40 (s, 1H), 5.51 (s, 2H), 4.96 (s, 2H), 4.15 (t, J = 6.1 Hz, 2H), 3.97-4.10 (m, 2H), 1.81-1.91 (m, 2H), 1.68-1.78 (m, 2H), 1.52-1.65 (m, 2H) |
| 7 | 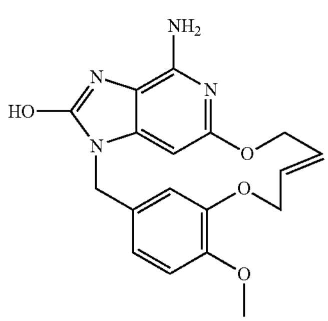 | 354.1 | 355 | 1.84, V3018V3001 | Method 1 | ¹H NMR (400 MHz, DMSO-d₆) δ 10.03 (br. s., 1H), 7.36 (d, J = 2.0 Hz, 1H), 6.91 (d, J = 8.1 Hz, 1H), 6.80 (dd, J = 2.0, 8.1 Hz, 1H), 6.06 (dt, J = 6.0, 16.2 Hz, 1H), 5.93 (s, 1H), 5.54 (s, 2H), 5.41 (dt, J = 5.6, 16.2 Hz, 1H), 4.78 (s, 2H), 4.50-4.67 (m, 2H), 4.28-4.48 (m, 2H), 3.71 (s, 3H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 8 | 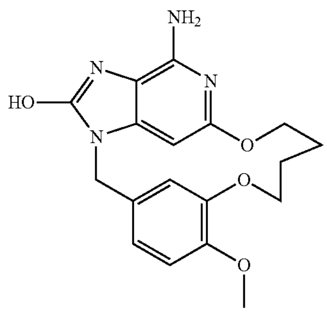 [SMILES: COc1ccc2cc1OC/C=C/COc1cc3c(nc(O)n3C2)c(N)n1] | 356.1 | 357 | 1.86, V3018V3001 | Method 2 | $^1$H NMR (400 MHz, DMSO-d$_6$) δ 10.03 (br. s., 1H), 7.54 (br. s., 1H), 6.87 (d, J = 8.1 Hz, 1H), 6.76 (d, J = 8.1 Hz, 1H), 6.24 (br. s., 1H), 5.53 (br. s., 2H), 4.82 (br. s., 2H), 4.19-4.32 (m, 2H), 4.01-4.16 (m, 2H), 3.68 (br. s., 3H), 1.34-1.60 (m, 4H) |
| 9 | 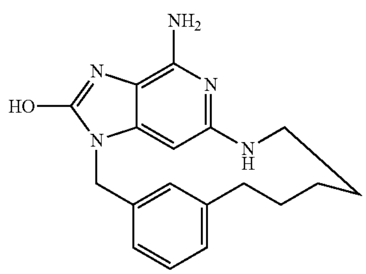 | 323.2 | 324 | 2.36, V3018V3001 | Method 1 Method 2 | $^1$H NMR (400 MHz, DMSO-d$_6$) δ 9.73 (s, 1H), 7.57 (s, 1H), 7.16 (t, J = 7.6 Hz, 1H), 7.02 (d, J = 7.6 Hz, 1H), 6.89 (d, J = 7.6 Hz, 1H), 5.33 (t, J = 6.6 Hz, 1H), 5.25 (s, 1H), 5.15 (s, 2H), 4.85 (s, 2H), 2.91 (q, J = 6.6 Hz, 2H), 2.58-2.72 (m, 2H), 1.59-1.85 (m, 2H), 0.96-1.21 (m, 4H) |
| 10 | 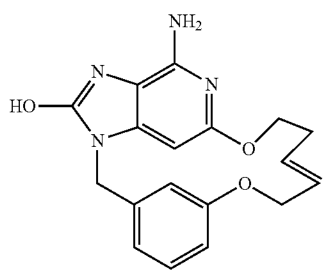 [SMILES: Nc1nc2cc3c1nc(O)n3Cc1cccc(c1)OC/C=C/CCO2] | 338.1 | 339 | 2.22, V3018V3001 | Method 7 | $^1$H NMR (400 MHz, DMSO-d$_6$) δ 10.05 (br. s., 1H), 7.20 (t, J = 7.8 Hz, 1H), 6.92 (d, J = 7.8 Hz, 1H), 6.89 (s, 1H), 6.77 (d, J = 7.8 Hz, 1H), 6.12 (s, 1H), 5.50-5.64 (m, 3H), 5.35 (dt, J = 4.5, 16.2 Hz, 1H), 4.87 (s, 2H), 4.58 (d, J = 4.5 Hz, 2H), 4.24 (t, J = 5.1 Hz, 2H), 2.21-2.32 (m, 2H) |
| 11 | 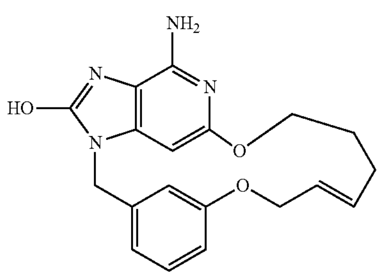 [SMILES: Nc1nc2cc3c1nc(O)n3Cc1cccc(c1)OC/C=C/CCCO2] | 352.2 | 353 | 2.33, V3018V3001 | Method 1 | $^1$H NMR (500 MHz, DMSO-d$_6$) δ 10.07 (s, 1H), 7.32 (s, 1H), 7.18 (t, J = 7.7 Hz, 1H), 6.82 (d, J = 7.7 Hz, 1H), 6.79 (dd, J = 1.7, 7.7 Hz, 1H), 5.98 (dt, J = 7.7, 15.5 Hz, 1H), 5.80 (s, 1H), 5.56 (s, 2H), 5.51 (td, J = 5.8, 15.5 Hz, 1H), 4.84 (s, 2H), 4.71 (d, J = 5.8 Hz, 2H), 3.96 (t, J = 7.7 Hz, 2H), 1.92-2.07 (m, 2H), 1.49-1.64 (m, 2H) |
| 12 | 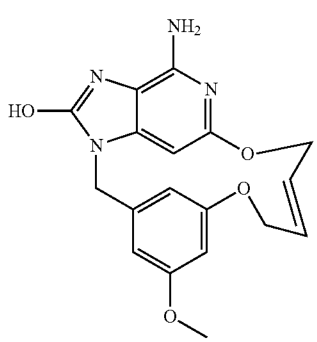 [SMILES: COc1cc2cc(c1)OC/C=C/COc1cc3c(nc(O)n3C2)c(N)n1] | 354.1 | 355 | 2.04, V3018V3001 | Method 1 | $^1$H NMR (400 MHz, DMSO-d$_6$) δ 10.05 (br. s., 1H), 6.94 (s, 1H), 6.47 (s, 1H), 6.39 (s, 1H), 6.05 (s, 1H), 5.87 (dt, J = 6.0, 15.7 Hz, 1H), 5.45-5.68 (m, 3H), 4.79 (s, 2H), 4.41-4.61 (m, 4H), 3.64 (s, 3H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 13 | 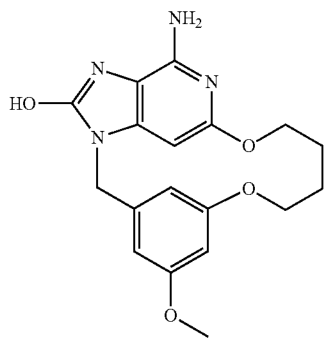 [SMILES: COc1cc2cc(c1)OCCCCOc1cc3c(nc(O)n3C2)c(N)n1] | 356.1 | 357 | 2.1, V3018V3 001 | Method 2 | $^1$H NMR (500 MHz, DMSO-d$_6$) δ 10.05 (s, 1H), 7.08 (s, 1H), 6.24-6.44 (m, 2H), 6.16 (s, 1H), 5.55 (s, 2H), 4.84 (s, 2H), 4.25 (t, J = 6.3 Hz, 2H), 4.13 (t, J = 6.8 Hz, 2H), 3.64 (s, 3H), 1.47-1.62 (m, 2H), 1.29-1.46 (m, 2H) |
| 14 | 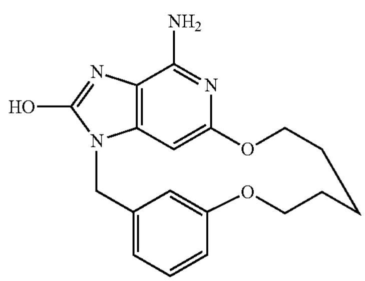 [SMILES: Nc1nc2cc3c1nc(O)n3Cc1cccc(c1)OCCCCCO2] | 340.2 | 341 | 2.23, V3018V3 001 | Method 8 | $^1$H NMR (400 MHz, DMSO-d$_6$) δ 10.06 (s, 1H), 7.10-7.30 (m, 2H), 6.89 (d, J = 7.6 Hz, 1H), 6.81 (dd, J = 2.0, 7.6 Hz, 1H), 6.25 (s, 1H), 5.58 (s, 2H), 4.86 (s, 2H), 3.99-4.12 (m, 4H), 1.33-1.51 (m, 6H) |
| 15 | 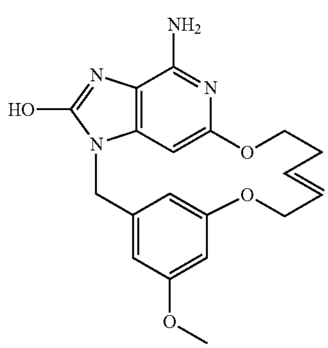 [SMILES: COc1cc2cc(c1)OC/C=C/CCOc1cc3c(nc(O)n3C2)c(N)n1] | 368.1 | 369 | 2.25, V3018V3 001 | Method 9 | $^1$H NMR (400 MHz, DMSO-d$_6$) δ 10.07 (s, 1H), 6.52 (s, 1H), 6.45 (s, 1H), 6.33 (s, 1H), 6.09 (s, 1H), 5.46-5.68 (m, 3H), 5.34 (dt, J = 5.2, 15.9 Hz, 1H), 4.83 (s, 2H), 4.54 (d, J = 5.2 Hz, 2H), 4.24 (t, J = 5.3 Hz, 2H), 3.68 (s, 3H), 2.21-2.31 (m, 2H) |
| 16 | 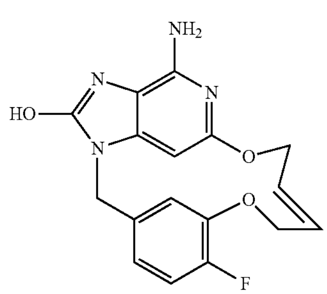 [SMILES: Nc1nc2cc3c1nc(O)n3Cc1ccc(F)c(c1)OC/C=C/CO2] | 342.1 | 343 | 2.04, V3018V3 001 | Method 10 | $^1$H NMR (500 MHz, DMSO-d$_6$) δ 10.13 (br. s., 1H), 7.58 (dd, J = 1.7, 7.9 Hz, 1H), 7.14 (dd, J = 8.3, 10.9 Hz, 1H), 6.73-6.94 (m, 1H), 5.88-6.13 (m, 2H), 5.41-5.75 (m, 3H), 4.83 (s, 2H), 4.61 (d, J = 5.4 Hz, 2H), 4.56 (d, J = 6.3 Hz, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 17 | 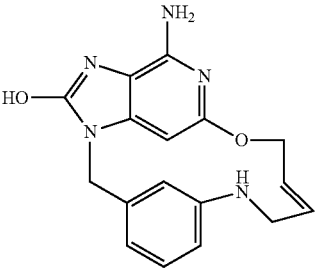 [SMILES: Nc1nc2cc3c1nc(O)n3Cc1cccc(c1)NC/C=C/CO2] | 342.1 | 343 | 2.04, V3018V3001 | Method 10 | $^1$H NMR (500 MHz, DMSO-$d_6$) δ 11.15 (br. s., 1H), 7.70 (dd, J = 1.9, 7.9 Hz, 1H), 6.96-7.53 (m, 2H), 6.80-6.93 (m, 1H), 6.37 (s, 1H), 6.24 (dt, J = 6.3, 15.8 Hz, 1H), 5.63 (dt, J = 5.9, 15.8 Hz, 1H), 4.77-4.99 (m, 4H), 4.58 (d, J = 6.3 Hz, 2H) |
| 18 | 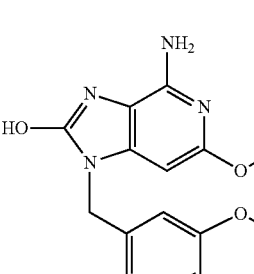 | 323.1 | 324 | 1.78, V3018V3001 | Method 11 | $^1$H NMR (500 MHz, DMSO-$d_6$) δ 10.01 (s, 1H), 6.93 (t, J = 7.7 Hz, 1H), 6.74 (br. s., 1H), 6.40-6.58 (m, 2H), 6.30 (s, 1H), 6.02 (br. s., 1H), 5.83 (dt, J = 5.4, 16.0 Hz, 1H), 5.58 (br. s., 2H), 5.36-5.50 (m, 1H), 4.74 (s, 2H), 4.49 (d, J = 5.4 Hz, 2H), 3.56-3.87 (m, 2H) |
| 19 | 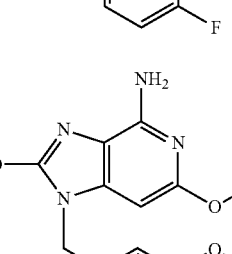 | 358.1 | 359 | 2.27, V3018V3001 | Method 14 | $^1$H NMR (500 MHz, DMSO-$d_6$) δ 9.49 (br. s, 1H), 7.44 (d, J = 7.9 Hz, 1H), 7.14 (dd, J = 8.2, 11.4 Hz, 1H), 6.84-6.97 (m, 1H), 6.34 (s, 1H), 5.69 (s, 2H), 4.84 (s, 2H), 4.03-4.17 (m, 4H), 1.31-1.57 (m, 6H) |
| 20 | 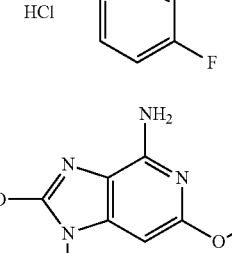 | 358.1 | 359 | 2.27, V3018V3001 | Method 14 | $^1$H NMR (500 MHz, DMSO-$d_6$) δ 11.04 (br. s., 1H), 7.46 (dd, J = 1.9, 8.2 Hz, 1H), 6.86-7.32 (m, 3H), 6.78 (s, 1H), 4.94 (s, 2H), 4.41 (t, J = 6.6 Hz, 2H), 4.09 (t, J = 6.9 Hz, 2H), 1.63-1.73 (m, 2H), 1.53-1.62 (m, 2H), 1.36-1.49 (m, 2H) |
| 21 | 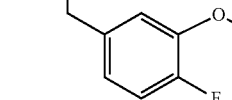 | 356.1 | 357 | 2.21, V3018V3001 | Method 13 | $^1$H NMR (500 MHz, DMSO-$d_6$) δ 10.09 (br. s., 1H), 6.99-7.23 (m, 2H), 6.92 (br. s., 1H), 6.15 (s, 1H), 5.53-5.73 (m, 3H), 5.23-5.48 (m, 1H), 4.85 (s, 2H), 4.67 (d, J = 4.4 Hz, 2H), 4.24 (t, J = 4.6 Hz, 2H), 2.21-2.35 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 22 | (structure: 4-amino-2-hydroxy-imidazopyridine with N-benzyl bearing 3-O-CH2-CH=CH-CH2-O linkage to 4-fluorophenyl, HCl salt) | 356.1 | 357 | 2.21, V3018V3001 | Method 13 | $^1$H NMR (500 MHz, DMSO-$d_6$) δ 11.11 (br. s., 1H), 7.10-7.42 (m, 3H), 7.07 (dd, J = 1.9, 8.2 Hz, 1H), 6.85-6.99 (m, 1H), 6.64 (s, 1H), 5.80 (dt, J = 7.2, 15.6 Hz, 1H), 5.59 (dt, J = 5.7, 15.6 Hz, 1H), 4.98 (s, 2H), 4.68 (d, J = 5.7 Hz, 2H), 4.41-4.59 (m, 2H), 2.38-2.50 (m, 2H) |
| 23 | (structure: 4-amino-2-hydroxy-imidazopyridine with macrocycle via O-(CH2)4-NH to 3-substituted phenyl-CH2-N) | 325.2 | 326 | 1.83, V3018V3001 | Method 12 | $^1$H NMR (500 MHz, DMSO-$d_6$) δ 9.97 (br. s., 1H), 7.05 (s, 1H), 6.90 (t, J = 7.7 Hz, 1H), 6.42 (d, J = 7.7 Hz, 1H), 6.38 (d, J = 7.7 Hz, 1H), 6.35 (s, 1H), 5.33-5.58 (m, 3H), 4.77 (s, 2H), 4.17 (t, J = 6.8 Hz, 2H), 3.20 (q, J = 6.4 Hz, 2H), 1.42-1.52 (m, 2H), 1.32-1.41 (m, 2H) |
| 24 | (structure: 4-amino-2-hydroxy-imidazopyridine with macrocycle O-(CH2)4-O to 4-fluorophenyl-CH2-N) | 344.1 | 345 | 2.08, V3018V3001 | Method 14 | $^1$H NMR (500 MHz, DMSO-$d_6$) δ 10.04 (br. s., 1H), 7.77 (d, J = 7.6 Hz, 1H), 7.10 (dd, J = 8.7, 11.2 Hz, 1H), 6.78 (br. s., 1H), 6.28 (s, 1H), 5.56 (s, 2H), 4.86 (s, 2H), 4.28-4.47 (m, 2H), 4.04-4.23 (m, 2H), 1.52-1.66 (m, 2H), 1.31-1.50 (m, 2H) |
| 25 | (structure: 4-amino-2-hydroxy-imidazopyridine with macrocyclic O-CH2-CH=CH-CH2-O linkage to phenyl-CH2-N) | 338.1 | 339 | 2.13, V3018V3001 | Method 15 | $^1$H NMR (500 MHz, DMSO-$d_6$) δ 10.07 (br. s., 1H), 7.18 (t, J = 7.9 Hz, 1H), 7.14 (s, 1H), 6.73-6.87 (m, 2H), 5.96 (dt, J = 5.0, 15.7 Hz, 1H), 5.90 (s, 1H), 5.57 (s, 2H), 5.37 (dt, J = 5.8, 15.7 Hz, 1H), 4.86 (s, 2H), 4.58 (d, J = 5.8 Hz, 2H), 4.22 (t, J = 5.0 Hz, 2H), 2.27-2.42 (m, 2H) |
| 26 | (structure: 4-amino-2-hydroxy-imidazopyridine with macrocyclic O-CH2-CH=CH-CH2-NH linkage to phenyl-CH2-N) | 337.2 | 338 | 2.02, V3018V3001 | Method 16 | $^1$H NMR (500 MHz, DMSO-$d_6$) δ 10.04 (br. s., 1H), 6.95 (t, J = 7.2 Hz, 1H), 6.51 (d, J = 7.2 Hz, 1H), 6.46 (dd, J = 1.3, 7.2 Hz, 1H), 6.40 (s, 1H), 6.16 (s, 1H), 5.97 (t, J = 6.3 Hz, 1H), 5.59 (s, 2H), 5.43 (dt, J = 6.3, 15.5 Hz, 1H), 5.22 (dt, J = 5.0, 15.5 Hz, 1H), 4.76 (s, 2H), 4.23 (t, J = 5.2 Hz, 2H), 3.56 (t, J = 5.0 Hz, 2H), 2.18-2.30 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 27 | 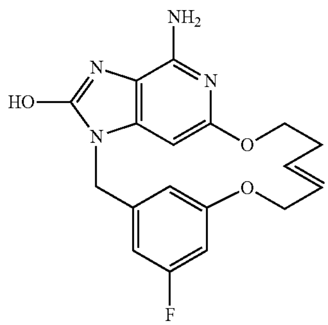 [SMILES: Nc1nc2cc3c1nc(O)n3Cc1cc(F)cc(c1)OC/C=C/CCO2] | 356.1 | 357 | 2.30, V3018V3001 | Method 17 | $^1$H NMR (500 MHz, DMSO-d$_6$) δ 10.11 (br. s., 1H), 6.77 (d, J = 9.1 Hz, 1H), 6.71 (s, 1H), 6.63 (dt, J = 2.2, 9.1 Hz, 1H), 6.15 (s, 1H), 5.64 (s, 2H), 5.57 (dt, J = 6.6, 15.8 Hz, 1H), 5.34 (dt, J = 5.3, 15.8 Hz, 1H), 4.89 (s, 2H), 4.59 (d, J = 4.7 Hz, 2H), 4.25 (t, J = 5.3 Hz, 2H), 2.20-2.34 (m, 2H) |
| 28 | 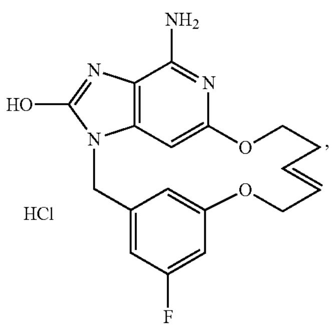 [SMILES: Nc1nc2cc3c1nc(O)n3Cc1cc(F)cc(c1)OC/C=C/CCO2 ; Cl] | 356.1 | 357 | 2.31, V3018V3001 | Method 17 | $^1$H NMR (500 MHz, DMSO-d$_6$) δ 11.09 (br. s., 1H), 7.15 (br. s., 2H), 6.82 (d, J = 8.8 Hz, 1H), 6.56-6.70 (m, 3H), 5.71 (d, J = 6.3, 15.6 Hz, 1H), 5.52 (dt, J = 5.4, 15.6 Hz, 1H), 4.99 (s, 2H), 4.62 (d, J = 5.4 Hz, 2H), 4.50 (t, J = 4.7 Hz, 2H), 2.42-2.47 (m, 2H) |
| 29 | 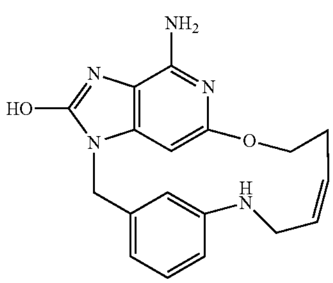 [SMILES: Nc1nc2cc3c1nc(O)n3Cc1cccc(c1)NC/C=C\CCO2] | 337.2 | 338 | 2.05, V3018V3001 | Method 16 | $^1$H NMR (500 MHz, DMSO-d$_6$) δ 10.08 (br. s., 1H), 6.96 (t, J = 7.7 Hz, 1H), 6.45-6.57 (m, 2H), 6.42 (s, 1H), 6.20 (s, 1H), 5.92 (t, J = 6.0 Hz, 1H), 5.65 (s, 2H), 5.31-5.48 (m, 1H), 5.08-5.26 (m, 1H), 4.75 (s, 2H), 4.31 (t, J = 5.8 Hz, 2H), 3.41-3.48 (m, 2H), 2.12-2.28 (m, 2H) |
| 30 | 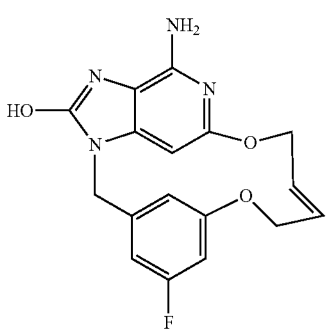 [SMILES: Nc1nc2cc3c1nc(O)n3Cc1cc(F)cc(c1)OC/C=C/CO2] | 342.1 | 343 | 2.08, V3018V3001 | Method 19 | $^1$H NMR (500 MHz, DMSO-d$_6$) δ 10.10 (br. s., 1H), 7.23 (s, 1H), 6.78 (d, J = 8.8 Hz, 1H), 6.62 (d, J = 8.8 Hz, 1H), 6.08 (s, 1H), 5.84 (dt, J = 5.0, 15.8 Hz, 1H), 5.71 (dt, J = 5.0, 15.8 Hz, 1H), 5.60 (s, 2H), 4.86 (s, 2H), 4.63 (d, J = 5.0 Hz, 2H), 4.54 (d, J = 5.0 Hz, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 31 | 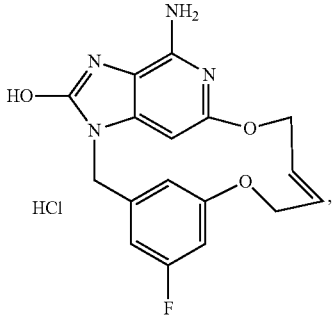 [SMILES: Nc1nc2cc3c1nc(O)n3Cc1cc(F)cc(c1)OC/C=C/CO2 ; Cl] | 342.1 | 343 | 2.08, V3018V3001 | Method 19 | ¹H NMR (500 MHz, DMSO-d$_6$) δ 11.12 (br. s., 1H), 7.34 (s, 1H), 7.15 (br, s., 2H), 6.85 (d, J = 10.4 Hz, 1H), 6.64 (d, J = 10.4 Hz, 1H), 6.44 (s, 1H), 6.07 (dt, J = 5.9, 15.8 Hz, 1H), 5.70 (dt, J = 5.9, 15.8 Hz, 1H), 4.95 (s, 2H), 4.84 (d, J = 5.9 Hz, 2H), 4.64 (d, J = 5.9 Hz, 2H) |
| 32 | 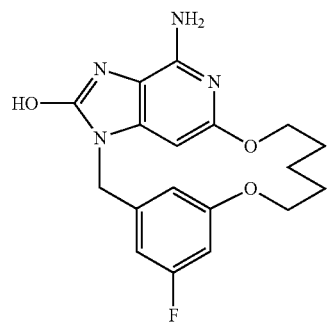 | 358.1 | 359 | 2.32, V3018V3001 | Method 18 | ¹H NMR (500 MHz, DMSO-d$_6$) δ 10.13 (br. s., 1H), 7.05 (s, 1H), 6.71 (d, J = 9.1 Hz, 1H), 6.67 (d, J = 9.1 Hz, 1H), 6.28 (s, 1H), 5.63 (s, 2H), 4.87 (s, 2H), 3.85-4.18 (m, 4H), 1.21-1.59 (m, 6H) |
| 33 | 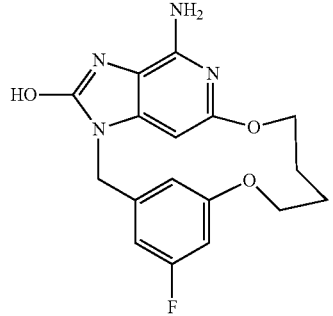 [SMILES: Nc1nc2cc3c1nc(O)n3Cc1cc(F)cc(c1)OCCCCO2] | 344.1 | 345 | 2.14, V3018V3001 | Method 14 | ¹H NMR (500 MHz, DMSO-d$_6$) δ 10.09 (br. s., 1H), 7.33 (s, 1H), 6.66 (d, J = 9.1 Hz, 1H), 6.59 (d, J = 9.1 Hz, 1H), 6.17 (s, 1H), 5.58 (s, 2H), 4.90 (s, 2H), 4.29 (t, J = 6.5 Hz, 2H), 4.15 (t, J = 6.5 Hz, 2H), 1.48-1.59 (m, 2H), 1.36-1.46 (m, 2H) |
| 34 | 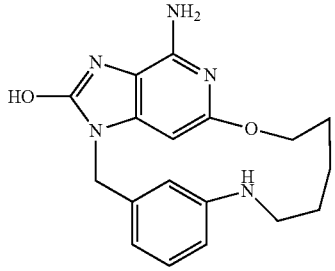 [SMILES: Nc1nc2cc3c1nc(O)n3Cc1cccc(c1)NCCCCCO2] | 339.2 | 340 | 2.06, V3018V3001 | Method 12 | ¹H NMR (500 MHz, DMSO-d$_6$) δ 10.05 (s, 1H), 6.83-7.00 (m, 1H), 6.62 (s, 1H), 6.50 (d, J = 8.2 Hz, 1H), 6.43 (dd, J = 1.6, 8.2 Hz, 1H), 6.36 (s, 1H), 5.72 (t, J = 6.6 Hz, 1H), 5.60 (s, 2H), 4.76 (s, 2H), 4.07 (t, J = 5.7 Hz, 2H), 2.95 (q, J = 6.6 Hz, 2H), 1.12-1.50 (m, 8H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 35 | (structure) | 338.1 | 339 | 1.97, V3018V3001 | Method 20 | $^1$H NMR (500 MHz, DMSO-$d_6$) δ 9.92 (br. s., 1H), 6.81-7.02 (m, 2H), 6.73 (d, J = 8.2 Hz, 1H), 6.38 (d, J = 8.2 Hz, 1H), 5.91 (dt, J = 4.4, 16 Hz, 1H), 5.38-5.57 (m, 3H), 5.33 (s, 1H), 4.65 (d, J = 4.4 Hz, 2H), 4.54 (d, J = 4.4 Hz, 2H), 3.96 (t, J = 5.2 Hz, 2H), 2.87 (t, J = 5.2 Hz, 2H) |
| 36 | (structure) | 368.1 | 369 | 1.86, V3018V3001 | Method 20 | $^1$H NMR (500 MHz, DMSO-$d_6$) δ 9.92 (br. s., 1H), 7.01 (s, 1H), 6.60 (d, J = 8.2 Hz, 1H), 6.36 (d, J = 8.2 Hz, 1H), 6.02 (dt, J = 5.0, 16 Hz, 1H), 5.46 (s, 2H), 5.28-5.42 (m, 2H), 4.61 (d, J = 5.0 Hz, 2H), 4.52 (d, J = 5.0 Hz, 2H), 3.77-4.04 (m, 2H), 3.65 (s, 3H), 2.70-2.91 (m, 2H) |

Biological Activity of Compounds of Formula (I)

Description of Biological Assays

Assessment of TLR7 and TLR8 Activity

The ability of compounds to activate human TLR7 and TLR8 was assessed in a cellular reporter assay using HEK293 cells transiently transfected with a TLR7 or TLR8 expression vector and NFκB-luc reporter construct. Briefly, HEK293 cells were grown in culture medium (DMEM supplemented with 10% FCS and 2 mM Glutamine) For transfection of cells in 15 cm dishes, cells were detached with Trypsin-EDTA, transfected with a mix of CMV-TLR7 or TLR8 plasmid (1,700 ng), NFκB-luc plasmid (850 ng) and a transfection reagent and incubated 48 hours at 37° C. in a humidified 5% $CO_2$ atmosphere. Transfected cells were then washed in PBS, detached with Trypsin-EDTA, and resuspended in medium to a density of $1.25 \times 10^5$ cells/mL. Forty microliters of cells were then dispensed into each well in 384-well plates, where 200 nL of compound in 100% DMSO was already present. Following 6 hours incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

In parallel, a similar dilution series of compound was used (200 nL of compound in 100% DMSO) with 40 μL per well of cells transfected with NFκB-luc reporter construct alone ($1.25 \times 10^5$ cells/mL). Six hours after incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Counterscreen data is reported as LEC.

Measurement of Interferon Production in Human PBMC

Activation of human TLR7 results in robust production of interferon by plasmacytoid dendritic cells present in human blood. The potential of compounds to induce interferon was evaluated by determination of interferon in the conditioned media from peripheral blood mononuclear cells (PBMC). The presence of interferon in the samples was determined, using an interferon reporter cell line stably expressing an interferon-stimulated responsive elements (ISRE)-luc reporter construct. The ISRE element with sequence TAGTTTCACTTTCCC (SEQ ID NO: 1) is highly responsive to the STAT1-STAT2-IRF9 transcription factor, which becomes activated upon binding of IFN-I to the IFN receptor. Briefly, PBMCs were prepared from buffy coats of at least two donors using a standard Ficoll centrifugation protocol. Isolated PBMCs were resuspended in RPMI medium supplemented with 10% human AB serum and $2 \times 10^5$ cells/well were dispensed into 384-well plates containing compounds (70 μL total volume). After overnight incubation of the PBMCs with the compounds, 10 μL of supernatant was transferred to 384-well plates containing $5 \times 10^3$ HEK-ISRE-luc cells/well in 30 μL (plated the day before). Following 24 hours of incubation, activation of the ISRE elements was measured by assaying luciferase activity using 40 μL/well Steady Lite Plus substrate (Perkin Elmer) and measured with ViewLux ultraHTS microplate imager (Perkin Elmer). The stimulating activity of each compound on the HEK-ISRE-luc cells was reported as LEC. The LEC in turn indicates the degree of ISRE activation on transfer of a defined amount of PBMC culture medium. Recombinant interferon alfa-2a (Roferon-A) was used as a standard control compound.

The LEC values for the compounds in table 2 on HEK293 TLR8-NFκB-luc and HEK293 NFκB-luc where greater than the highest tested concentration (>10 μM for compound 4 and >25 μM for all other compounds).

TABLE 2

| # | STRUCTURE | HEK293 TLR7-NFκB-luc (LEC; μM) | n | PBMC HEK-ISRE-luc (LEC; μM) | n |
|---|---|---|---|---|---|
| 1 | 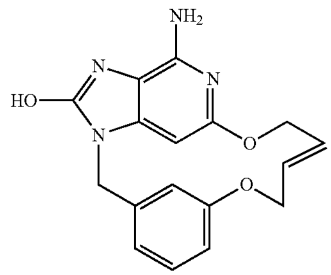 [SMILES: Nc1nc2cc3c1nc(O)n3Cc1cccc(c1)OC/C=C/CO2] | 2.88 | 8 | 0.30 | 8 |
| 2 | 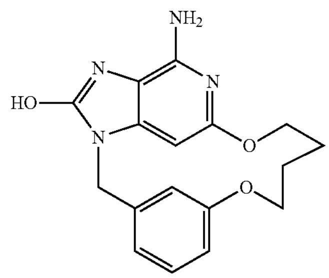 | 4.47 | 1 | 0.93 | 2 |
| 3 | 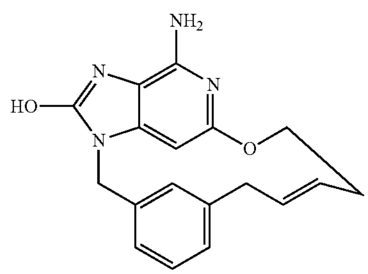 [SMILES: Nc1nc2cc3c1nc(O)n3Cc1cccc(c1)C/C=C/CCO2] | 0.27 | 2 | 0.033 | 4 |
| 4 | 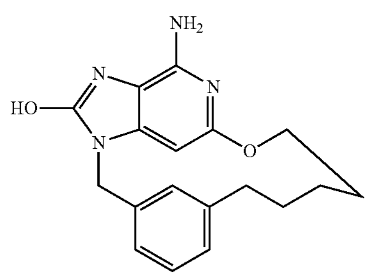 [SMILES: Nc1nc2cc3c1nc(O)n3Cc1cccc(c1)CCCCCO2] | 2.38 | 1 | 2.56 | 2 |
| 5 | 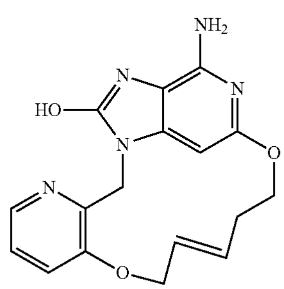 [SMILES: Nc1nc2cc3c1nc(O)n3Cc1ncccc1OC/C=C/CCO2] | 2.14 | 1 | 0.082 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 6 | 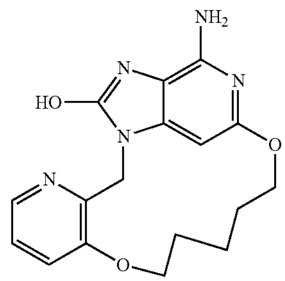 [SMILES: Nc1nc2cc3c1nc(O)n3Cc1ncccc1OCCCCCO2] | 1 | 1 | 0.16 | 2 |
| 7 | 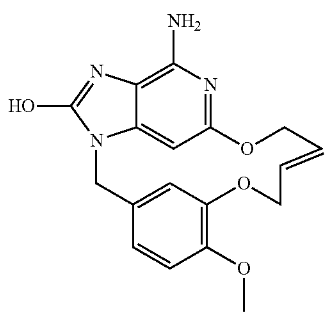 | 3.88 | 1 | 0.29 | 2 |
| 8 | 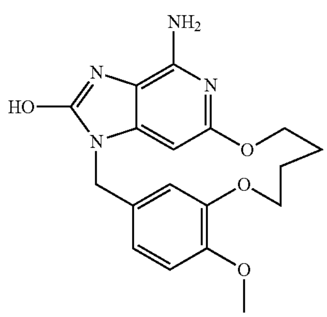 [SMILES: COc1ccc2cc1OC/C=C/COc1cc3c(nc(O)n3C2)c(N)n1] | 7.1 | 1 | 0.58 | 2 |
| 9 | 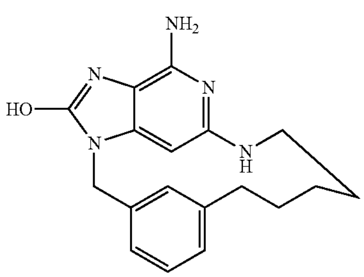 | 11.09 | 1 | 10.87 | 2 |
| 10 | 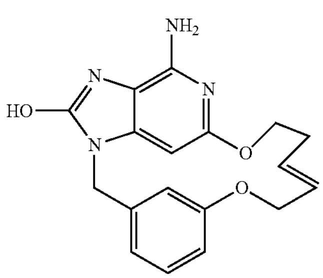 [SMILES: Nc1nc2cc3c1nc(O)n3Cc1cccc(c1)OC/C=C/CCO2] | 0.78 | 2 | 0.25 | 4 |

TABLE 2-continued
Compounds of formula (I)
| # | STRUCTURE | HEK293 TLR7-NFκB-luc (LEC; μM) | n | PBMC HEK-ISRE-luc (LEC; μM) | n |
|---|---|---|---|---|---|
| 11 | 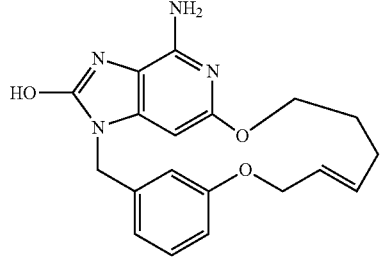 [SMILES: Nc1nc2cc3c1nc(O)n3Cc1cccc(c1)OC/C=C/CCCO2] | 1.25 | 1 | 0.45 | 2 |
| 12 | 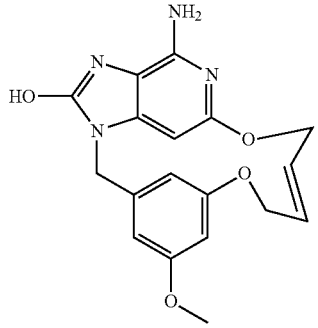 [SMILES: COc1cc2cc(c1)OC/C=C/COc1cc3c(nc(O)n3C2)c(N)n1] | 1.08 | 1 | 0.3 | 2 |
| 13 | 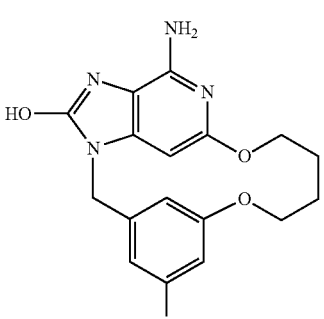 | 1.71 | 2 | 0.15 | 2 |
| 14 | 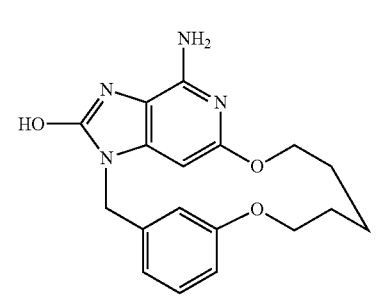 [SMILES: Nc1nc2cc3c1nc(O)n3Cc1cccc(c1)OCCCCCO2] | 7.01 | 2 | 2.4 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 15 | 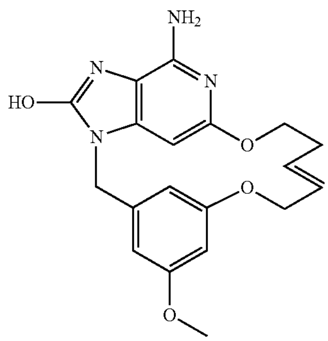 [SMILES: COc1cc2cc(c1)OC/C=C/CCOc1cc3c(nc(O)n3C2)c(N)n1] | 0.18 | 1 | 0.04 | 2 |
| 16 | 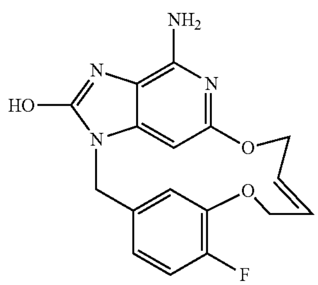 [SMILES: Nc1nc2cc3c1nc(O)n3Cc1ccc(F)c(c1)OC/C=C/CO2] | 2.02 | 2 | 0.47 | 2 |
| 17 | 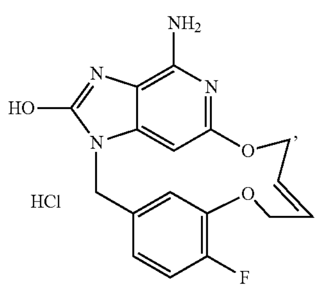 [SMILES: Nc1nc2cc3c1nc(O)n3Cc1ccc(F)c(c1)OC/C=C/CO2 ; Cl] | 1.88 | 2 | 0.39 | 4 |
| 18 | 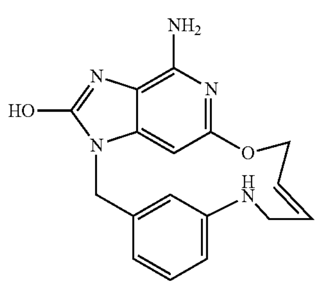 [SMILES: Nc1nc2cc3c1nc(O)n3Cc1cccc(c1)NC/C=C/CO2] | 8.02 | 1 | 1.11 | 2 |
| 19 | 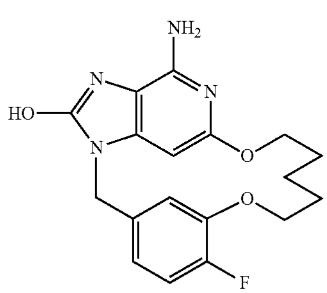 [SMILES: Nc1nc2cc3c1nc(O)n3Cc1ccc(F)c(c1)OC/C=C/CCO2] | 14.96 | 2 | 2.22 | 4 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 20 | (structure with HCl) | 4.99 | 1 | 1.61 | 2 |
| 21 | (structure) | 0.9 | 1 | 0.25 | 3 |
| 22 | (structure with HCl) | 1.83 | 1 | 0.39 | 2 |
| 23 | (structure) | 16.74 | 2 | 8.98 | 4 |
| 24 | (structure) | | | 2.14 | 4 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 25 | 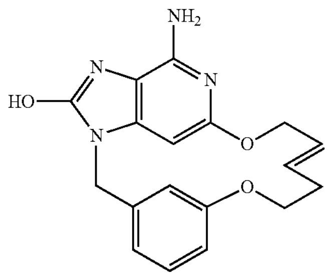 [SMILES: Nc1nc2cc3c1nc(O)n3Cc1cccc(c1)OCC/C=C/CO2] | 1.92 | 1 | 0.53 | 2 |
| 26 | 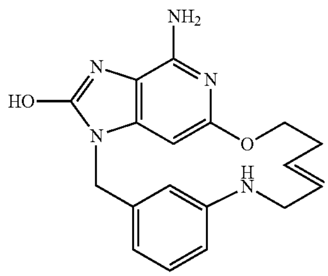 [SMILES: Nc1nc2cc3c1nc(O)n3Cc1cccc(c1)NC/C=C/CCO2] | 1.88 | 2 | 0.37 | 4 |
| 27 | 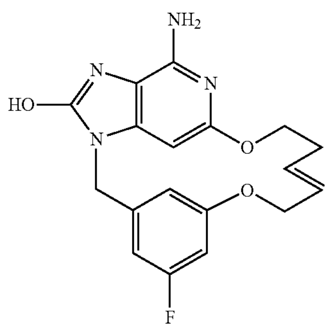 [SMILES: Nc1nc2cc3c1nc(O)n3Cc1cc(F)cc(c1)OC/C=C/CCO2] | 1.35 | 1 | 0.14 | 2 |
| 28 | 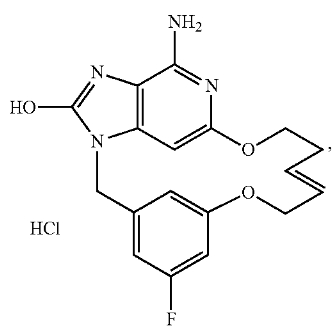 [SMILES: Nc1nc2cc3c1nc(O)n3Cc1cc(F)cc(c1)OC/C=C/CCO2 ; Cl] | 0.91 | 1 | 0.15 | 2 |
| 29 | 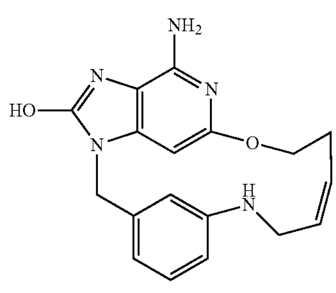 [SMILES: Nc1nc2cc3c1nc(O)n3Cc1cccc(c1)NC/C=C\CCO2] | 1.14 | 2 | 0.48 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 30 | 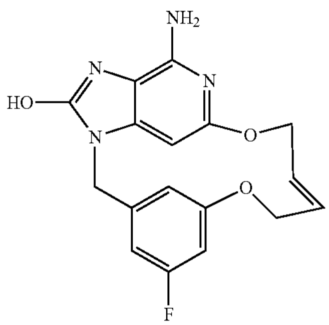 [SMILES: Nc1nc2cc3c1nc(O)n3Cc1cc(F)cc(c1)OC/C=C/CO2] | 0.64 | 1 | 0.15 | 2 |
| 31 | 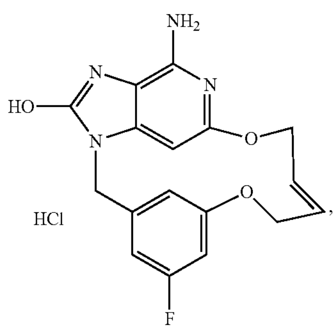 | 1.19 | 1 | 0.15 | 2 |
| 32 | 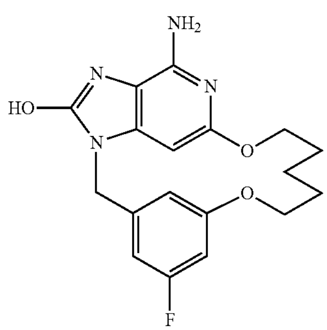 | 2.92 | 2 | 0.49 | 2 |
| 33 | 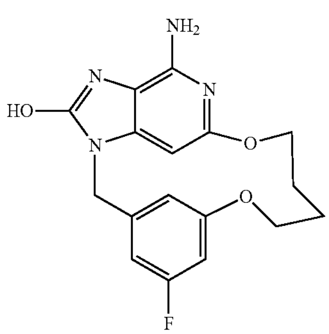 [SMILES: Nc1nc2cc3c1nc(O)n3Cc1cc(F)cc(c1)OCCCCO2] | 2.77 | 1 | 0.45 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 34 | 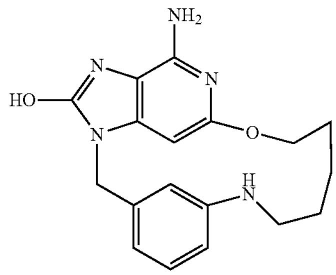 [SMILES: Nc1nc2cc3c1nc(O)n3Cc1cccc(c1)NCCCCCO2] | 8.1 | 2 | 2.11 | 2 |
| 35 | 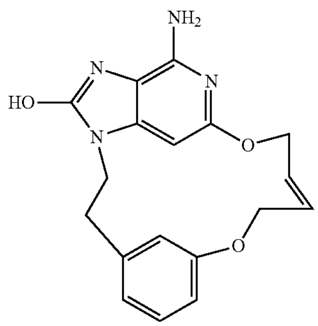 [SMILES: Nc1nc2cc3c1nc(O)n3CCc1cccc(c1)OC/C=C/CO2] | 17.43 | 1 | 1.98 | 2 |
| 36 | | 13.75 | 1 | 1.63 | 4 | n represents the number of experiments performed.

---

The invention claimed is:
1. A compound having formula (I)

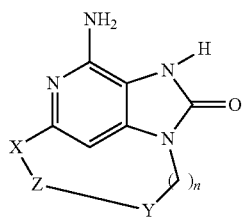

and pharmaceutically accepted salts thereof, wherein
n is 1 or 2;
X is O or NH;
Y is an aromatic ring optionally substituted with one or more substituents each independently selected from the group consisting of $C_{1-4}$alkoxy and halogen; and
Z is selected from the group consisting of $C_{1-10}$alkyl, $C_{1-6}$alkyl-NH—C(O)—$C_{1-6}$alkyl, $C_{1-6}$alkyl-NH—, $C_{1-6}$alkyl-NH—C(O)—$C_{1-6}$alkyl-O—, $C_{1-10}$alkyl-O—, $C_{1-6}$alkyl-O—$C_{1-6}$alkyl-, and $C_{1-6}$alkyl-O—$C_{1-6}$alkyl-O—, wherein said alkyl is saturated or unsaturated, and wherein said alkyl is optionally substituted with an alkyl or alkylhydroxyl.

2. The compound of claim 1, wherein X is O.
3. The compound of claim 1, wherein X is NH.
4. The compound of claim 1, wherein Y is phenyl optionally substituted with methoxy or fluorine.
5. The compound of claim 1, wherein Y is pyridinyl.
6. The compound of claim 1, wherein Z is $C_{1-10}$alkyl, and wherein said alkyl is saturated or unsaturated.
7. The compound of claim 1, wherein Z is $C_{1-6}$ alkyl-NH—, and wherein said alkyl is saturated or unsaturated.
8. The compound of claim 1, wherein Z is $C_{1-10}$alkyl-O—, and wherein said alkyl is saturated or unsaturated.
9. The compound of claim 1 wherein;
n is 1 or 2;
X is O or NH; and
Y is an aromatic ring optionally substituted with one or more substituents each independently selected from the group consisting of $C_{1-4}$alkoxy and halogen.
10. The compound of claim 1, wherein
n is 1 or 2;
X is O or NH;
Y is an aromatic ring optionally substituted with one or more substituents each independently selected from the group consisting of $C_{1-4}$ alkoxy and halogen; and
Z is selected from the group consisting of $C_{1-10}$alkyl, $C_{1-6}$ alkyl-NH—, and $C_{1-10}$alkyl-O—, and wherein said alkyl is saturated or unsaturated.
11. The compound of claim 1, wherein
n is 1 or 2;
X is O or NH;
Y is an aromatic ring optionally substituted with one or more substituents each independently selected from the group consisting of $C_{1-4}$ alkoxy and halogen; and
Z is $C_{1-10}$alkyl, wherein said alkyl is saturated or unsaturated.
12. The compound of claim 1, wherein
n is 1 or 2;
X is O or NH;
Y is an aromatic ring optionally substituted with one or more substituents each independently selected from the group consisting of $C_{1-4}$ alkoxy and halogen; and
Z is $C_{1-10}$alkyl-O—, wherein said alkyl is saturated or unsaturated.

13. The compound of claim 1, wherein
n is 1;
X is O;
Y is an aromatic ring optionally substituted with one or more substituents each independently selected from the group consisting of $C_{1-4}$ alkoxy and halogen; and
Z is $C_{1-6}$ alkyl-NH—, wherein said alkyl is saturated or unsaturated.
14. The compound of claim 1, wherein
n is 1 or 2;
X is O or NH;
Y is an aromatic ring optionally substituted with methoxy or fluorine; and
Z is $C_{1-10}$alkyl-O—, wherein said alkyl is saturated or unsaturated.
15. A compound selected from the group consisting of:

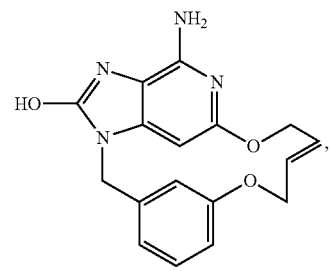

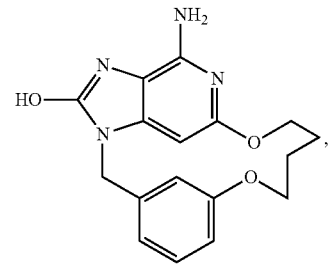

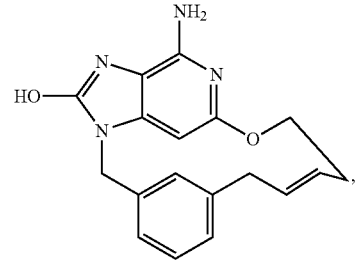

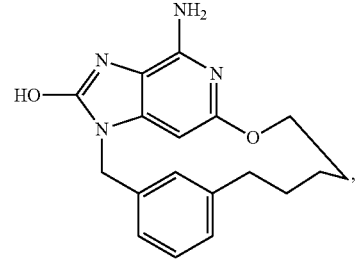

103
-continued
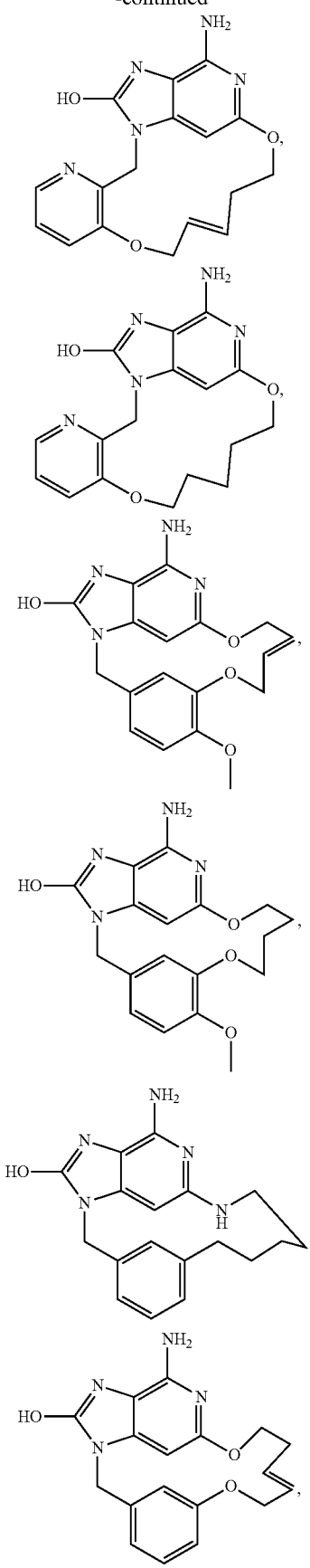
104
-continued
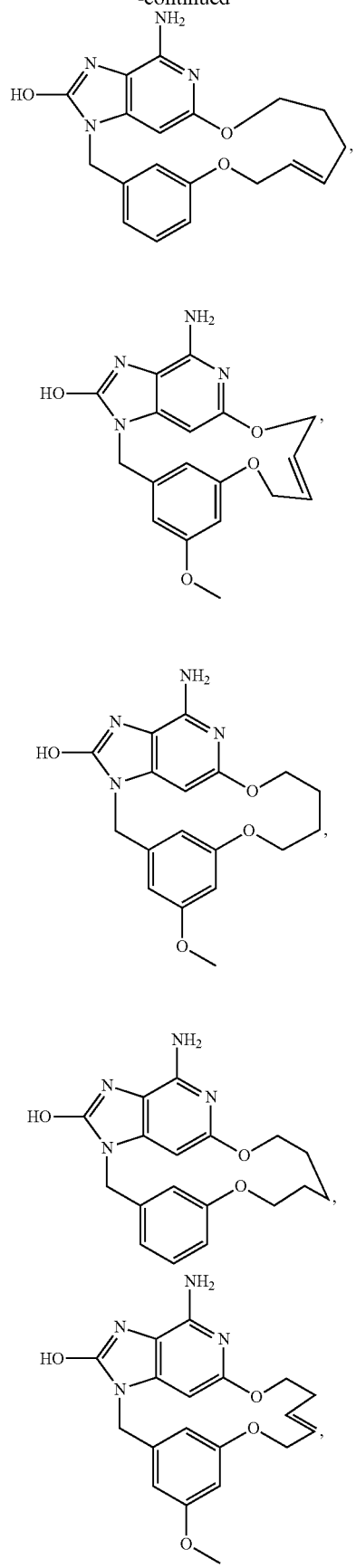

105
-continued
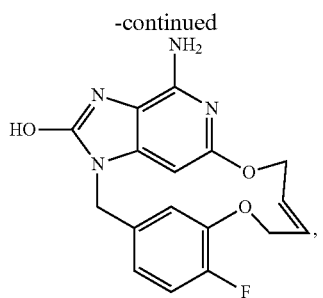
,
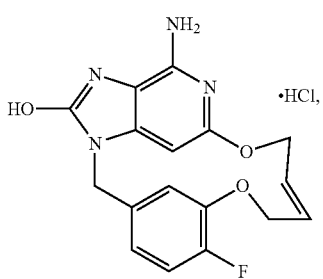
·HCl,
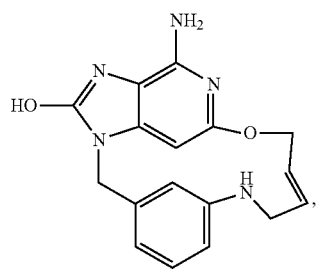
,
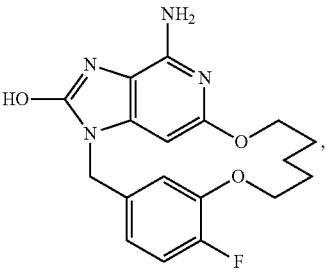
,
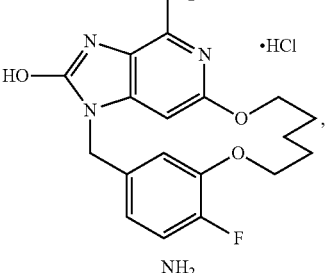
·HCl
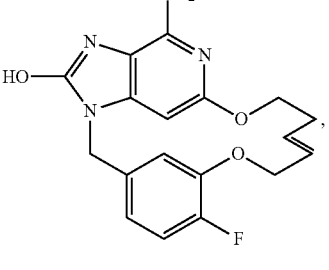
,
106
-continued
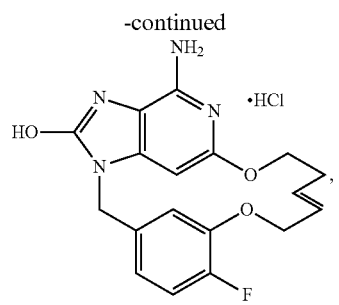
·HCl,
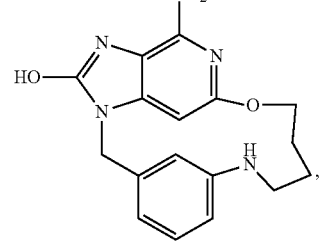
,
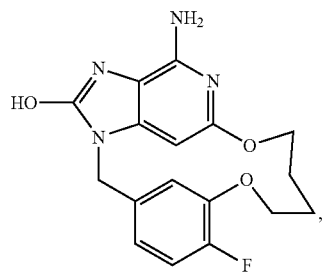
,
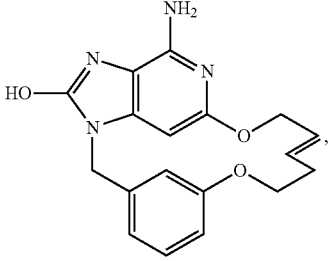
,
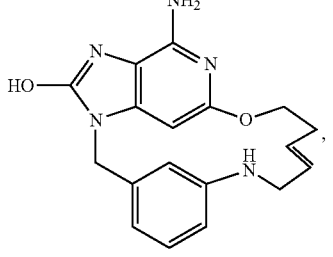
,
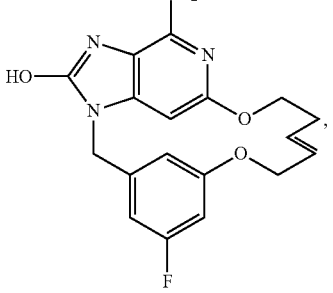
,

107
-continued
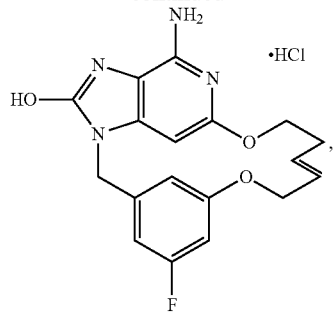
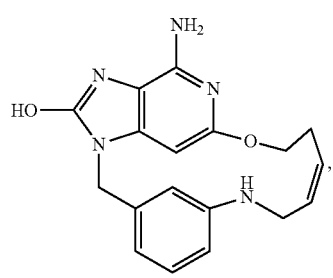
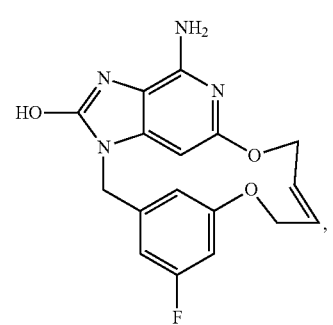
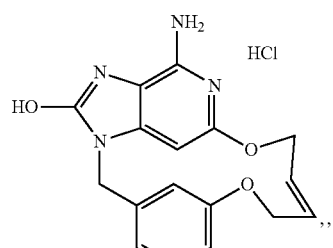
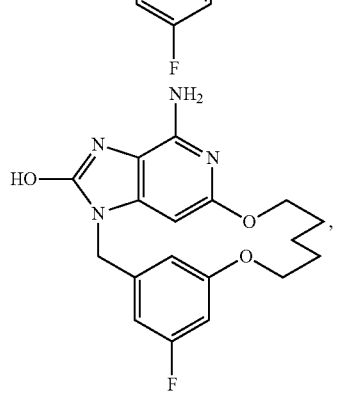
108
-continued
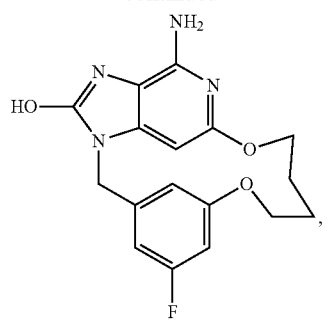
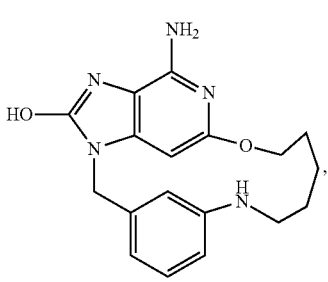
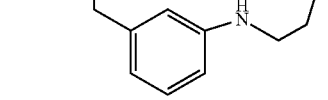
and
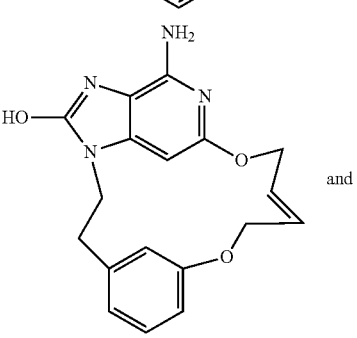
16. A compound according to claim 1 selected from the group consisting of:
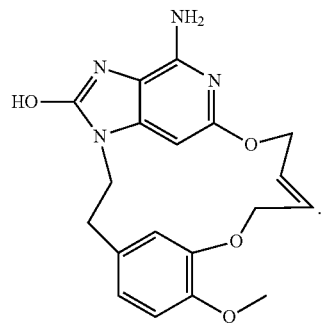

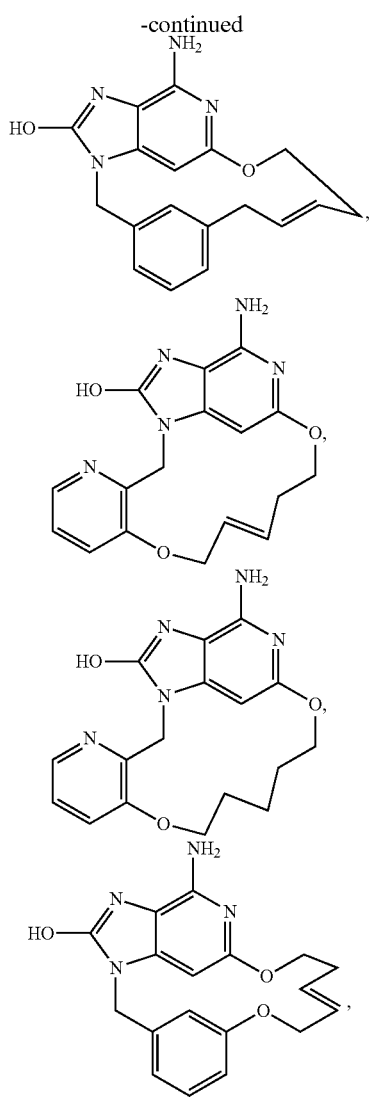

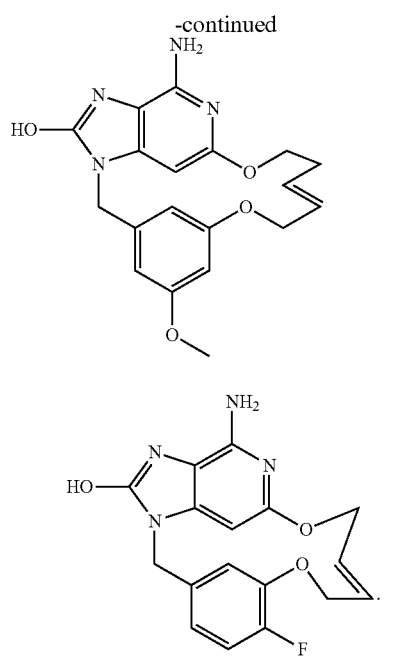

and

17. A pharmaceutical composition comprising a compound of claim 1 or a pharmaceutically acceptable salt or solvate thereof, and one or more pharmaceutically acceptable carriers.

18. A pharmaceutical composition comprising a compound of claim 15 or a pharmaceutically acceptable salt or solvate thereof, and one or more pharmaceutically acceptable carriers.

19. A method of treating a viral infection comprising administering a therapeutically effective amount of at least one compound of claim 1.

20. A method of treating a viral infection comprising administering the pharmaceutical composition of claim 17.

* * * * *

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<221> NAME/KEY: source
<222> LOCATION: 1..15
<223> OTHER INFORMATION: /organism="Artificial Sequence"
    /note="Interferron-stimulated responsive element"
    /mol_type="unassigned DNA"

<400> SEQUENCE: 1
tagtttcact ttccc                                            15